US011154617B2

(12) United States Patent
Baeuerle et al.

(10) Patent No.: US 11,154,617 B2
(45) Date of Patent: *Oct. 26, 2021

(54) MEANS AND METHODS FOR THE TREAMENT OF B CELL NON-HODGKIN LYMPHOMA AND B CELL LEUKEMIA

(75) Inventors: Patrick Baeuerle, Gauting (DE); Peter Kufer, Moosburg (DE); Matthias Klinger, Gilching (DE); Eugen Leo, Cologne (DE)

(73) Assignee: AMGEN RESEARCH (MUNICH) GMBH, Munich (DE)

( * ) Notice: Subject to any disclaimer, the term of this patent is extended or adjusted under 35 U.S.C. 154(b) by 232 days.

This patent is subject to a terminal disclaimer.

(21) Appl. No.: 13/219,120

(22) Filed: Aug. 26, 2011

(65) Prior Publication Data

US 2013/0095103 A1    Apr. 18, 2013

Related U.S. Application Data

(63) Continuation of application No. 12/095,951, filed as application No. PCT/EP2006/011466 on Nov. 29, 2006, now Pat. No. 8,007,796.

(30) Foreign Application Priority Data

Dec. 16, 2005   (EP) .................................... 05027606
Mar. 1, 2006    (EP) .................................... 06004144

(51) Int. Cl.
| | |
|---|---|
| A61K 39/395 | (2006.01) |
| C07K 16/30 | (2006.01) |
| C07K 16/28 | (2006.01) |
| A61K 45/06 | (2006.01) |
| A61K 39/00 | (2006.01) |

(52) U.S. Cl.
CPC ........ *A61K 39/39558* (2013.01); *A61K 45/06* (2013.01); *C07K 16/2803* (2013.01); *C07K 16/2809* (2013.01); *A61K 2039/505* (2013.01); *C07K 2317/31* (2013.01)

(58) Field of Classification Search
CPC ................................................ A61K 39/39558
See application file for complete search history.

(56) References Cited

U.S. PATENT DOCUMENTS

| | | | |
|---|---|---|---|
| 7,635,472 B2 | 12/2009 | Kufer et al. | |
| 2002/0009430 A1 | 1/2002 | Lindhofer et al. | |
| 2009/0191201 A1 | 7/2009 | Heiss et al. | |

FOREIGN PATENT DOCUMENTS

| | | | |
|---|---|---|---|
| WO | WO 99/54440 | 10/1999 | |
| WO | WO 2004/106381 | 12/2004 | |
| WO | WO 2004/106381 A1 | 12/2004 | |
| WO | WO 2005/040220 | 5/2005 | |
| WO | WO 2005/040220 A1 | 5/2005 | |
| WO | WO2010/052014 | * 5/2010 | |

OTHER PUBLICATIONS

Komenaka, Clinics in Dermatology, 2004, vol. 22, p. 251-265.*
Cuzick, Lancet, vol. 361, p. 296-300, 2003.*
Evans, Q J Med, vol. 92, p. 299-307, 1999.*
Hernandez-Ledesma, Peptides, vol. 30, p. 426-430, 2009.*
Schiffman, The New England Journal of Medicine, vol. 353, No. 20, p. 2101-2104.*
Paul, Fudamental Immunology: Third Edition, p. 292-295, 1993.*
Bendig, Methods: A Companion to Methods in Enzymology, vol. 8, p. 83-93, 1995.*
Panka, Proceedings of the National Academy of Sciences, U.S.A., vol. 85, p. 3080-3084, 1988.*
Munodzana, Infection and Immunity, vol. 66, No. 6, p. 2619-2624, 1998.*
Polyak, Blood, vol. 99, p. 3256-3262, 2002.*
Vlasveld, Cancer Immunology Immunotherapy, vol. 40, p. 37-47, 1995.*
Winkler, Blood, vol. 94, No. 7, p. 2217-2224, 1999.*
Weiner, The Journal of Immunology, vol. 147, No. 11, p. 4035-4044, 1991.*
International Search Report for PCT International Application No. PCT/EP2006/011466, dated May 8, 2007 (5 pgs.).
Burgess, Shaheen, Ravera, Jaye, Donohue, and Winkles. Possible dissociation of the heparin binding and mitogenic activities of heparin binding (acidic fibroblast) growth factor-1 from its receptor binding activities by site directedmutagenesis of a single lysine residue. Journal of Cell Biology, 1990. vol. 111, pp. 2129-2138.
Byers. What can randomized controlled trials tell us about nutrition and cancer prevention? CA Cancer Journal for Clinicians, 1999. vol. 49, pp. 353-361.
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.

(Continued)

*Primary Examiner* — Michael Allen
(74) *Attorney, Agent, or Firm* — Marshall, Gerstein & Borun LLP

(57) ABSTRACT

Provided are pharmaceutical means and methods for the prevention, treatment or amelioration of indolent or aggressive B cell non-Hodgkin lymphoma (B NHL) and B cell leukemia comprising the administration of a bispecific single chain antibody construct to a subject in the need thereof and the use of said bispecific single chain antibody construct for the preparation of a pharmaceutical composition for the prevention, treatment or amelioration of indolent or aggressive B cell non-Hodgkin lymphoma (B NHL) and B cell leukemia, whereby said construct is to be administered for at least 1 week in specified daily doses. Moreover, the invention relates to kits comprising a bispecific single chain antibody construct to be used in accordance with this invention.

10 Claims, 16 Drawing Sheets

Specification includes a Sequence Listing.

(56) References Cited

OTHER PUBLICATIONS

Chen, Wiesmann, Fuh, L1, Christinger, MC Kay, De Vos, and Lowman. Selection and analysis of an optimized anti-VEGF antibody: crystal structure of an affinity matured Fab in complex with antigen. Journal of Molecular Biology, 1999. vol. 293, pp. 865-881.
De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.
Granziero, Krajewski, Farness, Yuan, Courtney, Jackson, Peterson, and Vitiello. Adoptive immunotherapy prevents prostate cancer in a transgenic animal model. European Journal of Immunology, 1999. vol. 29, pp. 1127-1138.
Holm, Jafari, and Sundstrom. Functional mapping and single chain construction of the anti-cytokeratin 8 monoclonal antibody TS1. Molecular Immunology, 2007. vol. 44, pp. 1075-1084.
Lazar, Watanabe, Dalton, and Sporn. Transforming growth factor alpha: mutation of aspartic acid 47 and leucine 48 results in different biological activities. Molecular and Cellular Biology, 1988. vol. 8, pp. 1247-1252.
Mac Callum, Martin, and Thornton. Antibody-antigen interactions: contact analysis and binding site topography. Journal of Molecular Biology, 1996. vol. 262, pp. 732-745.
Rudikoff, Giusti, Cook, and Scharff. Single amino acid substitution altering antigen-binding specificity. Proceedings of the National Academy of Sciences, 1982. vol. 79, pp. 1979-1983.
Skolnick and Fetrow. From genes to protein structure and function: Novel applications of computational approaches in the genomic era. Trends in Biotechnology, 2000. vol. 18, pp. 34-39.
Tunnacliffe et al.; The Majority of human CD3 epitopes are conferred by epsilon chain; Int. Immunol. 1989; 1(5):546-50.
Vajdos, Adams, Breece, Presta, De Vos, and Sidhu. Comprehensive functional maps of the antigen-binding site of an anti-ErbB2 antibody obtained with shotgun scanning mutagenesis. Journal of Molecular Biology, 2002. vol. 320, pp. 415-428.
Wu, Nie, Huse, and Watkins. Humanization of a murine monoclonal antibody by simultaneous optimization of framework and CDR residues. Journal of Molecular Biology, 1999. vol. 294, pp. 151-162.
Buysmann et al., Administration of OKT3 as a Two-Hour Infusion Attenuates First-Dose Side Effects1, *Transplantation*, 64(11):1620-3 (1997).—Abstract Only.
Ohshima et al., The World Health Organization classification of malignant lymphoma: Incidence and clinical prognosis in HTLV-1-endemic area of Fukuola. *Pathol. Internatl.* 15:1-12 (2002).

* cited by examiner

A before treatment            after 4 weeks of treatment

B

| Lesion | Localisation | Date<br>a | 26.09.<br>b | Product | Date<br>a | 31.10.<br>b | Product |
|---|---|---|---|---|---|---|---|
| 1 | mediastinum | 2,8 | 1,4 | 3,92 | 2,1 | 1,1 | 2,31 |
| 2 | hilar r | 2,8 | 2,5 | 7,00 | 2,1 | 1,9 | 3,99 |
| 3 | pulmonal r | 3,4 | 1,5 | 5,10 | 1,8 | 1,0 | 1,80 |
| 4 | retroperotonal | 2,1 | 1,6 | 3,36 | 1,2 | 1,0 | 1,20 |
| 5 | iliakal l | 3,6 | 2,4 | 8,64 | 2,1 | 1,2 | 2,52 |
| 6 | nuchal l | 1,3 | 1,0 | 1,30 | 0,8 | 0,6 | 0,48 |
|   |   |   |   Sum | 29,32 |   | Sum | 12,30 |
|   |   |   SCR |   |   |   day 29 |   | -58,0 % |

Figure 12
Before treatment
After 2 weeks of treatment
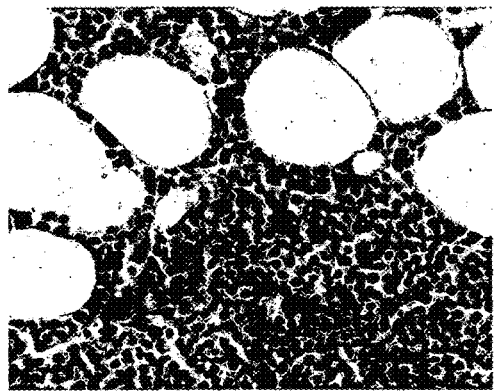
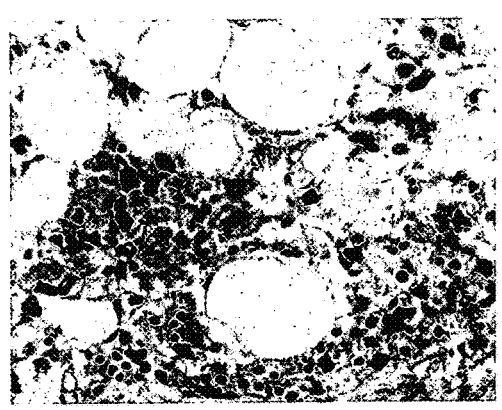

A before treatment        after 2 weeks of treatment

B

|  |  | Date | 02.05 |  | Date | 31.05. |  |
|---|---|---|---|---|---|---|---|
| Lesion | Localisation | a | b | Product | a | b | Product |
| 1 | mediastinal (1) | 12,0 | 3,0 | 36,00 | 7,0 | 2,8 | 19,60 |
| 2 | mediastinal (2) | 4,1 | 4,0 | 16,40 | 3,4 | 2,2 | 7,48 |
| 3 | mediastinal (3) | 6,5 | 5,1 | 33,15 | 4,0 | 2,1 | 8,40 |
| 4 | mediastinal (4) | 3,3 | 3,0 | 9,90 | 2,1 | 1,5 | 3,15 |
| 5 | retroperitonal | 3,0 | 2,7 | 8,10 | 2,3 | 2,4 | 5,52 |
| 6 | mesenterial | 1,9 | 1,5 | 2,85 | 1,0 | 1,3 | 1,30 |
|  |  |  | Sum | 106,40 |  | Sum | 45,45 |
|  | SCR |  |  | day 21 |  |  | -57.2 % | before treatment     after 4 weeks and     after 8 weeks of treatment

Figure 16
after treatment
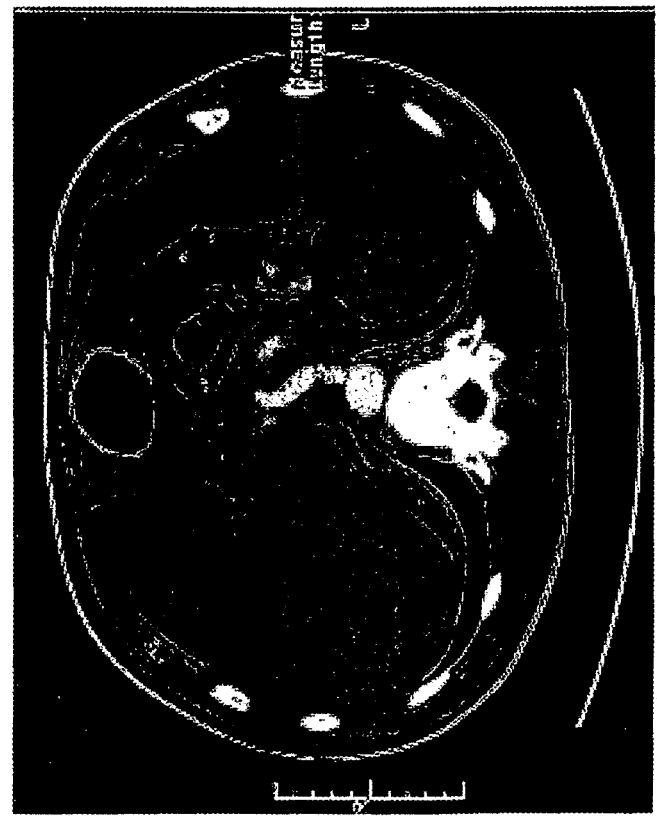
before treatment

MEANS AND METHODS FOR THE TREATMENT OF B CELL NON-HODGKIN LYMPHOMA AND B CELL LEUKEMIA

CROSS-REFERENCE TO RELATED PATENT APPLICATIONS

This application is a Continuation of U.S. patent application Ser. No. 12/095,951, filed Jul. 25, 2008, which is a U.S. National Phase of PCT/EP2006/011,466, filed Nov. 29, 2006, which claims priority to European Patent application 05027606.2, filed Dec. 16, 2005 and European Patent application 06004144.9, filed Mar. 1, 2006, all of which are incorporated herein by reference in their entirety.

The invention relates to pharmaceutical means and methods for immunological, medical interventions based on administering antibody constructs, in particular bispecific single chain constructs to patients. Specifically, the invention relates to pharmaceutical means and methods of treating indolent or aggressive B cell non-Hodgkin lymphoma (B NHL) or B cell leukemia, which means and methods involve the administration of bispecific single chain antibodies. The invention further relates to uses of bispecific single chain antibodies for the manufacture of medicaments for the treatment of indolent or aggressive B cell non-Hodgkin lymphoma (B NHL) or B cell leukemia.

Antibody-based therapeutics are widely used in the treatment of human diseases. Such treatment regimens typically entail multiple "bolus infusions" of antibody therapeutic agent, namely multiple, normally intravenous (i.v.) and high-dose injections of antibody intermittently spread over the entire period of treatment—according to Webster's Online Dictionary, "bolus infusion" denotes a single dose of drug usually injected into a blood vessel over a short period of time; see also the phoenix glossary 5 available through the online medlineplus database. For example, Rituximab (Rituxan), a monoclonal anti-CD20 antibody for treatment of relapsed or refractory low-grade or follicular CD20+B-cell non-Hodgkin lymphoma (NHL), was repeatedly applied as weekly doses over 4-8 weeks (Ghielmini M. J., Clin. Oncol. 2004). Bolus infusion patterns were also described for Alemtuzumab, a humanized anti-CD52 monoclonal antibody in chronic lymphocytic leukemia (O'Brian, 2003, Cancer, 98, 2657-63), Trastuzumab (Herceptin, anti-Her2 antibody) in metastatic breast cancer, Gemtuzumab (Myelotarg, anti-CD33 antibody) in acute myeloic leukemia (AML), Alemtuzumab (Campath, anti-CD52 antibody) in B-cell chronic lymphatic leukaemia (CLL) and Ibritumomab (Zevalin, anti-CD20 antibody) in relapsed or refractory low-grade, follicular or transformed B-cell NHL (for review see Cersosimo, 2003, Am. J. Health-Syst-Pharm., 60, 1531-48). The anti-17-1A monoclonal antibody Edrecolornab (Panorex) was also applied as repeated infusions starting with a high loading dose (500 mg) followed 2 weeks later by 100 mg i.v. every 28 days (Makower, 2003, Cancer Invest., 2, 177-84).

A common phenomenon observed in antibody therapy is the occurrence of infusion-related side effects, such as the cytokine release syndrome ("CRS"). CRS is an immediate complication occurring in response to infusions of antibodies binding to T cells. CRS has been associated with T cell/monocyte activation and, secondarily, with activation of the complement cascade. These processes are mediated through the Fc part of antibodies which are capable of cross-linking T cells and mononuclear cells and activating complement. The pathogenesis of CRS has been attributed to the synthesis of tumor necrosis factor (TNF) alpha, IL-2 and IL-6 and gamma-interferon in response to stimulation of T lymphocytes by OKT3. Generally, such antibodies bind to the T cell receptor, thereby activating the T cells. The cytokines released by the activated T cells (such as TNF alpha, interleukins (IL-2, IL-6) and interferons (IFN gamma) produce a type of systemic inflammatory response similar to that found in severe infection, and characterized by hypotension, pyrexia and rigors. The patients feel very unwell, as if experiencing high fever—indeed the CRS is effectively a type of non-infective fever. Other adverse side effects described to be associated with CRS are fatigue, vomiting, tachycardia, hypertension, headache and back pain.

CRS has also been observed when administering various monoclonal antibodies. For example, the anti-tumor activity of the anti-CD20 antibody Rituximab is harnessed for the treatment of B-cell chronic lymphocytic leukemia (B-CLL). Dose escalation, i.e. increasing doses, achieved by thrice-weekly dosing is necessary for Rituximab to effect significant clinical activity as a single agent (Lin, 2003, Seminar Oncol. 30, 483-92). However, this administration scheme triggers release of the cytokines TNF-alpha and IL-6, the serum levels of which peak 90 minutes after starting a respective infusion. This rise in cytokines is accompanied by fever, chills, hypotension and nausea (Winkler, 1999, Blood, 94, 2217-24). Infusion toxicity could be reduced with appropriate pre-pharmaceutical agent and a stepped-up administration scheme (Lin, 2003, Seminar Oncol. 30, 483-492).

CRS has also been observed when applying other antibody formats, such as bispecific antibodies. Single infusions of bispecific antibody MDX-2H12 (anti-Fc gamma receptor I×anti-Her-2/neu) in combination with GCSF (granulocyte colony-stimulating factor) in breast carcinoma patients led to maximal levels of TNF-alpha and IL-6 at 2 and 4 hours, respectively, following MDX-2H12 infusion. Peak levels of TNF-alpha and IL-6 did not correlate to the dose of bispecific antibody applied (Repp, 2003, Br. J. Cancer, 89, 2234-43).

As described in WO 99/54440, CRS has been observed in an internal clinical study performed with anti-CD19×anti-CD3 bispecific single chain antibody (bscCD19×CD3) applied in repeated infusions to a patient with B-cell derived chronic lymphatic leukaemia (B-CLL). As shown in FIGS. 19 and 20 of WO 99/54440, release of TNF, IL-6 and IL-8 has been found in response to each of the two administered 20 minute-infusions (3 µg and 10 µg of the bispecific single chain antibody, respectively), with cytokine release after each administration. Maximal cytokine release was observed after administration of 10 µg of bispecific single chain antibody.

Ten Berge et al., 1996, Transplant. Proc. 28, 3217-20 describes a study involving continuous infusion of anti-CD3 monoclonal antibody OKT3 for 2 h. The goal of this study was to determine whether thromboembolic complications known to be associated with administration of OKT3 depend on the manner in which this molecule is administered. Generally, administration of OKT3 via continuous infusion was better tolerated than a single bolus infusion.

Continuous infusion has also been described in the prior art for antibody-related pharmaceutical agents. For example, the GD3 ganglioside-specific monoclonal antibody R24 was continuously infused, leading to R24-related toxicities predominantly at doses of 25 and 50 mg/m$^2$ (Alpaugh, 1998, Med. Oncol., 15, 191-8). Continuous infusion over 48 h in two 24-hour infusions of a human IgM monoclonal antibody specific for ganglioside GM3 in patients with metastatic melanoma induced minor side effects during and after infusion (Irie, 2004, Cancer Immunol. Immunother. 53, 110-7). Here, extremely high administration rates of therapeutic antibody were required to achieve a clinical effect, namely in the order of grams of antibody.

Further, an anti-CD16×anti-CD30 bispecific antibody, which was produced as murine IgG1 from hybrid hybridomas was applied in different infusion schedules in patients with Hodgkin's disease (Hartmann, 2001, Clin. Cancer Res., 7, 1873-1881). This antibody activates NK cells via binding to CD16 (Fc-gamma receptor III). Infusions were given either as continuous infusions over 24 h on 4 consecutive days or as a 1 h infusion every other day. The absolute dose of bispecific antibody per infusion was 4 times 25 mg in 5% human albumin solution. After infusion of the bispecific antibody—regardless of the application schedule—no consistent changes in peripheral blood cell counts were observed, although the latter differed strongly between individuals. Patients developed fever, irrespective of whether the antibody treatment schedule was continuous or intermittent. Infusing therapeutic antibody continuously rather than intermittently as boluses did not reduce the incidence or severity of side effects suffered by the patients. It is discussed that it might also be necessary to increase the antitumor efficacy of the bispecific antibody therapy, for example, by concomitant application of cytokines in order to achieve an increase in the amount and/or activation status of the targeted effector cells. Despite the total amount of 100 mg of therapeutic antibody used in the study described above, the major obstacle against a successful and widely applicable therapy with bispecific antibodies is identified as being the limited availability of bispecific antibody. The authors propose that a considerably improved clinical efficacy could be achieved by 1) increasing the doses of the bispecific antibody and 2) increasing the number of treatment cycles.

Accordingly, reduction of undesired side-effects is of need.

It is therefore an aim of the present invention to provide pharmaceutical means and methods for antibody-based medical therapies with increased patient tolerability. Specifically, it is an aim that such means and methods allow for maximal retention of bioactivity of the antibody administered, while undesired and adverse side effects due to this administration are minimized.

The present invention relates to the use of a bispecific single chain antibody construct for the preparation of a pharmaceutical composition for the prevention, treatment or amelioration of a cancer or a non-solid or solid tumor, wherein said bispecific single chain antibody construct is to be permanently administered for a longer period of time.

Accordingly, a first aspect of the invention provides the use of a bispecific single chain antibody construct for the preparation of a pharmaceutical composition for the prevention, treatment or amelioration of indolent or aggressive B cell non-Hodgkin lymphoma (B NHL) or B cell leukemia, wherein said bispecific single chain antibody construct comprises binding domains specific for human CD3 and human CD19, wherein the corresponding variable heavy chain regions ($V_H$) and the corresponding variable light chain regions ($V_L$) are arranged, from N-terminus to C-terminus, in the order, $$V_L(CD19)-V_H(CD19)-V_H(CD3)-V_L(CD3), \text{ (SEQ ID NO.: 2)}$$

$$V_H(CD19)-V_L(CD19)-V_H(CD3)-V_L(CD3), \text{ (SEQ ID NO.: 4)}$$

$$V_H(CD3)-V_L(CD3)-V_H(CD19)-V_L(CD19), \text{ (SEQ ID NO.: 6)}$$

or $$V_H(CD3)-V_L(CD3)-V_L(CD19)-V_H(CD19) \text{ (SEQ ID NO.: 8)}$$

and wherein said bispecific single chain antibody construct is to be administered for at least 1 week in a daily dose of 10 μg to 80 μg per square meter patient body surface area and whereby said daily dose is to be administered over at least 6 h.

In another embodiment, the invention relates to a method for the prevention, treatment or amelioration of indolent or aggressive B cell non-Hodgkin lymphoma (B NHL) or B cell leukemia, the method comprising the administration of a pharmaceutical composition comprising a bispecific single chain antibody construct to a subject in the need thereof, said bispecific single chain antibody construct comprising binding domains specific for human CD3 and human CD19, wherein the corresponding variable heavy chain regions ($V_H$) and the corresponding variable light chain regions ($V_L$) are arranged, from N-terminus to C-terminus, in the order, $$V_L(CD19)-V_H(CD19)-V_H(CD3)-V_L(CD3), \text{ (SEQ ID NO.: 2)}$$

$$V_H(CD19)-V_L(CD19)-V_H(CD3)-V_L(CD3), \text{ (SEQ ID NO.: 4)}$$

$$V_H(CD3)-V_L(CD3)-V_H(CD19)-V_L(CD19), \text{ (SEQ ID NO.: 6)}$$

or $$V_H(CD3)-V_L(CD3)-V_L(CD19)-V_H(CD19), \text{ (SEQ ID NO.: 8)}$$

wherein the bispecific single chain antibody construct is to be administered for at least 1 week in a daily dose of 10 μg to 80 μg per square meter patient body surface area and wherein the daily dose is to be administered over at least 6 h.

In another embodiment, the invention relates to a kit comprising a pharmaceutical composition for the prevention, treatment or amelioration of indolent or aggressive B cell non-Hodgkin lymphoma (B NHL) or B cell leukemia in humans, wherein the pharmaceutical composition comprises a bispecific single chain antibody construct comprising binding domains specific for human CD3 and human CD19, wherein the corresponding variable heavy chain regions ($V_H$) and the corresponding variable light chain ($V_L$) regions are arranged, from N-terminus to C-terminus, in the order, $$V_L(CD19)-V_H(CD19)-V_H(CD3)-V_L(CD3), \text{ (SEQ ID NO.: 2)}$$

$$V_H(CD19)-V_L(CD19)-V_H(CD3)-V_L(CD3), \text{ (SEQ ID NO.: 4)}$$

$$V_H(CD3)-V_L(CD3)-V_H(CD19)-V_L(CD19), \text{ (SEQ ID NO.: 6)}$$

or $$V_H(CD3)-V_L(CD3)-V_L(CD19)-V_H(CD19) \text{ (SEQ ID NO.: 8)}$$

and an instruction sheet in which the administration scheme for the bispecific single chain antibody construct is described to comprise an administration for at least 1 week in a daily dose of 10 μg to 80 μg per square meter patient body surface area and whereby said daily dose is to be administered over at least 6 h.

Another embodiment of the invention relates to a kit for use in the prevention, treatment or amelioration of indolent or aggressive B cell non-Hodgkin lymphoma (B NHL) or B cell leukemia in humans, comprising the administration of a bispecific single chain antibody construct comprising binding domains specific for human CD3 and human CD19, wherein the corresponding variable heavy chain regions ($V_H$) and the corresponding variable light chain regions ($V_L$) regions are arranged, from N-terminus to C-terminus, in the order, $V_L$(CD19)-$V_H$(CD19)-$V_H$(CD3)-$V_L$(CD3), (SEQ ID NO.: 2)

$V_H$(CD19)-$V_L$(CD19)-$V_H$(CD3)-$V_L$(CD3), (SEQ ID NO.: 4)

$V_H$(CD3)-$V_L$(CD3)-$V_H$(CD19)-$V_L$(CD19), (SEQ ID NO.: 6)
or $V_H$(CD3)-$V_L$(CD3)-$V_L$(CD19)-$V_H$(CD19), (SEQ ID NO.: 8)

wherein said bispecific single chain antibody construct is to be administered for at least 1 week in a daily dose of 10 µg to 80 µg per square meter patient body surface area and wherein said daily dose is to be administered over at least 6 h, and wherein said kit contains the following components:
(a) at least 7 individual daily doses of from 140 µg to 320 µg of said bispecific single chain antibody construct; and
(b) a means for having the components arranged in a way to facilitate compliance with the regimen.

The average body surface area of a patient is hereby calculated in the context of the method, kit or use according to the invention to be in a range of 1.7 to 2.2 $m^2$.

Advantageously, the kit of the present invention further comprises, optionally (a) reaction buffer(s), storage solutions and/or remaining reagents or materials required for the recited use. Furthermore, parts of the kit of the invention can be packaged individually in vials or bottles or in combination in containers or multicontainer units.

The manufacture of the kits follows preferably standard procedures which are known to the person skilled in the art.

In order to evaluate safety and tolerability of the anti-CD19×anti-CD3 bispecific single chain antibody (bscCD19×CD3) as described herein, the compound has been administered by long-term continuous infusion to two patients with relapsed non-Hodgkin's lymphoma (B NHL).

The first patient has been diagnosed with a follicular lymphoma in 2000. Although this patient in the past received multiple chemotherapies and immunotherapies, the disease nevertheless progressed. Upon treatment with the anti-CD19×anti-CD3 bispecific single chain antibody construct described herein in accordance with the uses and methods as provided herein, the disease not only came to a halt, but a drastic shrinkage of lymphoma lesions could be achieved for the first time. As documented in the following non-limiting Examples, when this patient received the anti-CD3×anti-CD19 bispecific single chain antibody construct described herein at a dose level of 15 µg/$m^2$/24 h as a continuous infusion for 4 weeks, the treatment was well tolerated, i.e. no significant adverse side effects could be observed. The treatment caused strong T cell activation and expansion. T cells with a cytotoxic phenotype predominantly account for $CD8^+$ T cell expansion. T cell activation and proliferation was induced within the tumor by B lymphoma cells decorated with anti-CD3×anti-CD19 bispecific single chain antibody as described herein. Determination of B cell counts during the treatment showed that said construct can totally eliminate circulating B (lymphoma) cells due to its cytotoxic activity against the lymphoma cells. At a restaging after the treatment, a clear reduction of lymphoma tumor masses according to the response assessment for NHL was found: A decrease in Sum Product Diameters (SPD) of six reference lymphoma lesions of 58.0% was diagnosed, corresponding to a Partial Response (PR) in the tumor response assessment by computed tomography (CT).

The second patient has been diagnosed with a small lymphocytic lymphoma (SLL or B-CLL) in 1999. In the 7-year history of the disease, during which the patient received 7 different chemotherapy regimens as well as immunotherapy and radiotherapy, without demonstrating any major response, treatment of this patient with the anti-CD19×anti-CD3 bispecific single chain antibody construct according to the pharmaceutical means and methods of the invention, for the first time provides for a successful therapy in that more than 50% shrinkage of the reference lymphoma lesions could be achieved. When said second patient has been continuously treated with 15 µg/$m^2$/24 h of the anti-CD19×anti-CD3 bispecific single chain antibody construct described herein for two weeks, circulating B (lymphoma) cells have been efficiently depleted. In addition, total elimination of lymphoma cells from the bone marrow by the anti-CD19×anti-CD3 bispecific single chain antibody construct described herein has been observed. This finding is consistent with a complete bone marrow response which is difficult to achieve by e.g. conventional chemotherapy. At restaging after the treatment, a clear reduction of lymphoma tumor masses was seen: A decrease of 57.2% of the size of six reference lymphoma lesions was diagnosed by computed tomography (CT), corresponding to a Partial Response (PR) in the tumor response assessment.

The terms "bispecific single chain antibody" or "single chain bispecific antibody" or related terms in accordance with the present invention mean antibody constructs resulting from joining at least two antibody variable regions in a single polypeptide chain devoid of the constant and/or Fc portion(s) present in full immunoglobulins. A "linker" as used herein connects V domains of the same specificity, whereas a "spacer" as used herein connects V domains of different specificities. For example, a bispecific single chain antibody may be a construct with a total of two antibody variable regions, for example two VH regions, each capable of specifically binding to a separate antigen, and connected with one another through a short (usually less than 10 amino acids) synthetic polypeptide spacer such that the two antibody variable regions with their interposed spacer exist as a single contiguous polypeptide chain. Another example of a bispecific single chain antibody may be a single polypeptide chain with three antibody variable regions. Here, two antibody variable regions, for example one VH and one VL, may make up an scFv, wherein the two antibody variable regions are connected to one another via a synthetic polypeptide linker, the latter often being genetically engineered so as to be minimally immunogenic while remaining maximally resistant to proteolysis. This scFv is capable of specifically binding to a particular antigen, and is connected to a further antibody variable region, for example a VH region, capable of binding to a different antigen than that bound by the scFv. Yet another example of a bispecific single chain antibody may be a single polypeptide chain with four antibody variable regions. Here, the first two antibody variable regions, for example a VH region and a VL region, may form one scFv capable of binding to one antigen, whereas the second VH region and VL region may form a second scFv capable of binding to another antigen. Within a single contiguous polypeptide chain, individual antibody variable regions of one specificity may advantageously be separated by a synthetic polypeptide linker as described above, whereas the respective scFvs may advantageously be separated by a short polypeptide spacer as described above. Non-limiting examples of bispecific single chain antibodies as well as methods for producing them are shown in WO 99/54440, WO 2004/106381, Mack, J. Immunol. (1997), 158, 3965-70; Mack, PNAS, (1995), 92, 7021-5; Kufer, Cancer Immunol. Immunother., (1997), 45, 193-7; Löffler, Blood, (2000), 95, 6, 2098-103; Brühl, J. Immunol., (2001), 166, 2420-2426.

As used herein, "human CD3" denotes an antigen that is expressed on human T cells as part of the multimolecular T cell receptor complex, the CD3 consisting of five different chains: CD3-epsilon, CD3-gamma, CD3-delta, CD3-eta and CD3 zeta. Clustering of CD3 on T cells e.g. by anti-CD3 antibodies leads to T cell activation similar to the binding of an antigen but independent from the clonal specificity of the T cell subset, as described above. Thus, the term "a bispecific single chain antibody specifically binding with one of its specificities the human CD3 antigen" as used herein relates to a CD3-specific construct capable of binding to the human CD3 complex expressed on human T cells and capable of inducing elimination/lysis of target cells, wherein such target cells carry/display an antigen which is bound by the other, non-CD3-binding portion of the bispecific single chain antibody. Binding of the CD3 complex by CD3-specific binders (e.g. a bispecific single chain antibody as administered according to the pharmaceutical means and methods of the invention) leads to activation of T cells as known in the art; see e.g. WO 99/54440 or WO 2004/106381. Accordingly, a construct appropriate for the pharmaceutical means and methods of the invention is advantageously able to eliminate/lyse target cells in vivo and/or in vitro. Corresponding target cells comprise cells expressing a tumor antigen, such as CD19, which is recognized by the second specificity (i.e. the non-CD3-binding portion of the bispecific single chain antibody) of the mentioned construct. Preferably, said second specificity is for human CD19 which has already been described in WO 99/54440 or WO 2004/106381. According to this embodiment, each antigen-specific portion of the bispecific single chain antibody comprises an antibody VH region and an antibody VL region. Advantageous variants of this bispecific single chain antibody are from N terminus to C terminus:

$$V_L(CD19)-V_H(CD19)-V_H(CD3)-V_L(CD3),$$ (SEQ ID NO.: 2)

$$V_H(CD19)-V_L(CD19)-V_H(CD3)-V_L(CD3),$$ (SEQ ID NO.: 4)

$$V_H(CD3)-V_L(CD3)-V_H(CD19)-V_L(CD19),$$ (SEQ ID NO.: 6)

or $$V_H(CD3)-V_L(CD3)-V_L(CD19)-V_H(CD19).$$ (SEQ ID NO.: 8)

More particularly, within the meaning of the invention, the term "specifically binding" or related terms such as "specificity" is/are to be understood as being characterized primarily by two parameters: a qualitative parameter (the binding epitope, or where an antibody binds) and a quantitative parameter (the binding affinity, or how strongly this antibody binds where it does). Which epitope is bound by an antibody can advantageously be determined by e.g. FACS methodology, ELISA, peptide-spot epitope mapping, or mass spectroscopy. The strength of antibody binding to a particular epitope may advantageously be determined by e.g. known Biacore and/or ELISA methodologies. A combination of such techniques allows the calculation of a signal:noise ratio as a representative measure of binding specificity. In such a signal:noise ratio, the signal represents the strength of antibody binding to the epitope of interest, whereas the noise represents the strength of antibody binding to other, non-related epitopes differing from the epitope of interest. A signal:noise ratio of, for example at least 50, but preferably about 80 for a respective epitope of interest as determined e.g. by Biacore, ELISA or FACS may be taken as an indication that the antibody evaluated binds the epitope of interest in a specific manner, i.e. is a "specific binder". The term "binding to/interacting with" may also relate to a conformational epitope, a structural epitope or a discontinuous epitope consisting of two regions of the human target molecules or parts thereof. In context of this invention, a conformational epitope is defined by two or more discrete amino acid sequences separated in the primary sequence which come together on the surface of the molecule when the polypeptide folds to the native protein (Sela, (1969) Science 166, 1365 and Layer, (1990) Cell 61, 553-6). The term "discontinuous epitope" means in context of the invention non-linear epitopes that are assembled from residues from distant portions of the polypeptide chain. These residues come together on the surface of the molecule when the polypeptide chain folds into a three-dimensional structure to constitute a conformational/structural epitope.

According to the present invention the term "variable region" used in the context with Ig-derived antigen-interaction comprises fragments and derivatives of polypeptides which at least comprise one CDR derived from an antibody, antibody fragment or derivative thereof. It is envisaged by the invention, that said at least one CDR is preferably a CDR3, more preferably the CDR3 of the heavy chain of an antibody (CDR-H3). However, other antibody derived CDRs are also particularly comprised by the term "variable region".

The term "antibody fragment or derivative thereof" relates to single chain antibodies, or fragments thereof, synthetic antibodies, antibody fragments, such as Fab, a F(ab2)', Fv or scFv fragments, single domain antibodies etc., or a chemically modified derivative of any of these. Antibodies to be employed in accordance with the invention or their corresponding immunoglobulin chain(s) can be further modified outside the motifs using conventional techniques known in the art, for example, by using amino acid deletion(s), insertion(s), substitution(s), addition(s), and/or recombination(s) and/or any other modification(s) (e.g. post-translational and chemical modifications, such as glycosylation and phosphorylation) known in the art either alone or in combination. Methods for introducing such modifications in the DNA sequence underlying the amino acid sequence of an immunoglobulin chain are well known to the person skilled in the art; see, e.g., Sambrook et al.; Molecular Cloning: A Laboratory Manual; Cold Spring Harbor Laboratory Press, 2nd edition 1989 and 3rd edition 2001.

The term "peptide" or "polypeptide" as used herein describes a group of molecules which comprise the group of peptides, as well as the group of polypeptides. The group of peptides is consisting of molecules with up to 30 amino acids, the group of polypeptides is consisting of molecules with more than 30 amino acids.

The term "antibody fragment or derivative thereof" particularly relates to peptide or polypeptide constructs comprising at least one CDR, preferably a CDR-H3.

Fragments or derivatives of the recited antibody molecules define peptides or polypeptides which are parts of the above antibody molecules and/or which are modified by chemical/biochemical or molecular biological methods. Corresponding methods are known in the art and described inter alia in laboratory manuals (see Sambrook et al., loc cit.; Gerhardt et al.; Methods for General and Molecular Bacteriology; ASM Press, 1994; Lefkovits; Immunology Methods Manual: The Comprehensive Sourcebook of Techniques; Academic Press, 1997; Golemis; Protein-Protein Interactions: A Molecular Cloning Manual; Cold Spring Harbor Laboratory Press, 2002).

Methods for the identification of motifs in the amino acid sequence of a given polypeptide are known to the person skilled in the art and described in several laboratory manuals (e.g. in Sambrook et al., loc cit.; Mülhardt; Der Experimentator: Molekularbiologie/Genomics; Spektrum Akademischer Verlag, 2001). Furthermore, said methods are exemplified in the appended examples.

The term "administered" as used herein means administration of a therapeutically effective dose of the aforementioned bispecific single chain antibody to an individual. By "therapeutically effective amount" is meant a dose that produces the effects for which it is administered. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

The attending physician and clinical factors will determine the dosage regimen. As is well known in the medical arts, dosages for any one patient depends upon many factors, including the patient's size, body surface area, age, the particular compound to be administered, sex, time and route of administration, general health status, and other drugs being administered concurrently.

As is well known in the medical arts, dosages for any one patient depends upon many factors, including the patient's size, body surface area, age, the particular compound to be administered, sex, time and route of administration, general health status, and other drugs being administered concurrently. A typical dose can be, for example, in the ranges set forth in the embodiments of the invention and the appended examples; however, doses below or above this exemplary range are envisioned, especially considering the aforementioned factors.

As described herein, previous studies have preferably used bolus infusions for administration of therapeutic antibodies. The term "bolus infusion" as used herein refers to an infusion which is interrupted earlier than 6 hours, whereas the term "continuous infusion" refers to an infusion which is allowed to proceed permanently for at least 6 hours without interruption. "Continuous infusion" refers to a permanently administered infusion. Accordingly, in the context of the invention, the terms "permanent" and "continuous" are used as synonyms. Within the meaning of the invention, the term "administration over at least 6 h" denote(s) a situation in which the bispecific single chain antibody used in the pharmaceutical means and methods according to the invention is continuously administered to the body of a patient in a sustained, constant fashion throughout the entire duration required in the pharmaceutical means and methods of the invention. An interruption of the introduction of bispecific single chain antibody is avoided, that is to say a transition from a state in which this antibody is being administered to the body of the patient to a state in which this antibody is no longer being administered to the body of the patient does not, or does not significantly occur over the entire duration of administration required by the pharmaceutical means and methods of the invention for other reasons than replenishing the supply of bispecific single chain antibody being administered or medical interventions which become necessary and the like. In as far as such necessary replenishing leads to a temporary interruption of the introduction of the antibody administered, such administration is still to be understood as being "uninterrupted" or "permanent" in the sense of the pharmaceutical means and methods according to the invention. In most cases, such replenishing will generally be of such a short duration that the time during which antibody is not being introduced into the body of the patient will be vanishingly small when compared to the time planned for the overall administration regimen according to the pharmaceutical means and methods according to the invention. Especially preferred are scenarios in which the administering of the bispecific single chain antibody occurs uninterruptedly or permanently for at least 1 week; or 2, 3, 4, 5, 6, 7, 8, 9, 10, 11 or 12 weeks or even longer. In a most preferred embodiment, the bispecific single chain antibody is continuously administered over 24 h for 4 to 8 weeks, i.e. for 4, 5, 6, 7 or 8 weeks. For example, it may be that upon staging of the treated patient(s) after a 4 week-continuous administration a minimal or partial response (as defined below) to the bispecific single chain antibody treatment may be diagnosed. In this case, the continuous administration may be extended in order to achieve an even better therapeutic result, e.g. a complete response. Continuing uninterrupted administration of the bispecific single chain antibody in the manner of the pharmaceutical means and methods according to the invention for longer periods of time allows the advantageous T cell activation mentioned below to exert its effect for long enough to advantageously clear all diseased cells from the body. Since the rate of uninterruptedly administered bispecific single chain antibody is kept low, application of therapeutic agent may be continued longer without risk of deleterious side effects for the patient.

It has been found that the beneficial and unexpected effects of the pharmaceutical means and methods of the invention can be obtained by administering the bispecific single chain antibody in a daily dose of 10 µg to 80 µg per square meter body surface area. The daily dose may be kept constant over the administration period. However, it is also within the ambit of this embodiment that for the initial day(s) of the infusion period a lower dose of bispecific single chain antibody be administered ("initial dose") prior to the pharmaceutical methods described herein, whereas for the remaining infusion period a higher dose ("maintenance dose") be applied. For example, 5 µg of bispecific single chain antibody per square meter body surface area may be administered at the first day of the infusion period followed by administration of 15 µg per square meter body surface as daily dose for the remaining period. Or 15 µg of bispecific single chain antibody per square meter body surface area may be administered at the first day of the infusion period followed by administration of 45 µg per square meter body surface as daily dose for the remaining period. It is also envisaged that 5 µg of bispecific single chain antibody per square meter body surface area may be administered at the first day of the infusion period, followed by administration of 15 μg of bispecific single chain antibody per square meter body surface area at the second day of the infusion period, followed by administration of 45 μg per square meter body surface as daily (maintenance) dose for the remaining period. Thus, on the first day or on the first and second day of treatment, the bispecific single chain antibody construct as described herein may be administered in a (daily) initial dose of less than 10 μg to 80 μg per square meter patient body surface area in order to slowly adapt the patient's organism to the treatment. Thereafter, the actual maintenance dose of 10 μg to 80 μg per square meter patient body surface area may be administered. The average body surface area of a patient is hereby calculated in the context of the method, kit or use according to the invention to be in a range of 1.7 to 2.2 $m^2$. The inventors have found that by keeping the rate of uninterruptedly administered (i.e. continually infused) bispecific single chain antibody to the absolute minimum required to achieve the desired therapeutic effect over time, the increase of T cell activation described above as being so beneficial may be best realized. In addition to the advantages enumerated below associated with mimicking natural T cell activation, application of lower rates of bispecific single chain antibody entails smaller absolute amounts of bispecific single chain antibody administered. This results in less costs for the individual patient, making treatment according to the pharmaceutical means and methods of the invention affordable to a broader segment of patients in need thereof. Within the meaning of the invention, the term "B cell non-Hodgkin lymphoma" or "B cell derived non-Hodgkin lymphoma" comprises both indolent and aggressive B cell non-Hodgkin lymphoma (B NHL). The term "indolent or aggressive B cell non-Hodgkin lymphoma (B NHL)" as used herein represents malignant B cell-derived tumorous diseases. Indolent B NHL are low malignant lymphomas. Aggressive B-NHL are high malignant lymphomas. The B cell non-Hodgkin lymphoma (B NHL) may advantageously be a follicular lymphoma, lymphoplamacytic lymphoma, marginal zone cell lymphoma, mantle cell lymphoma (MCL), diffuse large B cell lymphoma (DLBCL), Burkitt's lymphoma, small lymphocytic lymphoma (SLL/CLL) and any other B cell derived subtype. The term "B cell leukemia" as used herein may advantageously be any B cell leukaemia (e.g. chronic lymphocytic leukaemia or acute lymphocytic leukaemia). For further reference, see e.g., http colon-slash-slash cancer.org. Preferably, indolent non-Hodgkin B cell lymphoma may be treated with a bispecific single chain antibody directed against both human CD3 and human CD19 as demonstrated in the following examples.

The term "prevention" as used herein is to be understood as follows: After complete remission of the lymphoma lesion(s) in a human patient after chemotherapeutic or radiological treatment of the lymphoma lesion(s) it may be the case that not all lymphoma cells could be eliminated from the body. However, these remaining tumor cells may give rise to recurrent lymphomas. The pharmaceutical means and methods of the invention can be used to kill these remaining tumor cells in order to prevent recurrence of the lymphoma (originating from the occult lymphoma cells remaining in the body after primary therapy). In this way, the pharmaceutical means and methods help to prevent disease relapse in patients with B NHL or B cell leukemia.

In internal clinical studies, the safety profile of an anti-CD19×anti-CD3 bispecific single chain antibody has been further evaluated. As a result, undesired first dose effects have been found upon repeated bolus infusions of equal doses of bispecific single chain antibody to patients with refractory B cell malignancies. As shown herein below, CRS intensity was highest upon administration of the first dose, with decreasing response to subsequent infusions of anti-CD19×anti-CD3 bispecific single chain antibody. After 6 infusions almost no induction of cytokine levels as compared to baseline levels has been observed. Also when escalating doses of bispecific single chain antibody have been administered to patients with relapsed or refractory B-cell chronic lymphocytic leukemia, a reduction in CRS intensity could be observed after repeated administration of bispecific single chain antibody. Without being bound by theory, the indicated phenomenon is most probably attributed to an adaptation of T cells to a repeated stimulus ("T cell silencing"). Moreover, when monitoring T cell numbers in the treated patients, robust fluctuations of T cell numbers have been found upon each infusion, suggesting a short-term, burst-like T cell activation. Biological activity of anti-CD19×anti-CD3 bispecific single chain antibody could be demonstrated in these studies, resulting in T cell activation, cytokine release, and decrease in B cell counts, but no optimal biological dose (OBD) was defined. Moreover, adverse side effects associated with CRS have been observed.

In contrast and as surprisingly found in the context of the present invention, the desirable biological effects, i.e. long term T cell activation and expansion and cytotoxic activity against tumor cells by the bispecific single chain antibody described herein can be achieved (while reducing, minimizing or completely abolishing undesirable side effects normally associated with bolus application of a therapeutic antibody) e.g. by administration of the bispecific single chain antibody for at least 1 week in a daily dose of 10 μg to 80 μg per square meter patient body surface area, whereby said daily dose is administered over at least 6 h. As documented in the appended non-limiting examples, low amounts of bispecific single chain antibody, i.e. 15 μg/$m^2$ of bispecific single chain antibody continuously administered over 24 h over at least two weeks to patients with small lymphocytic lymphoma (SLL/CLL) or follicular lymphoma are sufficient for long term T cell activation and proliferation in vivo, resulting in a substantial anti-tumor response: Two patients had a partial response (PR), i.e. a shrinkage of six reference lymphomas of more than 50%. In addition, in one of these patients, efficient depletion of lymphoma cells from bone marrow has been demonstrated which is difficult to achieve by conventional approaches such as chemotherapy. Importantly, such low doses of bispecific single chain antibody lead to a more physiological T cell response in patients as compared to bolus administration of bispecific single chain antibody. In addition, the methods and uses as provided herein do not cause significant adverse side effects usually associated with T cell activation, such as CRS. These low doses are still capable of inducing a beneficial anti-tumor response in patients with indolent or aggressive B cell non-Hodgkin lymphoma (B NHL) or B cell leukemia.

With previous administration schemes using repeated bolus infusions, even with the lowest starting dose administered in internal phase I clinical trials, a sudden decline in peripheral blood leukocyte counts, including CD3+, CD4+, and CD8+ T cells, has been observed (see examples). One explanation for this drop is the sudden adhesion and—at least partial—migration of activated T cells and other activated leukocytes into tissues. The resulting endothelial dysfunction and disturbance of local cytokine profiles caused by this burst-like T cell activation of bolus-administered bispecific single chain antibody is believed to significantly contribute to adverse side effects usually observed in CRS. In contrast, as demonstrated in the following examples, the pharmaceutical means and methods according to the invention allow a more gradual activation (and shifting) of T cell populations suggesting that the amount of released cytokines is drastically reduced. The provision of pharmaceutical means and methods according to the invention therefore avoids phenomena such as a sudden disturbance of local cytokine networks. Consequently, no significant adverse side effects have been reported from patients treated according to the methods and uses of the present invention. Moreover, administration of bispecific single chain antibody according to the pharmaceutical means and methods of the invention does not cause any dramatic T cell fluctuations as observed, for instance, upon bolus infusions of bispecific single chain antibody.

As shown in the examples, although a slight decrease in T cell number could be observed at the beginning of the infusion period (which is most probably due to the co-administered steroid), treatment according to the invention rather leads to a increasing number of activated T cells in the blood. Specifically, numbers of cytotoxic CD8+ T cells increase due to proliferation. This is of particular relevance for tumorous diseases showing unfavourable effector:target cell (E:T) ratios, such as B cell lymphoma lesions, reaching E:T ratios of 1:100-1:1000 in vivo. Such unfavourable E:T ratios may result in much slower B cell killing as suggested by prior in vitro experiments. Under such conditions it has to be presumed that the same T cells have the potential to repeated B cell killing leading to a significant reduction of tumor mass. Furthermore, it can be hypothesized that an expansion of the T cell pool localized in the B cell malignancy (e.g., in the B cell lymphoma) to improve E:T ratio may be required to achieve a therapeutic outcome. Since the pharmaceutical means and methods according to the invention provide for at least constant or even increasing numbers of activated T cells in the bloodstream, the cytotoxic potential against tumorous cells, for instance, tumorous B cells in B cell lymphomas is improved over time.

Moreover, pharmaceutical means and methods according to the invention lead to long-term activation of CD8+ T cells as exemplified by T cell activation marker HLA-DR (long term activation marker) compared to CD69 or CD25 (short term activation marker). As pointed out above, the low amount of anti-CD19×anti-CD3 bispecific single chain antibody continuously administered is sufficient to increase the number of activated CD8+ T cells over a long period of time, as demonstrated, e.g., in the appended examples and in FIGS. 6 to 8. This is in clear contrast to the burst-like T cell activation observed upon bolus-administered anti-CD19× anti-CD3 bispecific single chain antibody; see, e.g., FIG. 1. The prolonged presence of bispecific single chain antibody according to the pharmaceutical means and methods of the invention allowing gradual long-term T cell activation and proliferation is thus particularly suitable for the treatment of tumorous diseases characterized by unfavourable E:T ratios, such as B cell lymphomas. Moreover, it has been observed that after a restart of the continuous infusion (e.g. after medical intervention), a much faster and stronger activation and expansion of cytotoxic CD8+ T cells occurred. Thus, it is preferred that several rounds of infusion cycles followed by infusion-free periods be carried out. For example, it is within the scope of this invention that a patient may receive a continuous infusion of the bispecific single chain antibody defined herein for four weeks followed by an infusion-free period of four weeks. Thereafter, this sequence may be repeated once, two, three times or even more often.

Moreover, although long-term T cell activation can be observed in patients treated according to the pharmaceutical means and methods of the invention, associated adverse side effects are significantly reduced or even eliminated. CRS-related side effects can thus be minimized or prevented by application of the bispecific single chain antibody according to the pharmaceutical means and methods of the invention.

Finally, it should be stressed that although only low amounts of bispecific single chain antibody have been applied in the uses, methods and kits described herein, the antibody treatment is very effective in depleting tumorous B cells, thereby causing a detectable anti-tumor response in vivo. This is exemplified by the B cell counts in FIGS. 9 and 11 and by the lymphoma size reductions shown in FIGS. 10 and 13. In particular, two patients treated according to the pharmaceutical means and methods according to the invention had a partial response, i.e. a shrinkage of six reference lymphoma lesions of more than 50%. In addition, in one of these patients, efficient depletion of lymphoma cells from bone marrow has been demonstrated; see FIG. 12. Therefore, when applying the pharmaceutical means and methods of the invention, adverse side effects are reduced or eliminated without any concomitant decrease of cytotoxic activity.

In contrast, a bolus administration-mode of antibody therapeutics results in a massive, short-term T cell activation and subsequent relocation/shifting of activated T cells to endothelium and tissue with only small numbers of effective T cells left in the bloodstream. As well known in the art, endothelium can be seriously disrupted by massive T cell activation and subsequent adhesion of T cells to endothelial cells and migration into tissues. Under pathological conditions, such a sudden T cell activation can be observed, for example, in massive sepsis caused by bacterial toxins (see, e.g., Li (2004), Br. J. Pharmacol. 141(4): 709-16; Matzen (2004), Virus Res. 104(2): 145-55; Jacob HS. (1980) Arch. Pathol. Lab. Med. 104(12): 617-20; Salyer (1990), Am. J. Pathol. 136(4): 831-41; Okajima (2004) Curr. Vasc. Pharmacol. 2(2): 125-33; Ferrero (2004) Methods Mol. Med. 98: 127-36). Moreover, this burst-like T cell activation is associated with adverse side effects caused by cytokines. With previous dosing studies using repeated bolus infusions, even with the lowest starting dose administered in internal phase I clinical trials, a sudden decline in peripheral blood leukocyte counts, including CD3+, CD4+, and CD8+ T cells, has also been observed. One explanation for this drop is the sudden adhesion and—at least partial—migration of activated T cells and other activated leukocytes into tissues. It is hypothesized that such an abrupt activation and shifting of enormous activated T cell populations (approximately 70% of the human T cell pool reside in the peripheral blood at any time) result in a disturbance of T cell homeostasis and local cytokine profiles in tissues.

Thus, a significantly prolonged exposure to the bispecific single chain antibody and a significant decrease in dose given per time unit as compared to prior phase I studies potentially increases tolerability and maximize anti-tumor activity of the drug.

In previous clinical studies investigating safety and tolerability of repeated bolus infusions of bispecific single chain anti CD19×anti CD3 antibody, undesired fluctuations of T cell numbers have been observed after each infusion, suggesting a burst-like T cell activation as dependent on each infusion. Notably, this effect has been found for the administration of both equal and escalating doses of the indicated bispecific single chain antibody.

The provision of pharmaceutical means and methods according to the invention manifests a qualitatively distinct pattern of T cell activation as compared to that obtained following bolus infusion of greater amounts of antibody. Specifically, it has been found that administration of bispecific single chain antibody according to the pharmaceutical means and methods of the invention leads to a slow initial increase followed by the maintenance of a constant, or even increasing cellular immune response in vivo mimicking that observed in the course of natural infections, for example, viral infections. In a natural infection, circulating T cells specific for a pathogenic antigen become activated when they encounter this antigen in draining lymphoid tissues. Following such activation in a natural infection, a proliferation of T cell subsets occurs, which are specific for the pathogenic antigen. This increase correlates, due to the proliferation of CD8$^+$ T cells, to an increase in cytotoxic potential against the invading pathogen, or towards cells infected by this pathogen. The pharmaceutical means and methods of the invention thus simulate the immune response to a natural infection, for instance, a viral infection in that a slow and gradual increase in the number of activated T cells occurs.

In summary, the present invention provides for major advantages:
- simulation of a more physiological T cell response, no dramatic T cell fluctuations, constant or even increasing number of effector (cytotoxic) T cells in the bloodstream
- reduced cytokine release/no first dose effects due to low amounts of bispecific single chain antibody, with efficient anti-tumor (CTL) activity (two patients with partial response, one of whom with efficient depletion of lymphoma cells from bone marrow)
- reduced adverse side effects
- minimizing of aberrant T cell activation caused by repeated T cell activation and deactivation cycles
- long-term activation and expansion of cytotoxic T cells
- prolonged presence of the drug helps to overcome unfavourable E:T ratios frequently present in lymphoma lesions leading to much slower B cell kill than originally anticipated
- prolonged presence of the drug allows repetitive B cell killing to take place, performed by one and the same T cell, and thus assures reduction of significant tumor masses
- an expansion of a localized T cell pool improves E:T ratio and therapeutic outcome
- there is a notable variation in in vitro activity (reflected in EC$_{50}$ value variation) among different Peripheral Blood Mononuclear Cell (PBMC) donors. Extended exposure time to the drug improves anti-CD19 directed cytotoxic activity in a significant proportion of patients.

Thus, a significantly prolonged exposure to the drug and a significant decrease in dose given per time unit as compared to prior phase I studies potentially increase tolerability and maximize anti-tumor activity of the drug resulting in a better safety profile.

Administration according to the regimen of the invention may be over 6 h, 7 h, 8 h, 9 h, 10 h, 11 h, 12 h, 13 h, 14 h per day, or even over 24 h. Preferably, administration according to the regimen of the invention is over 10 h, more preferably over 12 h, or even more preferred over 24 h.

In a preferred embodiment of the method, use or kit of the invention, the daily dose of said bispecific single chain antibody construct is administered over at least 8 h, more preferably at least 10 h.

In an even more preferred embodiment of the method, use or kit of the invention, the daily dose is administered over at least 12 h, 14 h, 16 h, 18 h, 20 h or 22 h. Most preferably, the daily dose is administered during the whole day, i.e. over 24 h.

In another preferred embodiment of the method, use or kit of the invention said V$_H$ and V$_L$ regions of said CD3 specific domain are derived from an CD3 specific antibody selected from the group consisting of: OKT-3, X35-3, VIT3, BMA030 (BW264/56), CLB-T3/3, CRIS7, YTH12.5, F111-409, CLB-T3.4.2, TR-66, WT31, WT32, SPv-T3b, 11D8, XIII-141, XIII-46, XIII-87,12F6, T3/RW2-8C8, T3/RW2-4B6, OKT3D, M-T301, SMC2 and F101.01. Each of these antibodies is well described in the art.

More particularly, said V$_H$ region of said CD3 specific domain comprises at least one CDR3 region comprising or being the amino acid sequence shown in SEQ ID NO. 11, said V$_H$ region of said CD3 specific domain comprises at least one CDR2 region comprising or being the amino acid sequence shown in SEQ ID NO. 10 and/or said V$_H$ region of said CD3 specific domain comprises preferably at least one CDR1 region comprising or being the amino acid sequence shown in SEQ ID NO. 9.

The construct of the invention may also comprise V$_L$ regions. Such V$_L$ region of said CD3 specific domain may comprise at least one CDR3 region comprising or being the amino acid sequence of SEQ ID NO. 14, said V$_L$ region of said CD3 specific domain comprises at least one CDR2 region comprising or being the amino acid sequence of SEQ ID NO. 13 and/or said V$_L$ region of said CD3 specific domain comprises at least one CDR1 region comprising or being the amino acid sequence of SEQ ID NO. 12.

It is understood that in a most preferred embodiment, the CDRs as defined above (CDR1, CDR2, CDR3) are comprised in one single bispecific construct to be administered in accordance with this invention.

In another preferred embodiment of the method, use or kit according to the invention, the V$_H$ region of said CD3 specific domain comprises or is SEQ ID NO 17, the V$_H$ region of said CD19 specific domain comprises or is SEQ ID NO 15, the V$_L$ region of said CD3 specific domain comprises or is SEQ ID NO 18 and/or the V$_L$ region of said CD19 specific domain comprises or is SEQ ID NO 16.

It is also envisaged that the method, use or kit of the invention makes use of a bispecific single chain antibody construct that comprises an amino acid sequence selected from the group consisting of
(a) an amino acid sequence as depicted in SEQ ID NOs 2, 4, 6, or 8;
(b) an amino acid sequence encoded by a nucleic acid sequence as shown in SEQ ID NOs 1, 3, 5, or 7;
(c) an amino acid sequence encoded by a nucleic acid sequence having at least 70%, 80%, 90%, 95% or 99% identity to a nucleic acid sequence of (b), wherein said amino acid sequence is capable of (specifically) binding to CD3 and CD19; and
(d) an amino acid sequence encoded by a nucleic acid sequence which is degenerate as a result of the genetic code to a nucleotide sequence of (b), wherein said amino acid sequence is capable of (specifically) binding to CD3 and CD19.

Whether any particular nucleic acid molecule or polypeptide is at least 70%, 80%, 85%, 90%, 95%, 96%, 97%, 98% or 99% identical to a nucleotide or amino acid sequence defined herein can be determined conventionally using known computer programs. A preferred method for determining the best overall match between a query sequence (a sequence defined herein) and a subject sequence, also referred to as a global sequence alignment, can be determined using the FASTDB computer program based on the algorithm of Brutlag et al. (Comp. App. Biosci. 6:237-245 (1990)). In a sequence alignment the query and subject sequences are both DNA sequences. An RNA sequence can be compared by converting U's to T's.

In a preferred embodiment of the method, use or kit of the invention said variable domains are connected by additional linker and/or spacer sequences as defined above and as shown, for example, in WO 2004/106381.

In a preferred embodiment of the method, use or kit of the invention the daily administration is continued for at least 2 weeks, at least 3 weeks, at least 4 weeks or at least 8 weeks. Accordingly, it is also envisaged that the administration is carried out on a permanent basis for at least 6 h per day, preferably for at least 8 h per day, more preferably at least 10 h per day, most preferably 24 h per day, for at least 1, 2, 3, 4, 5, 6, 7, or 8 weeks or even longer. It is also envisaged that several rounds of infusion cycles followed by infusion-free periods be carried out. For example, a patient may receive a continuous infusion of the bispecific single chain antibody defined herein for four weeks followed by a infusion-free period of four weeks. Thereafter, this sequence may be repeated once, two, three times or even more often, until the lymphoma lesions are under detectable level by conventional means, e.g. computed tomograpy. Advantageously, administration is extended until a complete response is achieved, i.e. all or essentially all lymphoma cells be killed. Moreover, it has been observed that after a restart of the continuous infusion (e.g. after an infusion-free period or after medical intervention), a much faster and stronger activation and expansion of cytotoxic CD8+ T cells occurred. Thus, it is preferred that several rounds of infusion cycles followed by infusion-free periods be carried out.

In another preferred embodiment of the method, use or kit according to the invention, the pharmaceutical composition is administered in combination with one or more further pharmaceutical agents.

The present invention is also useful in co-therapy approaches and in (a) regimen(s) of co-therapy. In certain embodiments, the bispecific single chain antibodies as defined herein are to be administered in combination with one or more other therapies. In certain embodiments, the bispecific single chain antibodies as defined herein are to be administered to a patient concurrently with one or more other therapies. Preferably, such therapies are useful for the treatment of B NHL or B cell leukaemia as defined herein. The term "concurrently" is not limited to the administration of pharmaceutical or therapeutic agents at exactly the same time, but rather it is meant that the bispecific single chain antibodies as defined herein and the other agent are to be administered to a subject in a sequence and within a time interval such that the bispecific single chain antibodies as defined herein can act together with the other agent to provide an increased benefit than if they were administered otherwise. For example, each pharmaceutical or therapeutic agent may be administered at the same time or sequentially in any order at different points in time; however, if not administered at the same time, they should be administered sufficiently close in time so as to provide the desired therapeutic or pharmaceutical effect.

Each (co-)therapeutic agent can be administered separately, in any appropriate form and by any suitable route. In other embodiments, the bispecific single chain antibodies as defined herein are to be administered before, concurrently or after surgery. Preferably the surgery completely removes localized lymphomas or reduces the size of large tumors. Surgery can also be done as a preventive measure or to relieve pain.

The dosage amounts and frequencies of administration provided herein are encompassed by the terms therapeutically effective. The dosage and frequency further will typically vary according to factors specific for each patient depending on the specific therapeutic or pharmaceutical agents administered, the severity and type of B NHL or B cell leukemia, the route of administration, as well as age, body weight, response, and the past medical history of the patient. Suitable regimens can be selected by one skilled in the art by considering such factors and by following, for example, dosages reported in the literature and recommended in the Physicians' Desk Reference (59th ed., 2005).

In some embodiments, therapy by administration of the bispecific single chain antibodies as defined herein may be combined with the administration of one or more therapies such as chemotherapies, radiation therapies, hormonal therapies, and/or biological therapies/immunotherapies. Pharmaceutical or therapeutic agents include, but are not limited to, proteinaceous molecules, including, but not limited to, peptides, polypeptides, proteins, including post-translationally modified proteins, antibodies etc.; or small molecules (less than 1000 daltons), inorganic or organic compounds; or nucleic acid molecules including, but not limited to, double-stranded or single-stranded DNA, or double-stranded or single-stranded RNA, as well as triple helix nucleic acid molecules. Pharmaceutical or therapeutic agents may be derived from any known organism (including, but not limited to, animals, plants, bacteria, fungi, and protista, or viruses) or from a library of synthetic molecules.

Said co-therapy comprises co-administration of one or more therapeutic or pharmaceutical agents before, during and/or following the uninterrupted administration of the bispecific single chain antibody. Said therapeutic or pharmaceutical agents to be co-administered with the bispecific antibody are preferably chemotherapeutics used in standard Non-Hodgkin's lymphoma (NHL) therapy, such as platinums, anthracyclins, alkylating agents, antimetabolites, topoisomerase inhibitors, antibiotics, mitosis inhibitors, antitubulins and the like. However, the co-therapy may also be intended to reduce inflammation. Here, it is especially preferred to co-administer, in any of the manners set out above, an anti-inflammatory agent, for instance, a glucocorticosteroid. As described in the appended examples, prior to the continuous administration of the anti-CD19×anti-CD3 bispecific single chain antibody, 100 mg steroid has been administered to the patients in order to suppress cytokine production at the initial phase of the continuous administration. Alternatively, steroid may also be administered at the initial phase from day 1 to day 4 of continuous administration of anti-CD19×anti-CD3 bispecific single chain antibody. The dosage of steroid administered e.g. 1 h prior to the continuous infusion at day 1 may be 500 mg, at day 2 (after 24 h of continuous infusion) 250 mg, at day 3 (after 48 h of continuous infusion) 125 mg and at day 4 (after 72 h of continuous infusion) 125 mg. However, it is also envisaged that no steroid is administered before, during, or after continuous administration of anti-CD19×anti-CD3 bispecific single chain antibody. Of course, chemotherapeutics and anti-inflammatory drugs/agents may also be administered in combination. In the event that co-administration occurs during the uninterrupted administration of the bispecific single chain antibody, such co-administration may occur for the entire duration of the administration of said antibody, or for only one or more portions thereof. For example, it is within the ambit of this embodiment of the invention that such co-administration may start prior to the administration of the bispecific single chain antibody, and may end after the uninterrupted administration of the bispecific single chain antibody has begun. In such a case, it may be advantageous to omit any further co-administration throughout the rest of the uninterrupted administration of the bispecific single chain antibody, or it may be alternatively be advantageous to resume co-administration of a pharmaceutical agent at a later point during and/or after the uninterrupted administration of the bispecific single chain antibody. It may also be advantageous to structure the regimen of co-therapy such that any co-administration occurs only before and/or following the uninterrupted administration of the bispecific single chain antibody, but not during the uninterrupted administration. As such, "a regimen of co-therapy" within the meaning of this embodiment of the invention must be understood as comprising, in a chronological sense, the uninterrupted administration of the bispecific single chain antibody. This means that the regimen of co-therapy may in some cases be performed for a longer period of time than the uninterrupted administration of the bispecific single chain antibody, since it is possible to co-administer a pharmaceutical agent as part of the co-therapy prior to and/or following uninterrupted administration of the bispecific single chain antibody. Conversely, the regimen of co-therapy may be performed for a shorter period of time than the uninterrupted administration of the bispecific single chain antibody, since the co-administration of the regimen of co-therapy may take place for only a fraction of time during the uninterrupted administration of the bispecific single chain antibody. Preferably, said steroid is administered according to the scheme and in the dosage shown in the examples or as indicated above.

If co-administration is given as continuous infusion over the whole time period of the uninterrupted administration of the bispecific single chain antibody according to the invention, both agents—the one(s) used for cotherapy and the bispecific single chain antibody—could be combined in one solution. The agent used for cotherapy could be directly added to the solution/formulation in which the bispecific single chain antibody is applied to the patient. Further, the agent used for cotherapy and the bispecific single chain antibody could also be applied in parallel as separate solutions over the same time.

Co-therapy may in some cases be advantageous or necessary, depending on other conditions existing, suspected or expected in the patient undergoing treatment according to the pharmaceutical means and methods of the invention. Such co-administration may occur as one or more bolus applications before, during or/and following the uninterrupted administration according to the pharmaceutical means and methods of the invention. Alternatively, such co-administration may also be of an uninterrupted nature, and may in this case take place at the same time, and even in the same administration vehicle as the uninterrupted administration of the bispecific single chain antibody as set out in the method, kit or use according to the invention.

The bispecific single chain antibody as defined herein and the further therapeutic agent(s) may act synergistically. As used herein, the term "synergistic" refers to a combination of therapies (e.g., a combination of a bispecific single chain antibody as defined herein and (a) further pharmaceutical or therapeutic agent(s) as set forth herein) which is more effective than the additive effects of any two or more single therapies (e.g., one or more pharmaceutical or therapeutic agents). A synergistic effect of a combination of therapies (e.g., a combination of a bispecific single chain antibody as defined herein and (a) further pharmaceutical or therapeutic agent(s) as set forth herein) permits the use of lower dosages of one or more of therapies (e.g., one or more pharmaceutical or therapeutic agents) and/or less frequent administration of said therapies to a patient with a disease, e.g. B NHL or B cell leukaemia as defined herein. The ability to utilize lower dosages of therapies (e.g., pharmaceutical or therapeutic agents) and/or to administer said therapies less frequently reduces the toxicity associated with the administration of said therapies to a subject without reducing the efficacy of said therapies in the prevention or treatment of a disease, e.g. B NHL or B cell leukaemia as defined herein. In addition, a synergistic effect can result in improved efficacy of therapies (e.g., pharmaceutical or therapeutic agents) in the prevention, management, treatment and/or amelioration of B NHL or B cell leukaemia as defined herein. Finally, synergistic effect of a combination of therapies (e.g., pharmaceutical or therapeutic agents) may avoid or reduce adverse or unwanted side effects associated with the use of any single therapy.

In another embodiment, the co-therapy may be intended to reduce inflammation. Here, it is especially preferred to co-administer, in any of the manners set out above, an anti-inflammatory agent, for example, a glucocorticosteroid.

The co-therapy regimen of this embodiment of the invention may also advantageously provide an activation signal for immune effector cells, for cell proliferation or for cell stimulation.

The uninterrupted administration of the bispecific single chain antibody may be intravenous, parenteral, subcutaneous, transdermal, intraperitoneal, intramuscular or pulmonary. The intravenous mode of administration will in most cases be the mode of choice for uninterruptedly administering the bispecific single chain antibody and, as the case may be, for co-administration of a pharmaceutical agent as part of a regimen of co-therapy. As such, intraveneous administration is especially preferred. In this case, a suitable metering device such as the multi-therapy infusion pump model 6060 manufactured by Baxter may advantageously be chosen. Whatever metering device is chosen, it should be of such design and construction as to minimize or, better, preclude an interruption of administration of therapeutic agent in the event of cartridge exchange and/or power cell replacement or recharging. This may be accomplished, for example by choosing a device with a secondary reservoir of bispecific single chain antibody solution apart from the cartridge to be exchanged so that continuous infusion from this secondary reservoir into the patient may continue even while the empty or almost empty cartridge is removed and replaced with a fresh one.

A mode of intraveneous administration and, as the case may be, of co-administration as part of a regimen of co-therapy involves the implantation of a pump into the body of the patient for metering such administration. One of ordinary skill in the art is aware of such metering pumps, for example model 6060 manufactured by Baxter as set forth above.

As a non-limiting example, it may be that the uninterrupted, i.e. continuous administration is to be realized by a small pump system worn by or implanted into the patient for metering the influx of therapeutic agent into the body of the patient. Such pump systems are generally known in the art, and commonly rely on periodic exchange of cartridges containing the therapeutic agent to be infused. When exchanging the cartridge in such a pump system, a temporary interruption of the otherwise uninterrupted flow of therapeutic agent into the body of the patient may ensue. In such a case, the phase of administration prior to cartridge replacement and the phase of administration following cartridge replacement would still be considered within the meaning of the pharmaceutical means and methods of the invention to together make up one "uninterrupted administration" of such therapeutic agent. The same would apply for very long administrations in which the cartridge would require replacement more than once, or in which the power cells driving the pump would require replacement, leading to a temporary offset of the flow of therapeutic solution into the body of the patient.

Appropriate measures should also be taken to minimize the danger of infection at the puncture site of administration into the patient's body, as such long-term wounds are especially prone to such infection. The above also applies for intramuscular administration via a similar delivery system.

The continuous administration may be transdermal by way of a patch worn on the skin and replaced at intervals. One of skill in the art is aware of patch systems for drug delivery suitable for this purpose. It is of note that transdermal administration is especially amenable to uninterrupted administration, as exchange of a first exhausted patch can advantageously be accomplished simultaneously with the placement of a new, second patch, for example on the surface of the skin immediately adjacent to the first exhausted patch and immediately prior to removal of the first exhausted patch. Issues of flow interruption or power cell failure do not arise.

In a further preferred embodiment, the continuous administration is accomplished via a pulmonary route, for example via a tube worn in one or both nostrils of the nose, the tube being connected to a pressurized tank, the content of which is precisely metered.

However, as illustrated herein and in the appended examples, the most preferred mode of administration is an intravenous administration over the given time/time period.

The bispecific single chain antibody as used herein is advantageously in the form of a pharmaceutical composition for administration to a human patient. While the bispecific single chain antibody as used herein may be administered per alone, preferred is administration in a pharmaceutically acceptable carrier. Examples of suitable pharmaceutical carriers are well known in the art and include phosphate buffered saline solutions, water, liposomes, various types of wetting agents, sterile solutions, etc. Compositions comprising such carriers can be formulated by well known conventional methods. These pharmaceutical compositions can be administered to the subject at a suitable dose. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Preparations for parenteral administration include sterile aqueous or non-aqueous solutions, or suspensions. Examples of non-aqueous solvents are propylene glycol, polyethylene glycol, and injectable organic esters such as ethyl oleate. Aqueous carriers include water, aqueous solutions, or suspensions, including saline and buffered media. Parenteral vehicles include sodium chloride solution, Ringer's dextrose, dextrose and sodium chloride, or lactated Ringer's. Intravenous vehicles include fluid and nutrient replenishes, electrolyte replenishers (such as those based on Ringer's dextrose), and the like. Preservatives and other additives may also be present such as, for example, antimicrobials, anti-oxidants, chelating agents, and inert gases and the like. In addition, the composition might comprise proteinaceous carriers, like, e.g., serum albumine or immunoglobuline, preferably of human origin. It is envisaged that the composition might comprise, in addition to the proteinaceous bispecific single chain antibody further biologically active agents, depending on the intended use of the pharmaceutical composition. Such agents might be agents agents acting as cytostatica, agents preventing hyperurikemia, agents inhibiting immune reactions (e.g. corticosteroids, FK506), drugs acting on the circulatory system and/or agents such as T-cell co-stimulatory molecules or cytokines known in the art.

Preferably, the bispecific single chain antibody as defined herein is formulated in a buffer, a stabilizer and a surfactant. The buffer may be a phosphate, citrate, succinate or acetate buffer. The stabilizer may be (an) amino acid(s) and/or a sugar. The surfactants may be detergents, PEGs, or the like. More preferably, the bispecific single chain antibody as defined herein is formulated in citrate, lysine, trehalose and polysorbate 80 (TWEEN® 80). As a diluent for the pharmaceutical composition of the invention, isotonic saline and TWEEN® 80 is preferred.

Preferably, in the uses, methods or kits of the invention, the pharmaceutical composition is to be administered to a human patient.

The success of the bispecific single chain antibody therapy may be monitored by established standard methods for the respective disease entities:
For B cell leukaemia therapy e.g. white blood cell counts, differentials, Fluorescence Activated Cell Sorting (FACS), bone marrow aspiration and various leukemia specific clinical chemistry parameters and other established standard methods may be used. For B cell lymphoma therapy e.g. computer-aided tomography, X-ray, nuclear magnetic resonance tomography (e.g. for National Cancer Institute-criteria based response assessment (Cheson (1999), J. Clin. Oncol.; 17(4):1244), positron-emission tomography scanning, white blood cell counts, differentials, Fluorescence Activated Cell Sorting, bone marrow aspiration, lymph node biopsies/histologies, and various lymphoma specific clinical chemistry parameters (e.g. lactate dehydrogenase) and other established standard methods may be used.

Cytotoxicity can be detected by methods known in the art and methods as illustrated herein below and in the appended examples.

BRIEF DESCRIPTION OF THE DRAWINGS

FIG. 12: Bone marrow histopathology of Patient #102003 before and after 2 weeks of treatment with the bscCD19× CD3.

Left panel before treatment with the bscCD19×CD3: The bone marrow shows 40-50% bone marrow infiltration by small lymphocytic lymphoma cells. Right panel after two weeks treatment with the bscCD19×CD3: No evidence for infiltration with small lymphocytic lymphoma cells could be found any more, whereas a significant increase of T cells could be observed.

Figure 13:
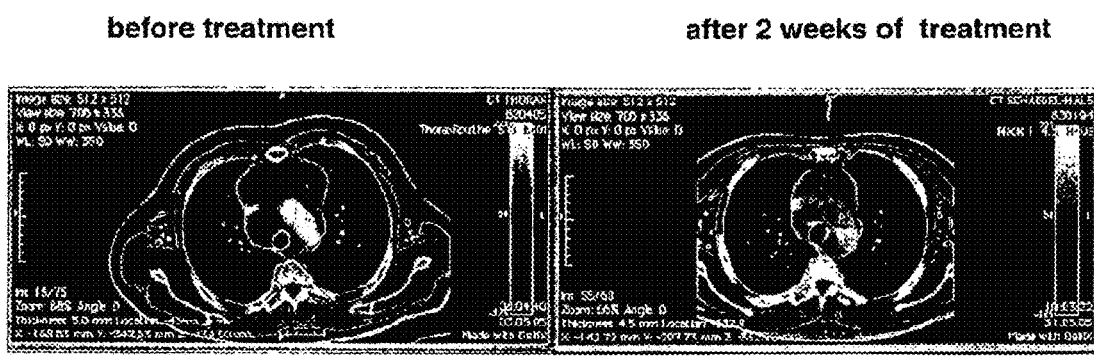

FIG. 13: (A) Size measurement of 4 mediastinal lymphoma lesions of Patient #102003 (as set forth in Table in FIG. 13(B)) before (left panel; 2 May 2005) and after (right panel; 31 May 2005) 2 weeks after treatment with the bscCD19×CD3 by computed tomography (CT). (B) Lymphoma size reduction as shown in (A) was quantified as depicted in the table shown in (B) along with two other lymphoma lesions (retroperitoneal and mesenterial) selected for efficacy assessment. Total lymphoma size reduction is expressed as percent decrease of the sum of the products of the largest cross sectional diameters (i.e. Sum Product Diameters or SPD) of the six selected lymphoma lesions. Accordingly, a lymphoma shrinkage of 57.2% could be diagnosed fulfilling the criteria of a partial response (PR).

Figure 14:
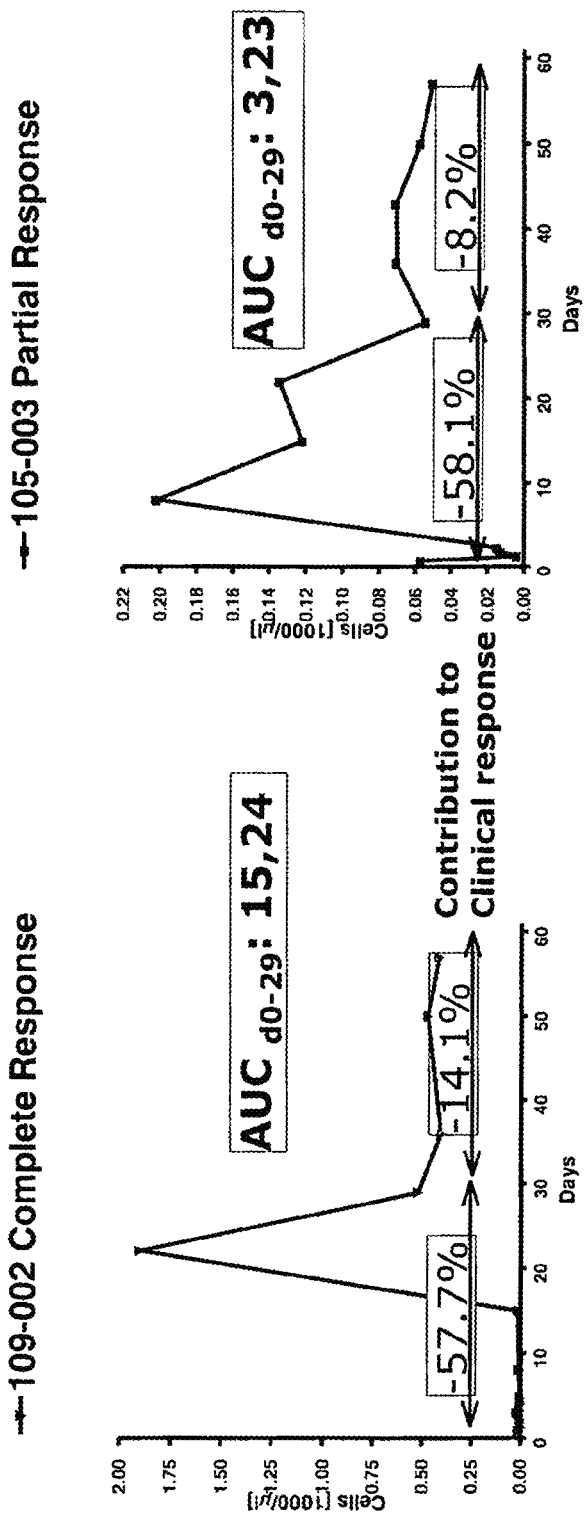

FIG. 14: CD8+ T cell expansion correlates with different clinical responses. Cell courses of the CD8+ TEM subsets are shown for 2 patients, i.e. patients #109002 (complete response) and #105003 (partial response) who reached different clinical responses. Also depicted is the contribution of the first and second 4 weeks of treatment, respectively to the overall clinical response as well as the area under the TEM subset curve (AUC) for the first 4 weeks. Maximal contribution to the clinical response of patients occurs within the first 4 weeks of treatment and correlates well with the expansion of the CD8+ TEM subset. The proliferation of these highly cytotoxic T cells seems to be a prerequisite for a clinical benefit as underlined by the observations that both the absolute cell number reached during expansion and the relative increase compared to pre-treatment levels contribute to an optimal clinical response.

Figure 15:
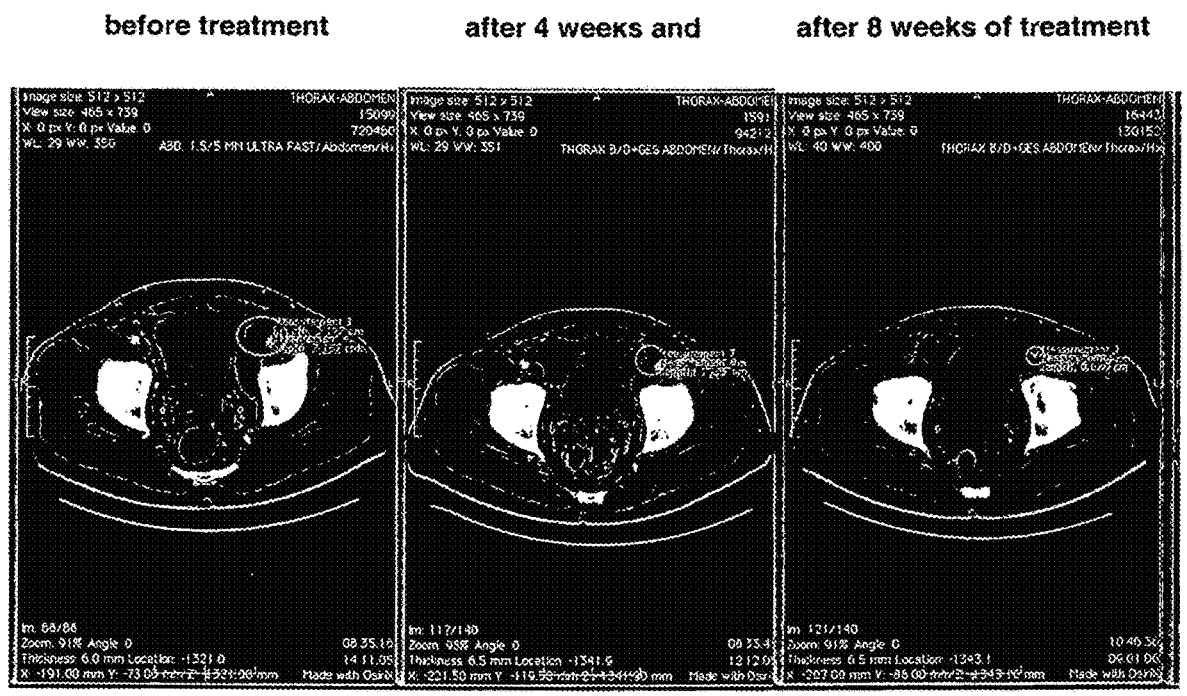

FIG. 15: Iliacal lymphoma detected by CT scan (marked by circle) in patient #109002: Size prior to anti-CD19×anti-CD3 bispecific single chain antibody treatment 3.2×2.2 cm². The same lymphoma lesion had decreased in size to 1.7×1.2 cm² after 4 weeks of continuous anti-CD19×anti-CD3 bispecific single chain antibody infusion. After 8 weeks of continuous anti-CD19×anti-CD3 bispecific single chain antibody infusion the lymphoma had disappeared i.e. the size had normalized to that of a normal lymph node (0.8×0.8 cm²).

FIG. 16: Continuous infusion of anti-CD19×anti-CD3 bispecific single chain antibody to patient #109002 normalized the size of the spleen, which was massively enlarged prior to treatment.

The invention will now be described by reference to the following examples which are merely illustrative and are not to be construed as a limitation of scope of the invention.

EXAMPLE 1

1. Construction of CD19×CD3 and CD3×CD19 Bispecific Single Chain Antibodies Comprising Various Domain Rearrangements Generally, bispecific single chain antibody molecules, each comprising a domain with binding specificity for the human CD3 antigen as well as a domain with binding specificity for the human CD19 antigen, were designed as set out in the following Table 1:

TABLE 1

Formats of bispecific single chain antibody molecules comprising anti-CD3 and anti-CD19 specificities

| Construct Number | SEQ ID Nos (nucl/prot) | Formats of protein constructs (N → C) |
|---|---|---|
| 1 | 1/2 | VL(CD19)-VH(CD19)-VH(CD3)-VL(CD3) |
| 2 | 3/4 | VH(CD19)-VL(CD19)-VH(CD3)-VL(CD3) |
| 3 | 5/6 | VH(CD3)-VL(CD3)-VH(CD19)-VL(CD19) |
| 4 | 7/8 | VH(CD3)-VL(CD3)-VL(CD19)-VH(CD19) |

The variable light-chain (VL) and variable heavy-chain (VH) domains from the HD37 hybridoma (Pezzutto, J. Immunol. 138 (1997), 2793-9) were cloned according to standard PCR methods (Orlandi, Proc. Natl. Acad. Sci. USA 86 (1989), 3833-7). cDNA synthesis was carried out with oligo dT primers and Taq polymerase. For the amplification of the anti-CD19 V domains via PCR, the primers 5' L1 (SEQ ID NO: 19) and 3' K (SEQ ID NO: 20), flanking the VL domain, and 5'H1 (SEQ ID NO: 21) and 3'G (SEQ ID NO: 22) for the heavy chain were used, based on primers described by Dübel, J. Immunol. Methods 175 (1994), 89-95. The cDNA of the anti-CD3 scFv fragment was kindly provided by Traunecker (Traunecker, EMBO J. 10 (1991) 3655-9).

Construct 1 as set out in Table 1 was generated as follows. To obtain an anti-CD19 scFv-fragment, the corresponding VL- and VH-regions cloned into separate plasmid vectors, served as templates for a VL- and VH-specific PCR using the oligonucleotide primer pairs 5'VLB5RRV (SEQ ID NO: 23)/3'V LGS15 (SEQ ID NO:24) and 5'VHGS15 (SEQ ID NO: 25)/3'VHBspE1 (SEQ ID NO: 26), respectively. Overlapping complementary sequences were introduced into the PCR-products that combined to form the coding sequence of 15-amino acid $(Gly_4Ser_1)_3$(SEQ ID NO: 46)-linker during the subsequent fusion-PCR. This amplification step was performed with the primer pair 5"VLB5RRV (SEQ ID NO: 23)/3'VHBspE1 (SEQ ID NO: 26) and the resulting fusion product (or rather anti-CD19 scFv-fragment) was cleaved with the restriction enzymes EcoRV and BspEI and thus cloned into the bluescript KS-vector (Statagene), containing the (EcoR1/Sall-cloned) coding sequence of the anti-17-1A/anti-CD3 bispecific single-chain antibody (actually the version without the Flag-tag) (Kufer, Cancer Immunol. Immunother. 45 (1997) 193). Thereby the anti-17-1A-specificity was replaced by the anti-CD19-scFV-fragment, preserving the 5-amino acid $Gly_4Ser$(SEQ ID NO: 47)-linker that connects the C-terminal anti-CD3 scFv-fragment. Subsequently, the DNA-fragment encoding the anti-CD19/anti-CD3 bispecific single-chain antibody with the domain arrangement $VL_{CD19}$-$VH_{CD19}$-$VH_{CD3}$-$VL_{CD3}$ was subcloned into the EcoR1/Sall sites of the described expression vector pEF-DHFR (Mack, Proc. Natl. Acad. Sci. USA 92 (1995), 7021-5). The resulting plasmid-DNA was transfected into DHFR-deficient CHO-cells by electroporation. The selection, gene amplification and protein production were performed as previously described (Mack, Proc. Natl. Acad. Sci. USA 92 (1995), 7021-5). The DNA sequence corresponding to construct 1 as set out above in Table 1 is as represented in SEQ ID NO: 1. The protein translation of this DNA sequence (with leader) is as represented in SEQ ID NO: 2.

The remaining constructs as set out above in Table 1 were constructed as follows. The DNA sequence corresponding to SEQ ID NO: 1 (construct 1), the protein translation of which is represented by SEQ ID NO: 2 was used as PCR template in designing the various anti-CD3/anti-CD19 single chain bispecific antibodies set out above in Table 1.

To generate a VH-VL arrangement of CD19 in position A1 and A2 (as defined in FIGS. 1A and 1B of WO2004/106381), PCR with the respective primer combination 5"VHCD19BsrGI (SEQ ID NO: 36) and 3"VHCD19GS15 (SEQ ID NO: 37) or 5"VLCD19GS15 (SEQ ID NO: 38) and 3"VLCD19BspEl (SEQ ID NO: 39) was used. During these PCR cycles overlapping complementary sequences were introduced into the PCR-products forming the coding sequence of a 15 amino acid linker during the subsequent fusion PCR. The amplified VL and VH domains were fused in a second PCR reaction (fusion PCR) in which only the outer primers, namely 5"VHCD19BsrGI (SEQ ID NO: 36) and 3"VLCD19BspEl (SEQ ID NO: 39), and both amplicons were required.

A similar procedure employing other combinations of primers was used to construct other domain arrangements. A set of appropriate primers was designed to perform multiple PCR-based cloning steps, finally resulting in the various VL-VH domain arrangements. The primer combinations used are listed in the following table:

TABLE 2

Overview of PCR-based cloning steps used for construction of positions A1 and A2 of constructs 1 to 4 as shown in Table 1

| PCR step | Primers Used | | PCR step | Used Primers | Resulting N-terminal Domain order |
|---|---|---|---|---|---|
| PCR A1 | 5'VHCD19BsrGI (SEQ ID NO: 36) | 3'VHCD19GS15 (SEQ ID NO: 37) | Fusion PCR A1 + A2 | 5'VHCD19BsrGI (SEQ ID NO: 36) | CD 19 VH-VL |
| PCR A2 | 5'VLCD19GS15 (SEQ ID NO: 38) | 3'VLCD19BspEI (SEQ ID NO: 39) | | 3'VLCD19BspEI (SEQ ID NO: 39) | |
| PCR A1 | 5'VHBsrGI (SEQ ID NO: 32) | 3'VHL2KGS15 (SEQ ID NO: 33) | Fusion PCR A1 + A2 | 5'VHL2KBsrGI (SEQ ID NO: 32) | Anti-CD3 VH-VL |
| PCR A2 | 5' VLL2KGS15 (SEQ ID NO: 34) | 3'VLL2KBspEI (SEQ ID NO: 35) | | 3'VLL2KBspEI (SEQ ID NO: 35) | |
| PCR A1 | 5'VLL2KBsrGI (SEQ ID NO: 40) | 3'VLL2KGS15 (SEQ ID NO: 41) | Fusion PCR A1 + A2 | 5'VLL2KBsrGI (SEQ ID NO: 40) | Anti-CD3 VL-VH |
| PCR A2 | 5'VHL2KGS15 (SEQ ID NO: 42) | 3'VHL2KBspEI (SEQ ID NO: 43) | | 3'VHL2KBspEI (SEQ ID NO: 43) | |

In order to change the VH-VL domain arrangement in the C-terminal position, namely positions B1 and B2 as defined in FIGS. 1A and 1B of WO2004/106381, the following primers comprising the designated restriction enzyme recognition sites were designed to perform the PCR-based cloning steps.

All molecular biological procedures indicated above were carried out according to standard protocols described in Sambrook, Molecular Cloning (A Laboratory Manual, 3rd edition, Cold Spring Harbor Laboratory Press, Cold Spring Harbor, N.Y. (2001).

TABLE 3

Overview of PCR-based cloning steps used for construction of positions B1 and B2 of constructs 1 to 4 as shown in Table 1

| PCR step | Primers used | | Resulting C-terminal domain order |
|---|---|---|---|
| PCR B1 + B2 | 5' VLCD19BspEIGS (SEQ ID NO: 31) | 3' VHCD19BspEI (SEQ ID NO: 44) | CD 19 VL-VH |
| | 5' VHCD19BspEIGS (SEQ ID NO: 29) | 3'VLCD19BspEI (SEQ ID NO: 30) | CD19 VH-VL |
| | 5' VLL2KBspEIGS (SEQ ID NO: 27) | 3'VHL2KBspEI (SEQ ID NO: 28) | Anti-CD3 VL-VH |

The corresponding PCR product, which was flanked by two BspEI sites, was cloned into a plasmid designated BS-CTI, which was digested with BspEI and XmaI restriction enzymes. A polylinker designated CTI (SEQ ID NO: 45) was inserted before into the Bluescript KS vector (GenBank accession number X52327) using the restriction enzyme cleavage sites XbaI and SalI in order to provide additional cleavage sites as well as the sequence encoding a G$_4$S(SEQ ID NO: 47)-linker, six consecutive histidine residues and a stop codon. During this cloning step the BspEI site of the VH domain was fused with the XmaI site of the plasmid thereby destroying both sites. The correct orientation of the variable domain was verified by sequencing according to standard protocols.

DNA encoding the bispecific single chain antibodies in Table 1 (SEQ ID NOs: 1, 3, 5, 7) were transfected into DHFR deficient CHO cells for eukaryotic protein expression in DHFR deficient CHO cells as described in Mack et al. (Mack, Proc Natl Acad Sci USA 92 (1995), 7021-25). Gene amplification of the construct was induced by increasing concentrations of methotrexate (MTX) up to a final concentration of 20 nM MTX. The transfected cells were then expanded and 1 liter of supernatant produced.

2. Expression and Purification of the Bispecific Single Chain Antibodies Directed Against CD3 and CD19

The bispecific single chain antibodies were expressed in Chinese hamster ovary cells (CHO). Transfection of the expression vector was performed following calcium phosphate treatment of the cells ("Molecular Cloning", Sambrook et. al. 1989). The cells were grown in roller bottles with CHO modified DMEM medium (HiQ®, HiClone) for 7 days before harvest. The cells were removed by centrifugation and the supernatant containing the expressed protein was stored at −20° C.

Äkta® FPLC System (Pharmacia) and Unicorn® Software were used for chromatography. All chemicals were of research grade and purchased from Sigma (Deisenhofen) or Merck (Darmstadt). Immobilized metal affinity chromatography ("IMAC") was performed using a Fractogel® column (Merck) which was loaded with $ZnCl_2$ according to the protocol provided by the manufacturer. The column was equilibrated with buffer A2 (20 mM sodium phosphate buffer pH 7.5, 0.4 M NaCl) and the cell culture supernatant (500 ml) was applied to the column (10 ml) at a flow rate of 3 ml/min. The column was washed with buffer A2 to remove unbound sample. Bound protein was eluted using a 2 step gradient of buffer B2 (20 mM sodium phosphate buffer pH 7.5, 0.4 M NaCl, 0.5 M Imidazol) according to the following:

Step 1: 20% buffer B2 in 6 column volumes;
Step 2: 100% buffer B2 in 6 column volumes.
Eluted protein fractions from step 2 were pooled for further purification.

Gel filtration chromatography was performed on a Sephadex S200 HiPrep column (Pharmacia) equilibrated with PBS (Gibco). Eluted protein samples (flow rate 1 ml/min) were subjected to standard SDS-PAGE and Western Blot for detection. Prior to purification, the column was calibrated for molecular weight determination (molecular weight marker kit, Sigma MW GF-200). Protein concentrations were determined using protein assay dye (MicroBCA, Pierce) and IgG (Biorad) as standard protein.

The bispecific single chain antibodies were isolated in a two step purification process of IMAC and gel filtration. The main product had a molecular weight of ca. 52 kDa under native conditions as determined by gel filtration in PBS. This molecular weight corresponds to the bispecific single chain antibody. All constructs were purified according to this method.

Purified bispecific single chain antibody protein was analyzed in SDS PAGE under reducing conditions performed with pre-cast 4-12% Bis Tris gels (Invitrogen). Sample preparation and application were performed according to the protocol provided by the manufacturer. The molecular weight was determined with MultiMark protein standard (Invitrogen). The gel was stained with colloidal Coomassie (Invitrogen protocol). The purity of the isolated protein was >95% as determined by SDS-PAGE.

Western Blot was performed using an Optitran® BA-583 membrane and the Invitrogen Blot Module according to the protocol provided by the manufacturer. The antibodies used were directed against the His Tag (Penta His, Qiagen) and Goat-anti-mouse Ig labeled with alkaline phosphatase (AP) (Sigma), and BCIP/NBT (Sigma) as substrate. The bispecific single chain antibody could be specifically detected by Western Blot. A single band was detected at 52 kD corresponding to the purified bispecific molecule.

3. Flow Cytometric Binding Analysis of CD19×CD3 Specific Polypeptides

In order to test the functionality of the constructs with regard to binding capability to CD19 and CD3, FACS analysis was performed. For this purpose CD19 positive NALM-6 cells (human B cell precursor leukemia) and CD3 positive Jurkat cells (human T cell leukemia) were used. 200,000 NALM-6 cells and 200,000 Jurkat cells were respectively incubated for 30 min on ice with 50 µl of the pure cell supernatant of CHO cell cultures each expressing bispecific antibodies with different arrangements of VH and VL domains of CD19 and CD3 (as described in section 2, supra). The cells were washed twice in PBS and binding of the construct was detected as follows. The cells treated as described above were contacted with an unlabeled murine Penta His antibody (diluted 1:20 in 50 µl PBS with 2% FCS; Qiagen; Order No. 34660), which specifically binds to cell-bound construct via the construct's C-terminal histidine tag. A washing step followed to remove unbound murine Penta His antibody. Bound anti His antibodies were detected with an Fc gamma-specific antibody (Dianova) conjugated to phycoerythrin, diluted 1:100 in 50 µl PBS with 2% FCS. As a negative control fresh culture medium was used in place of culture supernatant.

Cells were analyzed by flow cytometry on a FACSCalibur apparatus (Becton Dickinson, Heidelberg). FACS staining and measuring of the fluorescence intensity were performed as described in Current Protocols in Immunology (Coligan, Kruisbeek, Margulies, Shevach and Strober, Wiley-Interscience, 2002). The binding ability of several domain arrangements were clearly detectable as shown in WO2004/106381. In FACS analysis all constructs with different arrangement of VH and VL domains specific for CD19 and CD3 showed binding to CD3 compared to the negative control using culture medium and 1. and 2. detection antibody. Strong binding activity resulting in a shift in fluorescence intensity $>5 \times 10^1$ was observed for the constructs referred to in Table 1.

4. Bioactivity of Bispecific Single Chain Antibodies Specific for CD19 and CD3

Cytotoxic activity of the bispecific antibodies with rearranged VH and VL domains was determined in a fluorochrome release based cytotoxicity assay. CD19 positive NALM-6 cells were used as target cells ($1.5 \times 10^7$) labeled with 10 µM calcein AM (Molecular Probes, Leiden, Netherland, no. C-1430) for 30 min at 37° C. in cell culture medium. After two washes in cell culture medium, cells were counted and mixed with the CD4-positive T cell clone CB15 cells (kindly provided by Dr. Fickenscher, University of Erlangen/Nuernberg, Germany). $2 \times 10^6$ CB15 cells and $2 \times 10^5$ NALM-6 cells were mixed per ml (E:T ratio of 1:10) and 50 µl of this suspension was used per well in a 96 well round bottom plate. Antibodies were diluted in RPMI/10% FCS to the required concentration and 50 µl of this solution was added to the cell suspension. A standard reaction was incubated at 37° C./5% $CO_2$ for 2 hours. After the cytotoxic reaction, the released dye in the incubation medium can be quantitated in a fluorescence reader (Tecan, Crailsheim, Germany) and compared with the fluorescence signal from a control reaction (without bispecific antibody), and the fluorescence signal obtained for totally lysed cells (for 10 min in 1% saponin). On the basis of these readings, the specific cytotoxicity was calculated according to the following formula: [Fluorescence (Sample)−Fluorescence (Control)]: [Fluorescence (Total Lysis)−Fluorescence (Control)]×100.

Sigmoidal dose response curves typically had $R^2$ values >0.97 as determined by Prism Software (GraphPad Software Inc., San Diego, USA). $EC_{50}$ values calculated by the analysis program were used for comparison of bioactivity.

As shown in WO2004/106381, all constructs revealed cytotoxic activity against CD19 expressing NALM-6 cells.

Strongest bioactivity with EC 50 values<500 pg/ml was detected for the constructs shown in Table 1, supra.

EXAMPLE 2

Clinical Use of bscCD19×CD3 in a Patient with B-Cell Lymphoma

In a compassionate use, a patient (female, born 1937) suffering from B-cell derived chronic lymphatic leukemia (B-CLL) has been treated with the bispecific single chain antibody bscCD19×CD3 (SEQ ID NO. 2) as described in detail in WO 99/54440. FACS analysis revealed that 95% of the patient's peripheral blood cells were CD19 positive cells while 77% of the cells expressed the CD20 antigen. Incubation of the patient's peripheral blood cells with the bscCD19×CD3 showed a pronounced depletion of CD19-positive B-cells. To prevent any acute cytokine reactions and complications of tumor lysis, the patient got prophylactic IV doses of 2 mg clemastine (Tavegil®) and 200 mg cimetidine (Tagamet®) as well as 300 mg allopurinol and 20 mg of omeprazole (Antra®).

The patient received a first dose of 3 µg bscCD19×CD3 as 20 min-infusion in isotonic phosphate buffer containing 5% human serum albumin (HSA). During the infusion the patient did not have any adverse effects. About 1 hour after infusion the patient had chills for about 5 minutes followed by sweating, a moderate decrease of blood pressure by about 10 mm Hg and a moderate increase of body temperature (+0.5° C.) for a few hours. In addition, her headache slightly worsened. The patient was treated with another 2 mg of Tavegil® and 200 mg of Tagamet®, 250 mg prednisolone (Solu-Decortin®) and 50 mg pethidine (Dolantin®). All symptoms released without sequelae the same day.

A second dose of 10 µg bscCD19×CD3 was given one day later under the same conditions referred to above. About 1 hour after infusion the patients had remarkable chills, fever (39.2° C.), slight hyperventilation and a hypotensive reaction. The patient was treated with 2 mg Tavegil, 200 mg Tagamet and 300 mg Solu-Decortin and 15 mg piritramide (Dipidolor®). For stabilization of her cardiovascular function the patient received a dopamine infusion and got volume substitution. Following this treatment the symptoms decreased remarkably.

During the next 3 days the patient continued having subfebrile temperature (about 37.2° C.) and developed minor pleural effusion one day later the second dose and mild edema of the lower extremities.

Ultrasound examination of the spleen and five abdominal and axillary lymph nodes was performed one day and 4 days after administration of the second dose of bscCD19×CD3. Already one day after the 10 µg dose, the lymph nodes as well as the spleen showed a shrinkage of about 20% as compared to the size of the lymph nodes and spleen prior to treatment. This observation was confirmed in a second ultrasound evaluation. The weight of the spleen decreased by 350 g (from 1630 g prior to treatment to 1280 g after treatment).

The number of white blood cells, which include mostly malignant B-cells, decreased during the course of the treatment and the follow-up days. The C-reactive protein (CRP) is an acute phase reaction protein which reflects T-cell activation and the effect of pro-inflammatory cytokines. It increased remarkably after administration of 10 µg bscCD19×CD3, followed by a continuous decrease during the next 3 observation days.

The level of serum cytokines which reflects the acute immunological response to the administration of the compound, was measured before and at various intervals after administration of the compound. Serum levels of cytokines were measured by a quantitative ELISA assay according to the instructions of the manufacturer. Tumor necrosis factor TNF-α increased significantly in a dose-dependent manner within the first hour after administration of bscCD19×CD3. Interleukin 6 (IL-6) and interleukin 8 (IL-8) also showed a significant and dose dependent increase. Their maximum levels were observed 2 to 4 hours after administration of the bscCD19×CD3.

As a conclusion, bscCD19-CD3 was administered safely to a patient suffering from refractory B-CLL. Although adverse side effects most probably due to cytokine release have been observed, the tolerability of the bscCD19×CD3 at the doses of 3 µg and 10 µg was acceptable and could be controlled well by means of prophylactic measures and symptomatic treatment. Importantly, bscCD19×CD3 caused a shrinkage of the previously enlarged spleen and lymph nodes of the patient, as shown in ultrasound examination. Since enlargement of spleen and lymph nodes is caused by infiltrations with malignant B-cells, the shrinkage reflects the destruction of malignant B-cells as result of administration of bscCD19×CD3.

EXAMPLE 3

Dose Escalation Phase I Study

Patient 0202

The purpose of this dose escalation phase I study was to investigate the dose-dependency of changes in immunological activity in tumor target tissue of patients with relapsed B-cell Non-Hodgkin's lymphoma (NHL). To this end, each patient was scheduled to receive six intravenous administrations of an anti-CD19×anti-CD3 bispecific antibody (SEQ ID NO.2; see also WO 99/54440), over 4 hours in a once- or twice-weekly treatment schedule at day 0, 2, 7, 9, 14 and 16. The dose of anti-CD19×anti-CD3 was escalated intra-individually at the following doses: 1, 2, 4, 7, 10 and 13 µg/m² body surface area.

To assess the influence of escalated bscCD19×CD3 doses on the number and distribution of circulating lymphocyte subsets whole blood samples before and during administration were collected. The total number of lymphocytes was determined by differential blood count analysis and the number of lymphocyte subpopulations determined by FACS analysis and expressed as percentage of total lymphocytes, as described in Example 2. In particular, CD3+, CD4+ and CD8+ T cell numbers in peripheral blood mononuclear cells have been determined by fluorescence-activated cell sorter (FACS).

Figure 1:
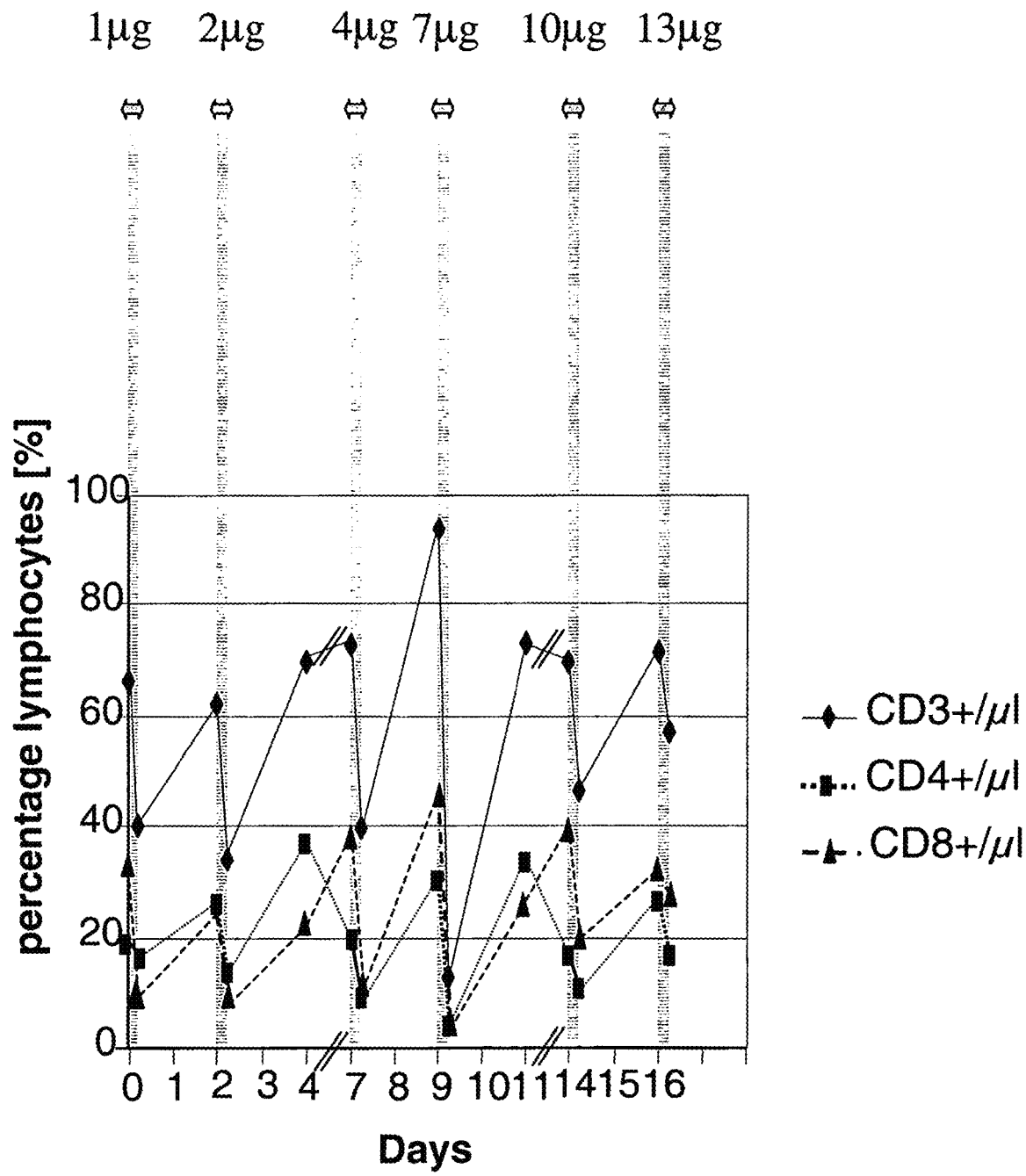
FIG. 1: Dose escalation study of intravenous anti-CD19× anti-CD3 bispecific single chain antibody (bscCD19×CD3) administered to a patient with relapsed B-cell Non-Hodgkin's lymphoma (B NHL)—effect on counts of peripheral CD3+, CD4+ and CD8+ lymphocytes. Patient 0202 diagnosed with relapsed B-cell NHL received six intravenous administrations of bscCD19×CD3, over 4 hours in a twice-weekly treatment schedule. The dose of bscCD19×CD3 was escalated at the following doses: 1, 2, 4, 7, 10 and 13 µg/m$^2$ body surface area. The number of CD3+ T lymphocytes (grey diamonds), CD4+ T lymphocytes (black squares) and CD8+ T lymphocytes (black triangles) indicated as percentage of total lymphocyte number was determined by flow cytometry before and at the end of the 4 hr infusion at days 0, 2, 7, 9, 14 and 16, respectively. The 4 hr-infusion periods are indicated by arrows and grey bars.
Figure 2:
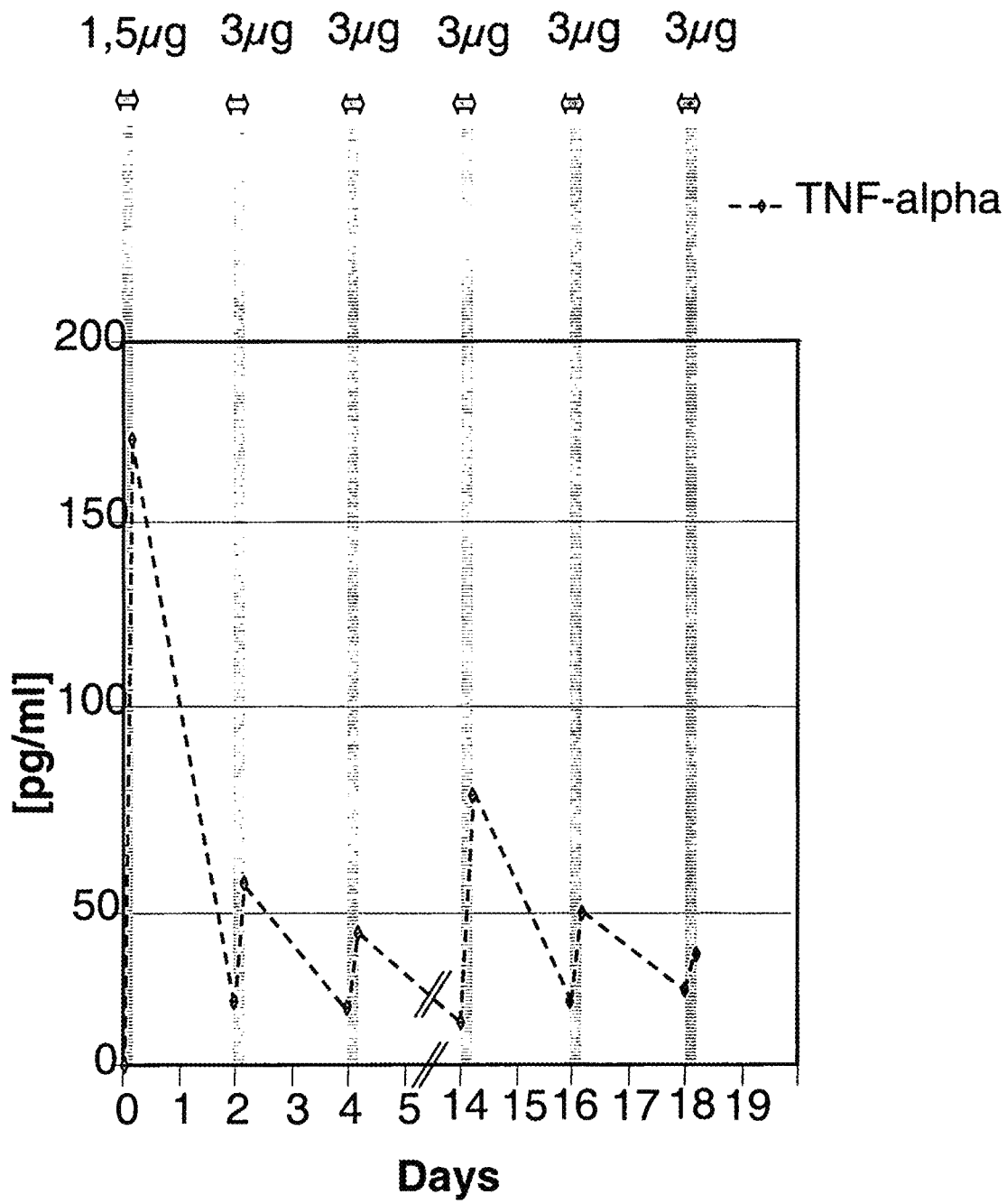
FIG. 2: Dose escalation study of intravenous anti-CD19× anti-CD3 bispecific single chain antibody (bscCD19×CD3) administered to a patient with a refractory B cell malignancy—effect on TNF alpha-serum concentrations. Patient 1003 diagnosed with a mantle cell lymphoma (MCL) received six infusions of 1.5 (initial dose at day 0) and 3 µg (maintenance dose at the following study days) bscCD19× CD3, over four hours, on study days 0, 2, 4, 14, 16 and 18. Serum concentrations of TNF alpha were determined before and after the 4 hr-infusion period. The 4 hr-infusion periods are indicated by arrows and grey bars.
Figure 3:
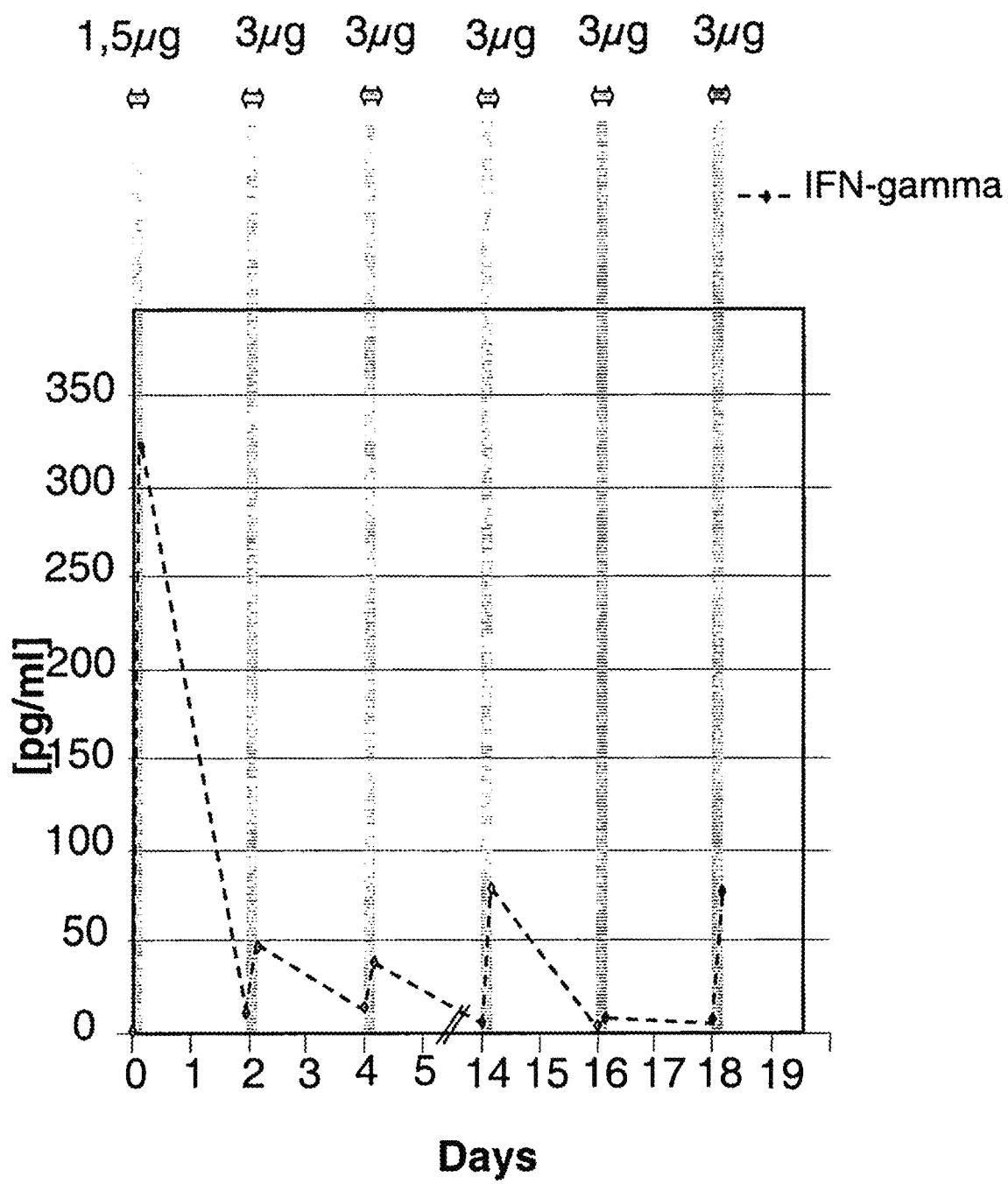
FIG. 3: Dose escalation study of intravenous bscCD19× CD3 administered to patient 1003 as indicated in the legend for FIG. 2—effect on IFN gamma-serum concentrations.
Figure 4:
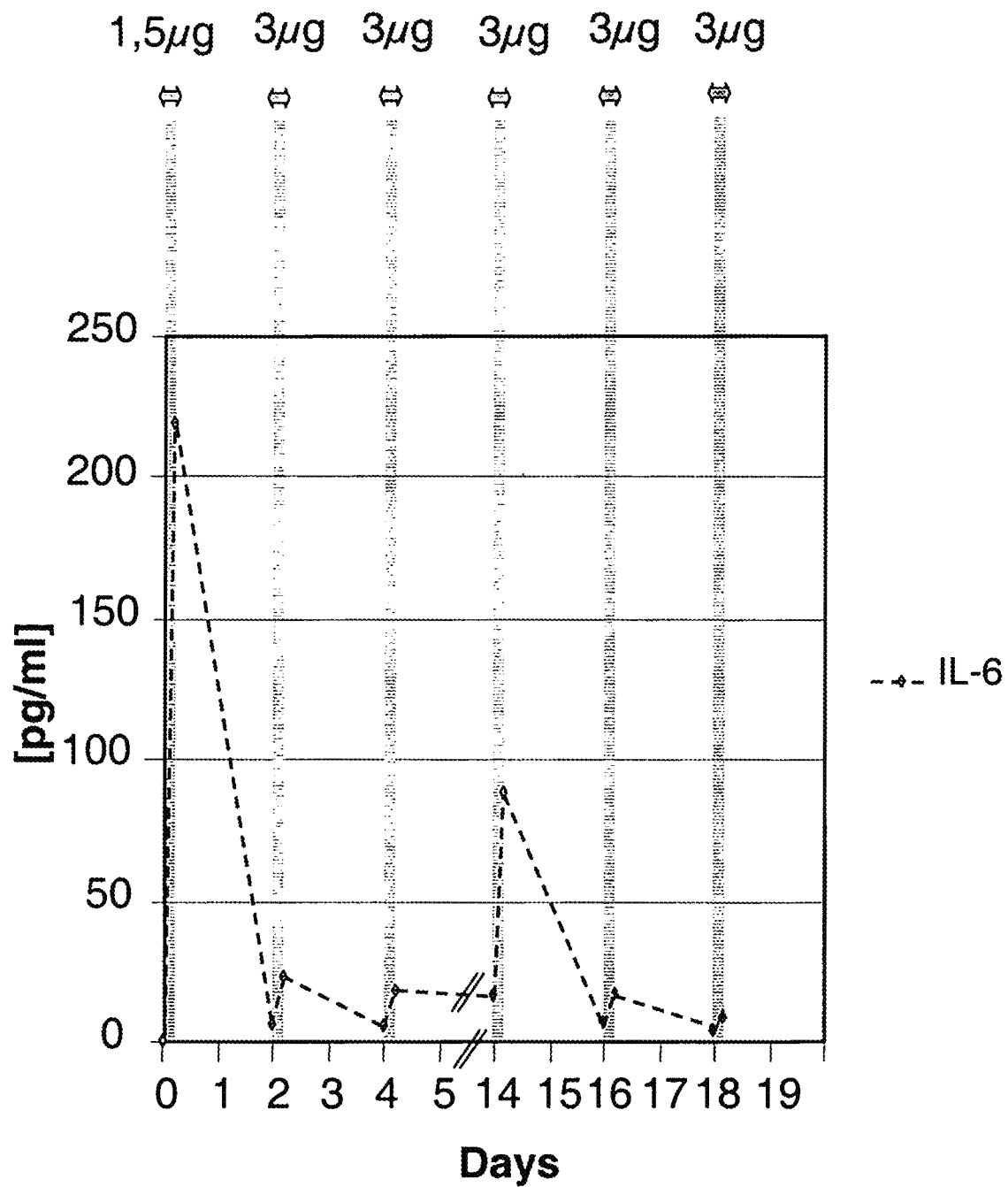
FIG. 4: Dose escalation study of intravenous bscCD19× CD3 administered to patient 1003 as indicated in the legend for FIG. 2—effect on IL6-serum concentrations.
Figure 5:
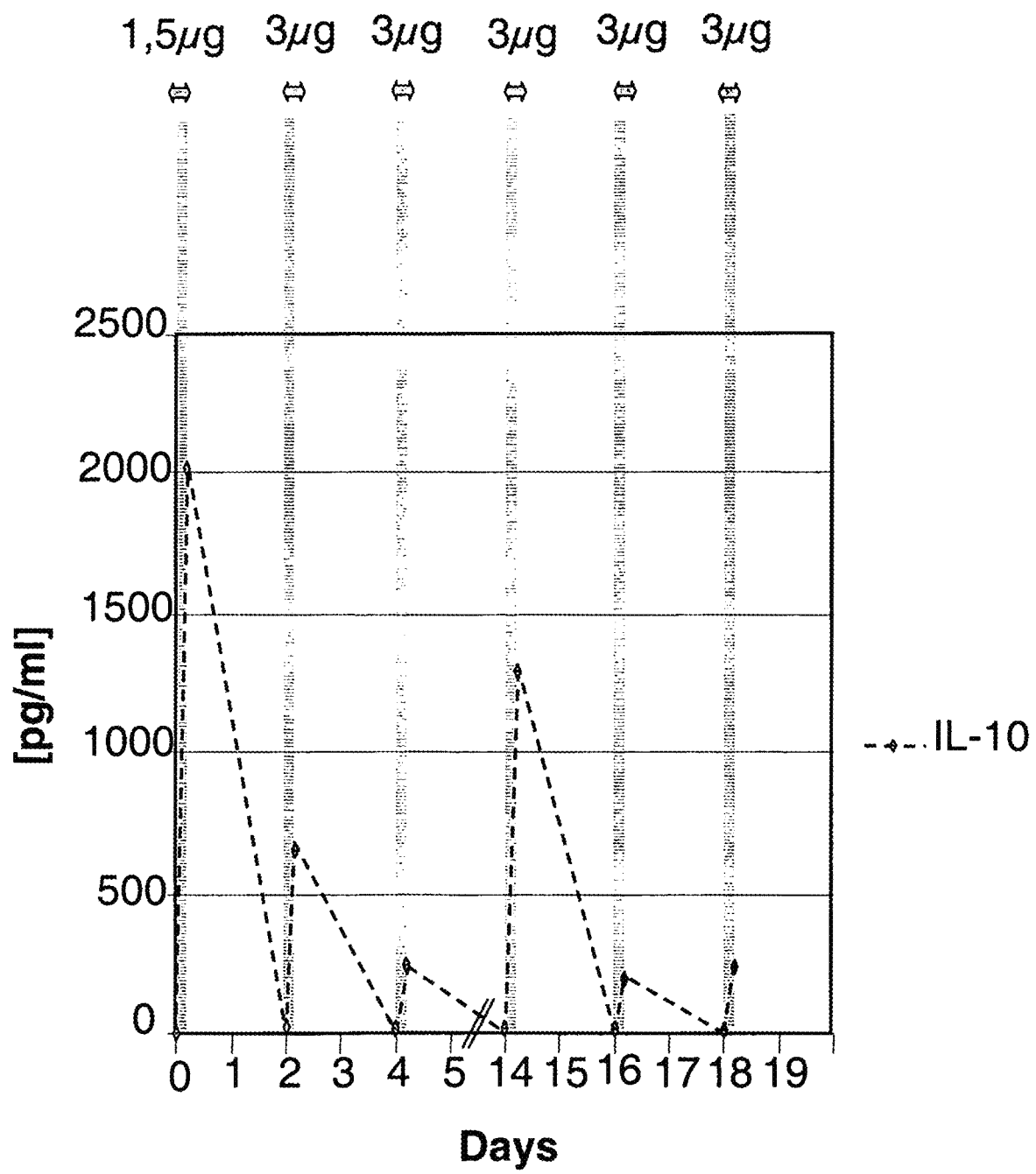
FIG. 5: Dose escalation study of intravenous bscCD19× CD3 administered to patient 1003 as indicated in the legend for FIG. 2—effect on IL10-serum concentrations.

As exemplified in FIG. 1 for one patient (i.e. patient 0202) who completed the drug treatment phase, even with the lowest starting dose of bispecific antibody, a sudden drop in CD3+, CD4+ and CD8+ T cell numbers (shown as percentage of total lymphocyte number) has been observed within the 4 hr-infusion period. The T cell numbers recovered to approximately predose values by 24 to 48 hrs. A similar curve progression of T cell counts has been observed in the other patients enrolled in this study. One explanation for this drop is the sudden adhesion and—at least partial—migration of T cells and other activated leukocytes to tissues. It is hypothesized that such a sudden activation and shifting of enormous activated T cell populations (approximately 80% of the human T cell pool reside in the peripheral blood at any time) results in a disturbance of T cell homeostasis as well as disrupting local cytokine profiles in tissues. Indeed, drug administration to the patients according to the mode shown in FIG. 1 led to adverse side effects. This result suggested that a more gradual activation and shifting of T cell populations may be closer to a physiologic immune response and may avoid phenomena such as sudden disturbance of local cytokine networks and adverse side effects resulting therefrom.

EXAMPLE 4

Clinical Trial Phase I

Patient 1003

In a further clinical trial, the safety profile of repeated intravenous infusion of the bispecific single chain anti-CD19×anti-CD3 antibody (SEQ ID NO.2; see also WO 99/54440), the maximum tolerated dose and the optimal biological dose was tested in patients with refractory indolent or aggressive B cell non-Hodgkin lymphoma (B NHL) or B cell leukemia. Each patient received six infusions of anti-CD19×anti-CD3, over two or four hours, on study days 0, 2, 4, 14, 16 and 18. A total of 15 patients were treated with doses up to 3.0 µg/m$^2$.

Blood samples were taken at different time points before and during administration of the drug to follow biochemical, haematological and immunological parameters. T cell numbers have been determined as described. In addition, using enzyme-linked immunosorbent assay (ELISA) and cytometric bead array (CBA), the serum levels of cytokines of the patients have been determined.

When monitoring T cell numbers in the treated patients, robust fluctuations of T cell numbers have been found upon each infusion, suggesting a short-term, burst-like T cell activation as also observed in previous studies; see Example 3. Moreover, as shown in FIGS. 2 to 5 for one patient (i.e. patient 1003) diagnosed with a mantle cell lymphoma (MCL), upon infusion of the bispecific antibody, a robust cytokine release of TNF alpha, Interferon gamma, Interleukin-6 and Interleukin-10 has been found in the treated patients. Cytokine release intensity was highest upon administration of the first dose, with decreasing response to subsequent infusions of bispecific anti-CD19×anti-CD3 antibody (first dose effect). After 6 infusions, almost no induction of cytokine levels has been observed. As in the study shown in Example 3, the abrupt T cell activation and cytokine release led to adverse side effects in the patients. Most of these events were of mild or moderate severity, and all transient. The most frequent laboratory abnormalities were seen in various hematologic and coagulation parameters, also being transient, and mostly mild to moderate in nature and clinical significance. The results obtained in this study suggest that a more gradual T cell activation may be necessary to avoid phenomena such as sudden disturbance of local cytokine networks observed in the above described clinical trial.

EXAMPLE 5

1. Study for Continuous Infusion Treatment of Non-Hodgkin'S Lymphoma (B NHL) Patients with Anti-CD19×Anti-CD3 Bispecific Single Chain Antibody (SEQ ID NO. 2)

In order to evaluate safety and tolerability of the anti-CD19×anti-CD3 bispecific single chain antibody (bscCD19×CD3; amino acid sequence shown in SEQ ID NO:2), the compound has been administered by long-term continuous infusion. Two patients with relapsed B cell non-Hodgkin's lymphoma (B NHL) are shown in the following sections 2 and 3 (patient #105003 and patient #102003). At the first day of treatment, the two patients received an "initial exposure dose" of 5 µg/m$^2$/24 h of anti-CD19×anti-CD3 bispecific antibody as a continuous intravenous (i.v.) infusion. Thereafter, the dosage was increased to a "maintenance dose" of 15 µg/m$^2$/24 h which was administered as a continuous intravenous infusion for the remaining infusion period of 2 (for patient #102003) or 4 weeks (for patient #105003). The daily dose of investigational drug was administered in 500 ml isotonic NaCl solution containing 5% HSA. Each of the patients received co-therapy with a glucocorticosteroid (methylprednisolone) at a concentration of 1×100 mg (i.v.) 1 h prior to the start of infusion of bispecific antibody in order to suppress cytokine release at the initial phase of the infusion period.

Section 4 of this Example 5 provides for further summarizing data of patients treated with an "initial exposure dose" (between 0.5 and 5 µg/m$^2$/24 h) and "maintenance dose" of 15 µg/m$^2$/24 h).

2. Patient #105003 Diagnosed with Follicular Lymphoma (B Cell Non-Hodgkin Lymphoma)

This 44-year old male patient was diagnosed with a follicular lymphoma in 2000. The patient had previously received multiple chemotherapies (CHOP; Bendamustin) and immunotherapies (Rituximab; anti-CD20 monoclonal antibody). After participation for 2 years in a vaccination trial, the disease once more progressed. In autumn 2005, the patient experienced an increasing bone marrow infiltration, resulting in anemia, and infiltration of the lung with impairment of the respiratory function. Furthermore, the quality of life of this patient was clearly reduced due to a worsening of the B-symptomatic (splenomegaly, increased night sweating and a 3 kg weight loss over 3 weeks). This clinical condition made a new therapy necessary.

In the following, the patient received the anti-CD19×anti-CD3 bispecific single chain antibody (SEQ ID NO.2) at a dose level of 15 µg/m$^2$/24 h as a continuous infusion for 4 weeks as detailed above. The treatment was started on 3 Mar. 2005 and well tolerated, i.e. no significant adverse side effects could be observed.

2.1 T Cell Activation and Proliferation by the Anti-CD19× Anti-CD3 Bispecific Single Chain Antibody Mononuclear cells from samples of peripheral blood obtained from patient #105003 at different time points according to the study protocol were analyzed by 4-color flowcytometry after staining with the following combinations of 4 different antibodies or surface markers:

Panel 1: CD2×CD3×CD4×CD8 (T cells)
Panel 2: CD3×CD16×CD19×CD56 (lymphocyte counts: B, T and NK cells)
Panel 3: CD8×CD25×CD69×HLA-DR(CD8$^+$ T cell activation)
Panel 4: CD8×CD28×CD45RA×CCR7 (CD8$^+$ T cell subsets)

Absolute cell counts of lymphocyte subsets i.e. B, T and NK cells defined as CD19$^+$/CD3$^-$, CD3$^+$ and CD3$^-$/CD56$^+$ cells, respectively, were calculated from panel 2 as % (B, T or NK cells)/(% B+% T+% NK cells) multiplied with the total lymphocyte counts of the respective blood sample as determined by a routine laboratory. Absolute CD4$^+$ and CD8$^+$ T cell counts were calculated from panel 1 as % CD3$^+$CD4$^+$CD8$^-$ cells/% CD3$^+$ cells or % CD3$^+$CD4$^-$CD8$^+$ cells/% CD3$^+$ cells, respectively, multiplied with absolute T cell counts as calculated from panel 2. Absolute cell counts of CD8+ T cell subsets were calculated from the following ratios of percentages obtained from panel 4 each multiplied with absolute CD8+ T cell counts as calculated from panel 2:

% $CD8^+CD45RA^+CD28^+$ cells/% $CD8^+$ cells(corresponding to naïve $CD8^+T$cells), % $CD8^+CD45RA^-CCR7^+$ cells/% $CD8^+$ cells(corresponding to central memory $CD8^+T$cells=$T_{CM}$), % $CD8^+CD45RA^-CCR7$ cells/% $CD8^+$ cells(corresponding to effector memory $CD8^+T$cells=$T_{EM}$), and $CD8^+CD45RA^+CD28^-$ cells/% $CD8^+$ cells(corresponding to terminally differentiated $CTL$(cytotoxic $T$cells)=$CD45RA$-positive effector memory $CD8^+T$cells=$T_{EMRA}$).

T cell activation in this patient was determined as % CD8+ T cells expressing the cell surface activation markers CD25, CD69 or HLA-DR (flowcytometry panel 3) of all CD8+ T cells.

Figure 6:
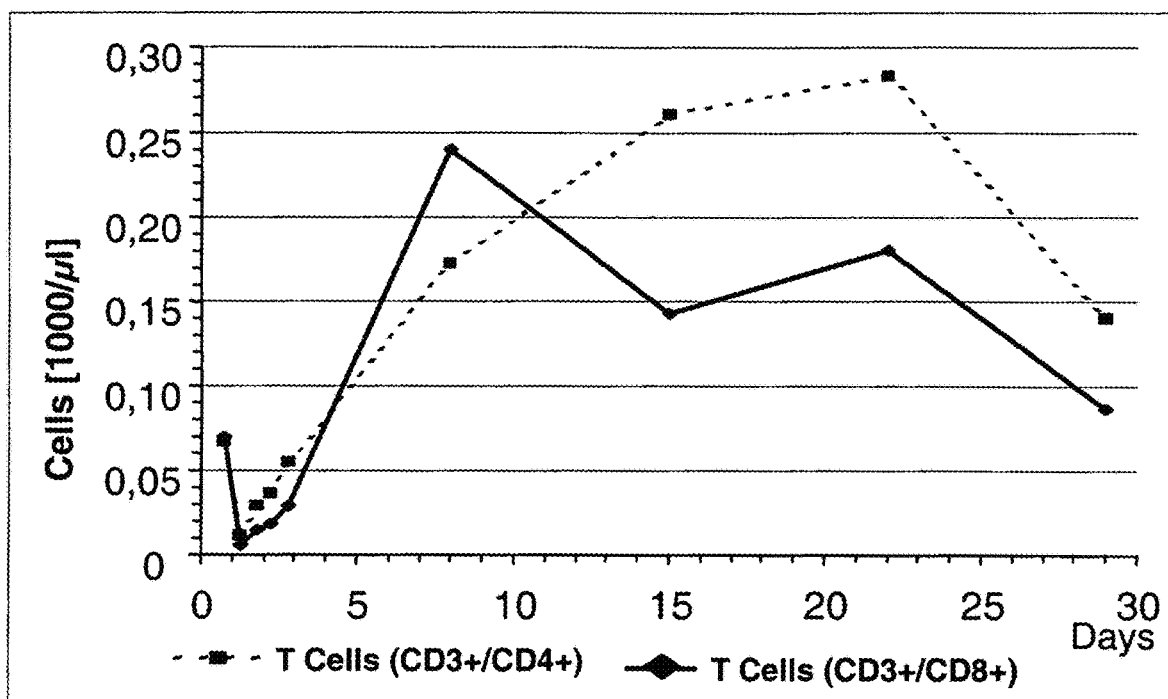
FIG. 6: Analysis of $CD3^+/CD8^+$ and $CD3^+/CD4^+$ T cell counts. $CD8^+$ and $CD4^+$ T cells largely disappeared from peripheral blood after start of infusion of the bscCD19× CD3, which is explained as distributional phenomenon triggered by T cell activation through crosslinking mediated by the bscCD19×CD3 of peripheral blood T and B cells. However, after half a week of treatment, $CD8^+$ and $CD4^+$ T cells reappeared in the blood and further increased in numbers until day 7 and 21, respectively. Compared to their starting values $CD8^+$ and $CD4^+$ T cells showed a 3.5- to 4-fold expansion in the blood. $CD8^+$ and $CD4^+$ T cell counts stayed high during treatment weeks 2 and 3, before T cell numbers started to decrease during the fourth week of treatment. $CD8^+$ and $CD4^+$ T cell counts were still above the corresponding pretreatment values after 4 weeks of infusion of the bscCD19×CD3, when substantial tumor shrinkage was diagnosed fulfilling the criteria of a partial response.

First, CD4+ and CD8+ T cell counts have been analysed. As shown in FIG. 6, CD8+ and CD4+ T cells largely disappeared from peripheral blood after start of infusion of the anti-CD19×anti-CD3 bispecific single chain antibody, which is explained as distributional phenomenon triggered by T cell activation through crosslinking of peripheral blood T and B cells mediated by the anti-CD19×anti-CD3 bispecific single chain antibody. However, after half a week of treatment, CD8+ and CD4+ T cells reappeared in the blood and further increased in numbers until day 7 and 21, respectively. Compared to their starting values, CD8+ and CD4+ T cells showed a 3.5- to 4-fold expansion in the blood. CD8+ and CD4+ T cell counts stayed high during treatment weeks 2 and 3, before T cell numbers started to decrease during the fourth week of treatment. CD8+ and CD4+ T cell counts were still above the corresponding pre-treatment values after 4 weeks of infusion of the anti-CD19×anti-CD3 bispecific single chain antibody, when substantial tumor shrinkage was diagnosed fulfilling the criteria of a partial response, as set forth below.

Figure 7:
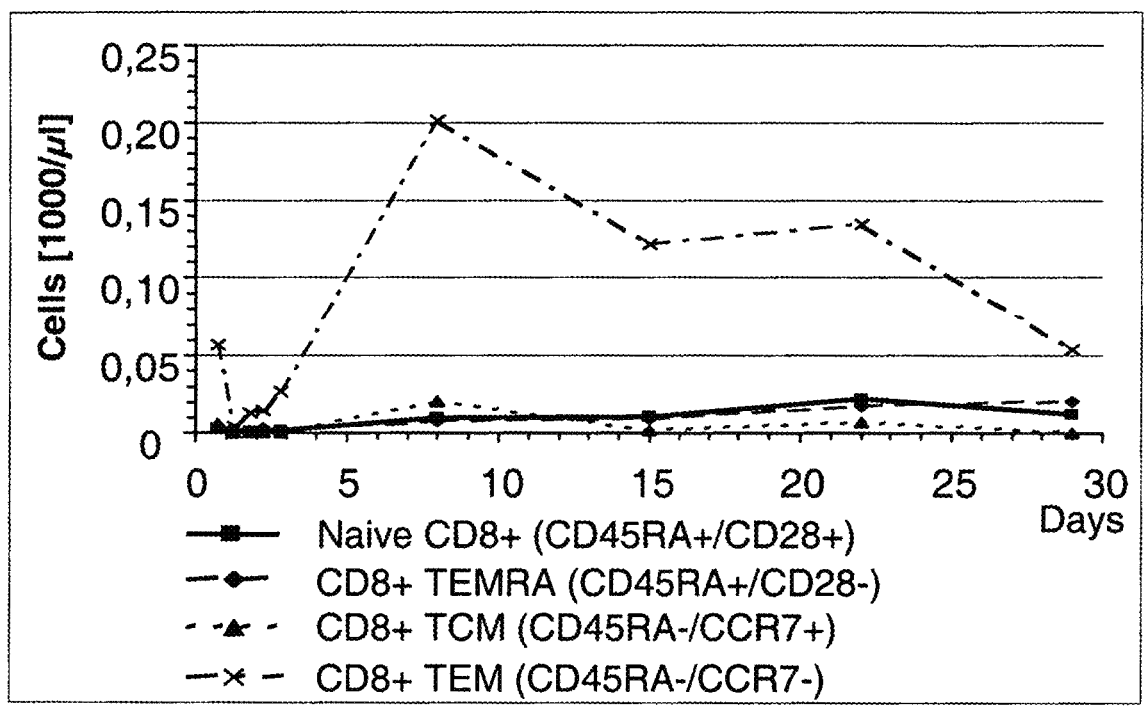
FIG. 7: Analysis of $CD8^+$ T cell subpopulations. The effector memory subset TEM was almost exclusively responsible for the expansion of $CD8^+$ T cells induced by the bscCD19×CD3. $CD8^+$ T cells account for most of the cytotoxic activity among all T cells and the TEM-cells together with the TEMRA-subset account for most of the cytotoxic activity among the $CD8^+$ T cells. Except for the TEM-subset, no significant changes in cell counts could be observed among the other $CD8^+$ T cell subpopulations like the naïve T cells not capable of proliferating upon a single activation signal as provided by the bscCD19×CD3 or the TEMRA-subset not capable of proliferating at all. Thus, the selective expansion of the proliferation-competent $CD8^+$ TEM cells can be clearly attributed to cell division and proliferation in response to the contact of $CD8^+$ TEM cells with B lymphoma cells decorated by the bscCD19×CD3 within the tumor. A significant contribution to T cell expansion of B lymphoma cells decorated by the bscCD19×CD3 circulating in the blood can be excluded, because circulating B lymphoma cells had been already depleted from peripheral blood at day 3, i.e. prior to the observed T cell expansion.

Next, CD8+ T Cell subpopulations have been analysed in more detail. As shown in FIG. 7, analysis of CD8+ T cells subpopulations revealed, that the effector memory subset TEM was almost exclusively responsible for the expansion of CD8+ T cells induced by the anti-CD19×anti-CD3 bispecific single chain antibody. CD8+ T cells account for most of the cytotoxic activity among all T cells and the TEM-cells together with the TEMRA-subset account for most of the cytotoxic activity among the CD8+ T cells. Except for the TEM-subset, no significant changes in cell counts could be observed among the other CD8+ T cell subpopulations like the naïve T cells not capable of proliferating upon a single activation signal as provided by the anti-CD19×anti-CD3 bispecific single chain antibody or the TEMRA-subset not capable of proliferating at all. Thus, the selective expansion of the proliferation-competent CD8+ TEM cells can be clearly attributed to cell division and proliferation in response to the contact of CD8+ TEM cells with B lymphoma cells decorated by the anti-CD19×anti-CD3 bispecific single chain antibody within the tumor; see also FIG. 14. A significant contribution to T cell expansion of B lymphoma cells decorated by the anti-CD19×anti-CD3 bispecific single chain antibody circulating in the blood can be excluded, because circulating B lymphoma cells had been already depleted from peripheral blood at day 3, i.e. prior to the observed T cell expansion.

Figure 8:
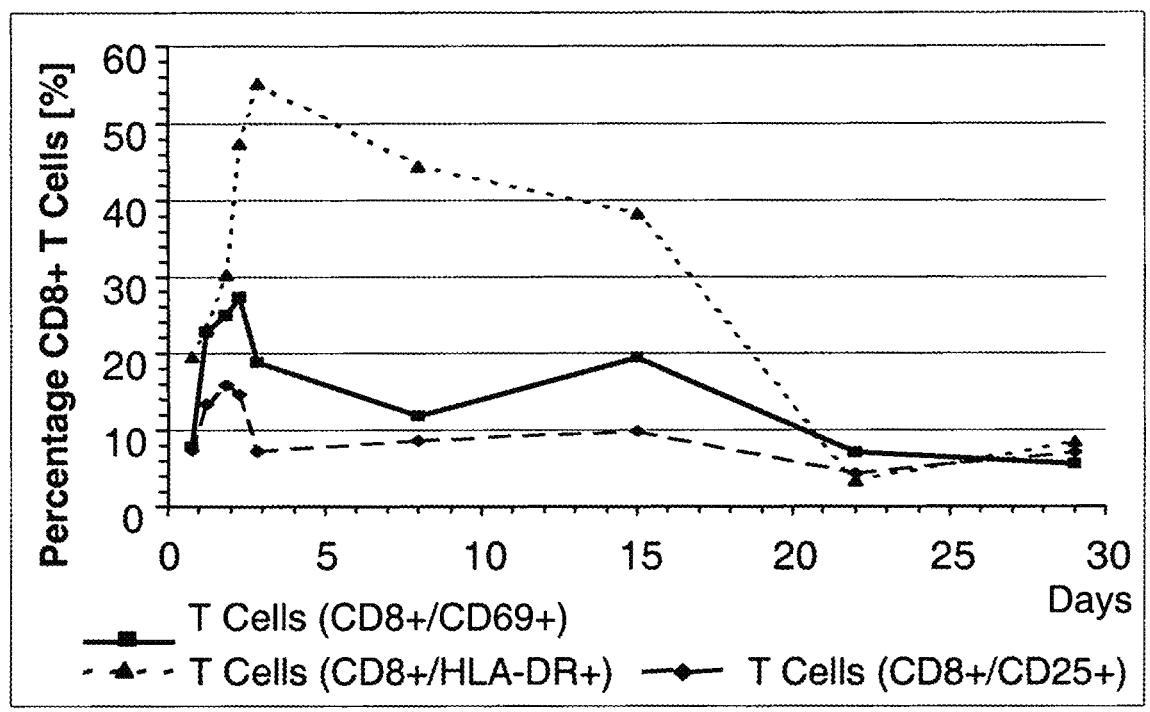
FIG. 8: Analysis of CD8+ T cell activation markers. $CD8^+$ T cell expansion is preceded by strong activation of $CD8^+$ T cells as indicated by a sustained up-regulation of the activation marker HLA-DR. Other activation markers like CD69 and CD25 only showed a short transient up-regulation after the start of infusion of the bscCD19×CD3, which is explained by activation through B lymphoma cell decorated with the bscCD19×CD3 circulating in the blood as long as the circulating B lymphoma cells were depleted during the first 3 days of treatment. In contrast, the sustained up-regulation of HLA-DR over 3 weeks reflects the activation of $CD8^+$ T cells within the tumor through the contact with tumor-resident B lymphoma cells decorated by the bscCD19×CD3. Intratumoral T cell activation results in a proliferative T cell response within the tumor leading to the expansion of T cells, which secondarily also appear in the circulating blood. Those T cells activated in the tumor and then migrated into the blood still show the long-term activation marker HLA-DR but have already down-regulated the short-term activation markers CD69 and CD25.

Finally, CD8+ T Cell activation has been analysed in that T cell activation markers have been followed as shown in FIG. 8. CD8+ T cell expansion is preceded by strong activation of CD8+ T cells as indicated by a sustained up-regulation of the activation marker HLA-DR. Other activation markers like CD69 and CD25 only showed a short transient upregulation after the start of infusion of the construct of the invention, which is explained by activation through B lymphoma cell decorated with the anti-CD19× anti-CD3 bispecific single chain antibody circulating in the blood as long as the circulating B lymphoma cells were depleted during the first 3 days of treatment. In contrast, the sustained upregulation of HLA-DR over 3 weeks reflects the activation of CD8+ T cells within the tumor through the contact with tumor-resident B lymphoma cells decorated by anti-CD19×anti-CD3 bispecific single chain antibody. Intratumoral T cell activation results in a proliferative T cell response within the tumor leading to the expansion of T cells, which secondarily also appear in the circulating blood. Those T cells activated in the tumor and then migrated into the blood still show the long-term activation marker HLA-DR but have already down-regulated the short-term activation markers CD69 and CD25.

As a conclusion, treatment with the anti-CD19×anti-CD3 bispecific single chain antibody caused long-term T cell activation and expansion. T cells with a cytotoxic phenotype predominantly account for CD8+ T cell expansion. T cell activation and proliferation is induced within the tumor by B lymphoma cells decorated with the anti-CD19×anti-CD3 bispecific single chain antibody. Decreasing T cell activation during the third week and decreasing T cell counts during the fourth week of infusion can be explained by the efficacy of the anti-CD19×anti-CD3 bispecific single chain antibody in this patient, which led to a tumor shrinkage of 58.0% as diagnosed after 4 weeks of treatment with the anti-CD19× anti-CD3 bispecific single chain antibody (see below) thus reducing the overall number of B lymphoma cells, which can induce T cell activation and proliferation mediated by the anti-CD19×anti-CD3 bispecific single chain antibody.

2.2 Depletion of Peripheral Blood B (Lymphoma) Cells by the Anti-CD19×Anti-CD3 Bispecific Single Chain Antibody Mononuclear cells from samples of peripheral blood obtained from study patient #105003 at different time points until best clinical response were analyzed by 4-color flow cytometry according to standard methods after staining with a combination of antibodies against the following 4 cell surface markers: CD3 (T cell marker)×CD16 (NK cell/macrophage marker)×CD19 (B cell marker)×CD56 (NK cell marker).

Absolute cell counts of lymphocyte subsets i.e. B, T and NK cells defined as CD19+/CD3−, CD3+ and CD3−/CD56+ cells, respectively, were calculated as % (B, T or NK cells)/(% B+% T+% NK cells) multiplied with the total lymphocyte counts of the respective blood sample as determined by a routine laboratory. Thus, absolute numbers of B (lymphoma) cells were calculated as total numbers of CD19+/CD3−-cells.

Figure 9:
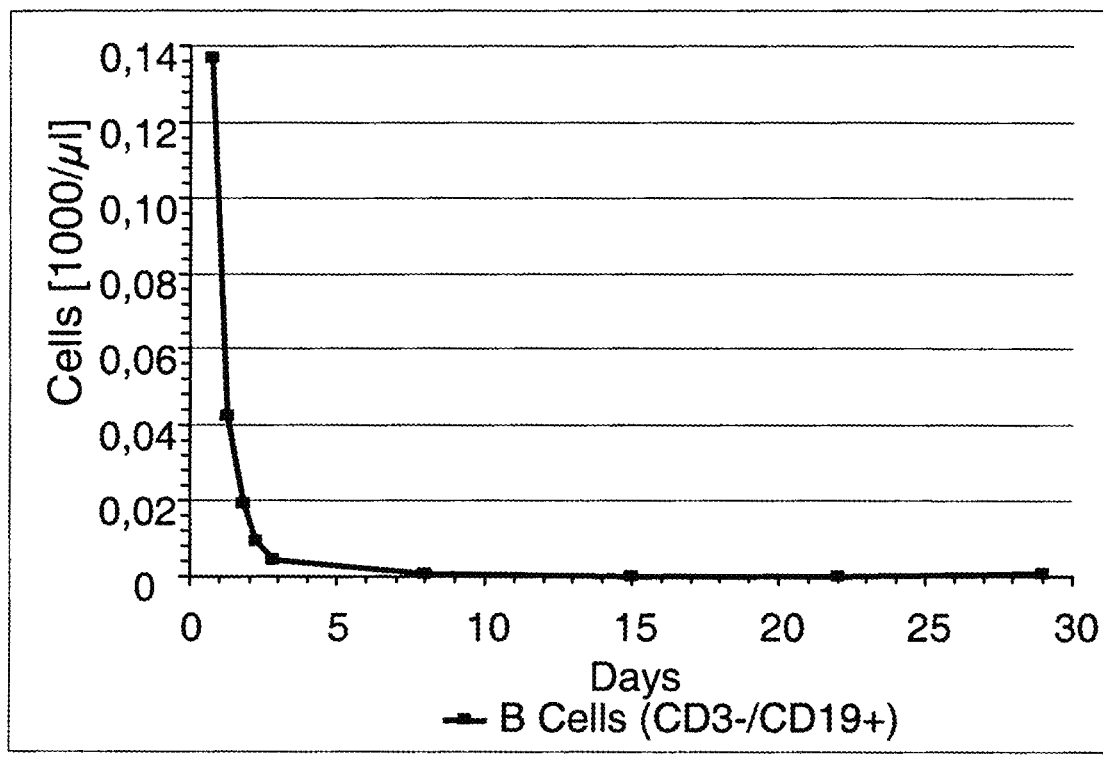
FIG. 9: B cell counts of Patient #105003. The patient started with about 140 B (lymphoma) cells per ml of blood prior to treatment. After start of infusion of the, circulating B (lymphoma) cells rapidly dropped within the first 3 days of treatment and finally completely disappeared from peripheral blood by the end of the first week of treatment. Thus, the bscCD19×CD3 can totally eliminate circulating B (lymphoma) cells due to its cytotoxic activity against said cells.

As shown in FIG. 9, the patient started with about 140 B (lymphoma) cells per ml of blood prior to treatment. After start of infusion of the anti-CD19×anti-CD3 bispecific single chain antibody, circulating B (lymphoma) cells rapidly dropped within the first 3 days of treatment and finally completely disappeared from peripheral blood by the end of the first week of treatment. Furthermore, B (lymphoma) cells remained absent from peripheral blood until the partial response was diagnosed after 4 weeks of treatment; see below. These data show that the anti-CD19×anti-CD3 bispecific single chain antibody can totally eliminate circulating B (lymphoma) cells due to its cytotoxic activity against said cells.

Figure 10:
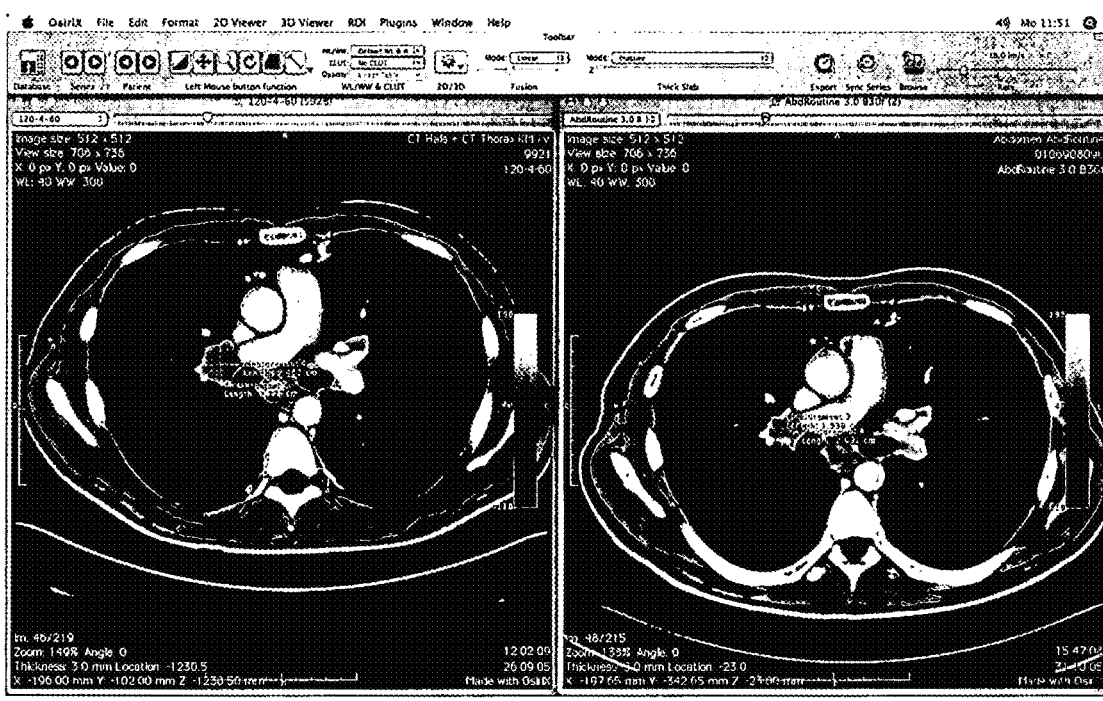
FIG. 10: (A) Size measurement of lymphoma lesion #2 (as set forth in Table in FIG. 10(B)) before (left panel; 26 Sep. 2005) and after (right panel; 31 Oct. 5) 4 weeks of treatment with the bscCD19×CD3 by computed tomography (CT). (B) Lymphoma size reduction as shown in (A) was quantified as depicted in the table shown in (B) along with five other lymphoma lesions selected for efficacy assessment. Total lymphoma size reduction is expressed as percent decrease of the sum of the products of the largest cross sectional diameters (i.e. Sum Product Diameters or SPD) of the six selected lymphoma lesions. Accordingly, a lymphoma shrinkage of 58.0% could be diagnosed fulfilling the criteria of a partial response (PR).

2.3 Reduction of Lymphoma Sizes by the Anti-CD19×Anti-CD3 Bispecific Single Chain Antibody For assessment of the efficacy of the treatment by the anti-CD19×anti-CD3 bispecific single chain antibody, standardized response criteria for response assessment for non-Hodgkin Lymphoma (NHL) have been used. According to these criteria, 6 representative lymphoma lesions have to be selected. The sum of the product of the largest cross sectional diameters of the lymphoma lesions is defined as the baseline SPD (Sum Product Diameters). The change of this SPD is then assessed a regular base during the whole treatment and follow-up period of the study. For instance, a Partial Response is defined as a 50% decrease in SPD. As demonstrated in FIG. 10, at restaging after 4 weeks of treatment, a clear reduction of lymphoma tumor masses according to the response assessment for NHL set forth above was found: A decrease in SPD of 6 reference lymphoma lesions of 58.0% was diagnosed, corresponding to a Partial Response (PR) in the tumor response assessment by computed tomography (CT). 8 weeks after treatment with the anti-CD19×anti-CD3 bispecific single chain antibody the partial response was confirmed by computer tomography showing a tumor shrinkage of 66% (SPD).

3. Patient #102003 Diagnosed with Small Lymphocytic Lymphoma (B-CLL)

This 60-year old male patient was diagnosed with a small lymphocytic lymphoma in April 1999. Relevant findings in the patient's medical history were sleep apnea syndrome, acute renal failure, herpes zoster, intermittent bronchitis and intermittent hepatopathy. The patient had a history of multiple chemotherapies (Chlorambucil; Fludarabin; Knospe; Endoxan), immunotherapies (Rituximab; anti-CD20 monoclonal antibody), and radiological treatment of the abdominal region.

In the 7-year history of the disease, the patient received 7 different chemotherapy regimens as well as Rituximab as mono therapy or combination therapy and radiotherapy without demonstrating any major response.

The administration of the anti-CD19×anti-CD3 bispecific single chain antibody was the 13$^{th}$ therapy regimen for this patient. The patient received the anti-CD19×anti-CD3 bispecific single chain antibody (SEQ ID NO.2) at a dose level of 15 µg/m$^2$/24 h for 2 weeks as a continuous infusion as detailed above. The treatment was started on Sep. 5, 2005. After two weeks of treatment, a complete restaging took place, the results of which are presented below.

Figure 11:
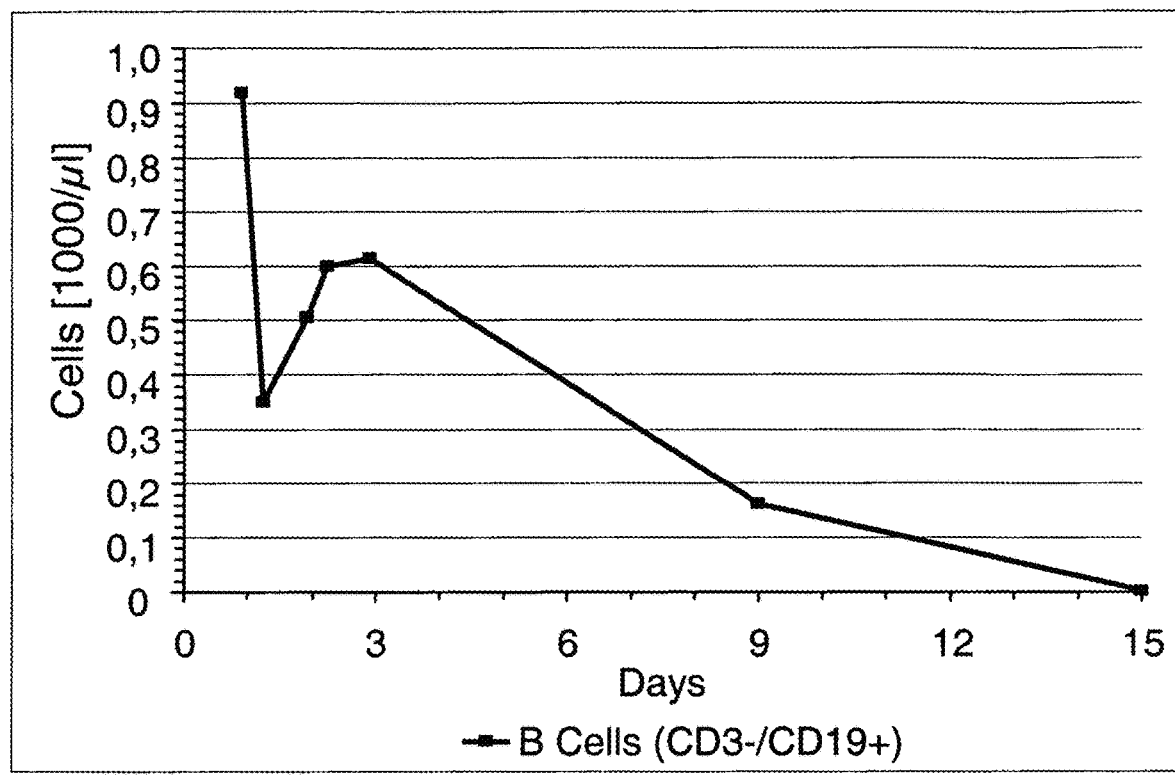
FIG. 11: B cell counts of Patient #102003. The patient started with 920 B (lymphoma) cells per ml of blood prior to treatment. After start of infusion of the bscCD19×CD3, circulating B (lymphoma) cells showed a rapid decrease followed by a transient phase of limited recovery at 600 cells per ml within the first 3 days consistent with cell redistribution. In the further course of treatment, B (lymphoma) cells were totally depleted from the circulation until the partial response (PR) was diagnosed after 2 weeks of treatment. These data confirm that the bscCD19×CD3 is capable of completely eliminating circulating B (lymphoma) cells as part of its clinical efficacy.

3.1 Depletion of Peripheral Blood B (Lymphoma) Cells by the Anti-CD19×Anti-CD3 Bispecific Single Chain Antibody B cell counts have been determined as set forth in section 2.2, supra. As shown in FIG. 11, the patient started with 920 B (lymphoma) cells per ml of blood prior to treatment. After start of infusion of the anti-CD19×anti-CD3 bispecific single chain antibody, circulating B (lymphoma) cells showed a rapid decrease followed by a transient phase of limited recovery at 600 cells per ml within the first 3 days consistent with cell redistribution. In the further course of treatment, B (lymphoma) cells were totally depleted from the circulation until the partial response was diagnosed after 2 weeks of treatment. These data confirm that the anti-CD19×anti-CD3 bispecific single chain antibody is capable of completely eliminating circulating B (lymphoma) cells as part of its clinical efficacy.

3.2 Elimination of the Lymphoma Infiltrate from the Bone Marrow by the Anti-CD19×Anti-CD3 Bispecific Single Chain Antibody In addition, bone marrow histopathology was performed before and after treatment with the anti-CD19×anti-CD3 bispecific single chain antibody. As shown in FIG. 12, left panel, before treatment, 40-50% bone marrow infiltration by small lymphocytic lymphoma cells could be observed. The diagnosis of small cell lymphocytic lymphoma/CLL was confirmed.

As depicted in FIG. 12, right panel, after treatment with the anti-CD19×anti-CD3 bispecific single chain antibody, no evidence for infiltration by small lymphocytic lymphoma cells could be found any more, whereas a significant increase of T-cells could be observed. These data demonstrate elimination of lymphoma cells from the bone marrow below detection limit by the anti-CD19×anti-CD3 bispecific single chain antibody. This finding is consistent with a complete bone marrow response which is difficult to achieve by e.g. conventional chemotherapy.

3.3 Reduction of Lymphoma Sizes by the Anti-CD19×Anti-CD3 Bispecific Single Chain Antibody Furthermore, at restaging after 2 weeks of treatment, a clear reduction of lymphoma tumor masses was seen: As shown in FIG. 13, a decrease of 57.2% of the size of six reference lymphoma lesions was diagnosed by computed tomography (CT), corresponding to a Partial Response (PR) in the tumor response assessment. In the 7-year history of the disease, during which the patient received 7 different chemotherapy regimens as well as immunotherapy and radiotherapy, without demonstrating any major response, treatment of this patient with the anti-CD19×anti-CD3 bispecific single chain antibody, for the first time provides for a successful therapy in that more than 50% shrinkage of the reference lymphoma lesions could be achieved.

4. Summary of Clinical Data

Patients with relapsed indolent NHL were included according to a classical 3+3 dose escalation design with initial doses of 0.5 µg/m$^2$/24 h. Initial steroid coverage was given to mitigate assumed cytokine release symptoms. Safety and tolerability was assessed by CTC-AE (common terminology criteria for adverse events. The NCI (National Cancer Institute) Common Terminology Criteria for Adverse Events is a descriptive terminology which can be utilized for Adverse Events (AE) reporting. A grading (severity) scale is provided for each AE term criteria and dose escalation was only allowed after a data review committee concluded safety of the previous dose with a DLT (dose limiting toxicity) period of 14 days. Biological activity was monitored by investigating levels of systemic cytokines using specific ELISAs and by quantification and characterization of peripheral immune cell subsets via FACS analysis. After 4 weeks of anti-CD19×anti-CD3 bispecific single chain antibody treatment, a control CT (Computed Tomography) scan was performed. If patients were at least stable according to standardized Cheson criteria (reviewed by central radiology), an additional 4-week cycle of anti-CD19×anti-CD3 bispecific single chain antibody was offered to the patients. The Cheson criteria were developed by the National Cancer Institute and the international pharmaceutical industry to provide a guideline for assessing clinical response in NHL. According to the criteria, a complete response is obtained when there is a complete disappearance of all detectable clinical and radiographic evidence of disease and disease related symptoms, all lymph nodes have returned to normal size, the spleen has regressed in size, and the bone marrow is cleared of lymphoma. For a partial response, there must be a 50% decrease in size of the six largest dominant lymph nodes, no increase in size of the other nodes, liver or spleen, splenic, hepatic nodules must regress by at least 50% and there must be no new disease sites.

Up to now, 19 patients with a median number of 4 previous chemo-/immuno-therapies have been included. During dose-escalation from DL1 (0.5 µg/m$^2$/24 h) (DL=dose level) up to DL3 (5 µg/m$^2$/24 h) no dose-limiting toxicity was observed and AEs (adverse events) were generally moderate. At DL4 (5 µg/m$^2$/24 h on the first day, 15 µg/m$^2$/24 h as maintenance dose), 7 patients were treated with 2 patients receiving less than 14 days of treatment (1 DLT, 1 interruption per Investigator decision).

Complete depletion of circulating B (lymphoma) cells by end of the CD19×CD3 bispecific single chain antibody infusion was observed in 9 of 14 evaluable patients (treatment >2 weeks and B-cells detectable in peripheral blood prior to anti-CD19×anti-CD3 bispecific single chain antibody infusion). A dose-dependent increase in frequency reached 100% at DL4. At DL4, 3 of 7 had relevant bone marrow (BM) infiltration (>10%) with 1 patient showing improvement and 2 patients showing complete disappearance of lymphoma cells in BM. Best overall tumour response in the 14 evaluated patients (treatment >2 weeks and scanning of all involved areas) was 1 CR (complete response in patient #109002, a 61-year old man diagnosed with follicular lymphoma, grand 1, stage 111a), 2 PR (partial response), 1 MR (minor response), 7 SD (stable disease) and 3 PD (progressive disease). In particular, patient #109002 showed further impressive results, namely a complete remission (CR); see FIGS. 14 to 16. This complete remission was achieved in said patient by an initial dose of 5 µg/m$^2$/24 h on the first day of treatment and a subsequent dose of 15 µg/m$^2$/24 h for 4 weeks. After these 4 weeks, patient #109002 showed partial responses and the patient received immediately a further 15 µg/m$^2$/24 h dose for further 4 weeks, leading to the complete response.

Without being limited by the following, the art defines "complete response", "partial response", "progressing disease" and "minor response" as follows:

A complete response is often declared if lesions are not detected by CT imaging and other tests. If CT imaging and a bone marrow test show no evidence of disease, it is a more rigorously defined a complete response.

Partial response describes a response to therapy in which least a 50% reduction in measurable tumor burden is measured.

A patient is considered to have progressing disease when they experience symptoms (fever, night sweats, etc.) and when lymph nodes increase in size or new enlarged lymph nodes are observed.

A patient is considered to have stable or regressing disease when they do not experience symptoms and when lymph nodes are not growing, or are observed to be regressing in size. Sometimes this condition or clinically observed inactivity of the disease is described as a remission.

"Minor response" roughly means a small amount of shrinkage. Minor response is not really a standard term but is increasingly used. Roughly speaking, a minor response is more than 25% of total tumor volume but less than the 50% that would make it a partial response (PR).

---

The invention claimed is:

1. A method for treating or ameliorating relapse and/or recurrence of indolent or aggressive B cell non-Hodgkin lymphoma (B NHL) or relapse and/or recurrence of B cell leukemia in a subject suffering from relapsed and/or recurrent B NHL and/or B cell leukemia, the method comprising administering to the subject a pharmaceutical composition comprising a bispecific single chain antibody comprising the amino acid sequence set forth in SEQ ID NO: 2,
wherein the bispecific single chain antibody is administered in a daily dose over at least six hours by continuous intravenous infusion for at least four weeks, wherein a lower daily dose of less than 10 µg to 80 µg per square meter patient body surface area of the bispecific single chain antibody is administered as an initial dose followed by a higher maintenance daily dose.

2. The method according to claim 1, wherein the initial dose is between 0.5-5 µg per square meter patient body surface area per 24 hours and the maintenance daily dose is 15 µg per square meter patient body surface area per 24 hours.

3. The method according to claim 1, wherein the initial dose is 15 µg per square meter patient body surface area and the maintenance daily dose is 45 µg per square meter patient body surface area.

4. The method according to claim 2, wherein the initial dose is 5 µg per square meter patient body surface area per 24 hours and the maintenance daily dose is further increased to 45 µg per square meter patient body surface area per 24 hours for the remaining period of the treatment.

5. The method according to claim 1, wherein the bispecific single chain antibody is administered in a daily dose by continuous intravenous infusion for at least eight weeks.

6. The method according to claim 5, wherein the bispecific single chain antibody is administered in a daily dose by continuous intravenous infusion for at least twelve weeks.

7. A method for treating or ameliorating relapse and/or recurrence of indolent or aggressive B cell non-Hodgkin lymphoma (B NHL) or relapse and/or recurrence of B cell leukemia in a subject suffering from relapsed and/or recurrent B NHL and/or B cell leukemia, the method comprising administering to the subject a pharmaceutical composition comprising a bispecific single chain antibody comprising the amino acid sequence set forth in SEQ ID NO: 2,
wherein the bispecific single chain antibody is administered in a daily dose over at least six hours by continuous intravenous infusion for at least four weeks, wherein a lower daily dose of 5 µg per square meter patient body surface area of the bispecific single chain antibody is administered as an initial dose followed by a higher maintenance daily dose of 15 µg per square meter patient body surface area of the bispecific single chain antibody.

8. The method according to claim 7, wherein the bispecific single chain antibody is administered in a daily dose by continuous intravenous infusion for at least eight weeks.

9. The method according to claim 8, wherein the bispecific single chain antibody is administered in a daily dose by continuous intravenous infusion for at least twelve weeks.

10. The method according to claim 7, wherein the maintenance daily dose is further increased to 45 µg per square meter patient body surface area for the remaining period of the treatment, and wherein the daily dose is administered over at least 8 hours.

* * * * *

UNITED STATES PATENT AND TRADEMARK OFFICE
CERTIFICATE OF CORRECTION

| | |
|---|---|
| PATENT NO. | : 11,154,617 B2 |
| APPLICATION NO. | : 13/219120 |
| DATED | : October 26, 2021 |
| INVENTOR(S) | : Patrick Baeuerle et al. |

It is certified that error appears in the above-identified patent and that said Letters Patent is hereby corrected as shown below:

On the Title Page

At item (54), and in the Specification, Column 1, Line 2, "TREAMENT" should be
--TREATMENT--.

Signed and Sealed this
Twelfth Day of July, 2022

*Katherine Kelly Vidal*

Katherine Kelly Vidal
*Director of the United States Patent and Trademark Office*

SEQUENCE LISTING

<160> NUMBER OF SEQ ID NOS: 47

<210> SEQ ID NO 1
<211> LENGTH: 1587
<212> TYPE: DNA
<213> ORGANISM: Artificial
<220> FEATURE:
<223> OTHER INFORMATION: Bispecific scFv CD 19 x CD3

<400> SEQUENCE: 1

```
gaattccacc atgggatgga gctgtatcat cctcttcttg gtagcaacag ctacaggtgt      60
ccactccgat atccagctga cccagtctcc agcttctttg gctgtgtctc tagggcagag     120
ggccaccatc tcctgcaagg ccagccaaag tgttgattat gatggtgata gttatttgaa     180
ctggtaccaa cagattccag gacagccacc caaactcctc atctatgatg catccaatct     240
agtttctggg atcccaccca ggtttagtgg cagtgggtct gggacagact tcaccctcaa     300
catccatcct gtggagaagg tggatgctgc aacctatcac tgtcagcaaa gtactgagga     360
tccgtggacg ttcggtggag ggaccaagct cgagatcaaa ggtggtggtg ttctggcgg      420 cggcggctcc ggtggtggtg gttctcaggt gcagctgcag cagtctgggg ctgagctggt     480
gaggcctggg tcctcagtga agatttcctg caaggcttct ggctatgcat tcagtagcta     540
ctggatgaac tgggtgaagc agaggcctgg acagggtctt gagtggattg gacagatttg     600
gcctggagat ggtgatacta actacaatgg aaagttcaag ggtaaagcca ctctgactgc     660
agacgaatcc tccagcacag cctacatgca actcagcagc ctagcatctg aggactctgc     720
ggtctatttc tgtgcaagac gggagactac gacggtaggc cgttattact atgctatgga     780
ctactggggc caagggacca cggtcaccgt ctcctccgga ggtggtggat ccgatatcaa     840
```

```
actgcagcag tcaggggctg aactggcaag acctggggcc tcagtgaaga tgtcctgcaa    900
gacttctggc tacaccttta ctaggtacac gatgcactgg gtaaaacaga ggcctggaca    960
gggtctggaa tggattggat acattaatcc tagccgtggt tatactaatt acaatcagaa   1020
gttcaaggac aaggccacat tgactacaga caaatcctcc agcacagcct acatgcaact   1080
gagcagcctg acatctgagg actctgcagt ctattactgt gcaagatatt atgatgatca   1140
ttactgcctt gactactggg gccaaggcac cactctcaca gtctcctcag tcgaaggtgg   1200
aagtggaggt tctggtggaa gtggaggttc aggtggagtc gacgacattc agctgaccca   1260
gtctccagca atcatgtctg catctccagg ggagaaggtc accatgacct gcagagccag   1320
ttcaagtgta agttacatga actggtacca gcagaagtca ggcacctccc ccaaaagatg   1380
gatttatgac acatccaaag tggcttctgg agtcccttat cgcttcagtg gcagtgggtc   1440
tgggacctca tactctctca caatcagcag catggaggct gaagatgctg ccacttatta   1500
ctgccaacag tggagtagta acccgctcac gttcggtgct gggaccaagc tggagctgaa   1560
acatcatcac catcatcatt agtcgac                                       1587
```

<210> SEQ ID NO 2
<211> LENGTH: 523
<212> TYPE: PRT
<213> ORGANISM: Artificial
<220> FEATURE:
<223> OTHER INFORMATION: Bispecific scFv CD 19 x CD 3

<400> SEQUENCE: 2

```
Met Gly Trp Ser Cys Ile Ile Leu Phe Leu Val Ala Thr Ala Thr Gly
1               5                   10                  15

Val His Ser Asp Ile Gln Leu Thr Gln Ser Pro Ala Ser Leu Ala Val
            20                  25                  30

Ser Leu Gly Gln Arg Ala Thr Ile Ser Cys Lys Ala Ser Gln Ser Val
        35                  40                  45

Asp Tyr Asp Gly Asp Ser Tyr Leu Asn Trp Tyr Gln Gln Ile Pro Gly
    50                  55                  60

Gln Pro Pro Lys Leu Leu Ile Tyr Asp Ala Ser Asn Leu Val Ser Gly
65                  70                  75                  80

Ile Pro Pro Arg Phe Ser Gly Ser Gly Ser Gly Thr Asp Phe Thr Leu
                85                  90                  95

Asn Ile His Pro Val Glu Lys Val Asp Ala Ala Thr Tyr His Cys Gln
            100                 105                 110

Gln Ser Thr Glu Asp Pro Trp Thr Phe Gly Gly Gly Thr Lys Leu Glu
        115                 120                 125

Ile Lys Gly Gly Gly Gly Ser Gly Gly Gly Gly Ser Gly Gly Gly Gly
    130                 135                 140

Ser Gln Val Gln Leu Gln Gln Ser Gly Ala Glu Leu Val Arg Pro Gly
145                 150                 155                 160

Ser Ser Val Lys Ile Ser Cys Lys Ala Ser Gly Tyr Ala Phe Ser Ser
                165                 170                 175

Tyr Trp Met Asn Trp Val Lys Gln Arg Pro Gly Gln Gly Leu Glu Trp
            180                 185                 190

Ile Gly Gln Ile Trp Pro Gly Asp Gly Asp Thr Asn Tyr Asn Gly Lys
        195                 200                 205

Phe Lys Gly Lys Ala Thr Leu Thr Ala Asp Glu Ser Ser Ser Thr Ala
    210                 215                 220

Tyr Met Gln Leu Ser Ser Leu Ala Ser Glu Asp Ser Ala Val Tyr Phe
```

Cys Ala Arg Arg Glu Thr Thr Thr Val Gly Arg Tyr Tyr Ala Met
                245                 250                 255

Asp Tyr Trp Gly Gln Gly Thr Thr Val Thr Val Ser Ser Gly Gly Gly
            260                 265                 270

Gly Ser Asp Ile Lys Leu Gln Gln Ser Gly Ala Glu Leu Ala Arg Pro
        275                 280                 285

Gly Ala Ser Val Lys Met Ser Cys Lys Thr Ser Gly Tyr Thr Phe Thr
    290                 295                 300

Arg Tyr Thr Met His Trp Val Lys Gln Arg Pro Gly Gln Gly Leu Glu
305                 310                 315                 320

Trp Ile Gly Tyr Ile Asn Pro Ser Arg Gly Tyr Thr Asn Tyr Asn Gln
                325                 330                 335

Lys Phe Lys Asp Lys Ala Thr Leu Thr Thr Asp Lys Ser Ser Ser Thr
            340                 345                 350

Ala Tyr Met Gln Leu Ser Ser Leu Thr Ser Glu Asp Ser Ala Val Tyr
        355                 360                 365

Tyr Cys Ala Arg Tyr Tyr Asp Asp His Tyr Cys Leu Asp Tyr Trp Gly
    370                 375                 380

Gln Gly Thr Thr Leu Thr Val Ser Ser Val Glu Gly Gly Ser Gly Gly
385                 390                 395                 400

Ser Gly Gly Ser Gly Gly Ser Gly Gly Val Asp Asp Ile Gln Leu Thr
                405                 410                 415

Gln Ser Pro Ala Ile Met Ser Ala Ser Pro Gly Glu Lys Val Thr Met
            420                 425                 430

Thr Cys Arg Ala Ser Ser Ser Val Ser Tyr Met Asn Trp Tyr Gln Gln
        435                 440                 445

Lys Ser Gly Thr Ser Pro Lys Arg Trp Ile Tyr Asp Thr Ser Lys Val
    450                 455                 460

Ala Ser Gly Val Pro Tyr Arg Phe Ser Gly Ser Gly Ser Gly Thr Ser
465                 470                 475                 480

Tyr Ser Leu Thr Ile Ser Ser Met Glu Ala Glu Asp Ala Ala Thr Tyr
                485                 490                 495

Tyr Cys Gln Gln Trp Ser Ser Asn Pro Leu Thr Phe Gly Ala Gly Thr
            500                 505                 510

Lys Leu Glu Leu Lys His His His His His His
        515                 520

<210> SEQ ID NO 3
<211> LENGTH: 1533
<212> TYPE: DNA
<213> ORGANISM: Artificial
<220> FEATURE:
<223> OTHER INFORMATION: CD 19 VH/VL x CD3 VH/VL (BsrG I to Sal I)

<400> SEQUENCE: 3
tgtacactcc caggtgcagc tgcagcagtc tggggctgag ctggtgaggc ctgggtcctc      60
agtgaagatt tcctgcaagg cttctggcta tgcattcagt agctactgga tgaactgggt     120
gaagcagagg cctggacagg gtcttgagtg gattggacag atttggcctg agatggtga     180 tactaactac aatggaaagt tcaagggtaa agccactctg actgcagacg aatcctccag     240
cacagcctac atgcaactca gcagcctagc atctgaggac tctgcggtct atttctgtgc     300
aagacgggag actacgacgg taggccgtta ttactatgct atggactact ggggccaagg     360
gaccacggtc accgtctcct ccggtggtgg tggttctggc ggcggcggct ccggtggtgg     420

```
tggttctgat atccagctga cccagtctcc agcttctttg ctgtgtctc tagggcagag      480 ggccaccatc tcctgcaagg ccagccaaag tgttgattat gatggtgata gttatttgaa     540
ctggtaccaa cagattccag gacagccacc caaactcctc atctatgatg catccaatct     600
agtttctggg atcccaccca ggtttagtgg cagtgggtct gggacagact tcaccctcaa     660
catccatcct gtggagaagg tggatgctgc aacctatcac tgtcagcaaa gtactgagga     720
tccgtggacg ttcggtggag ggaccaagct cgagatcaaa tccggaggtg gtggatccga     780
tatcaaactg cagcagtcag gggctgaact ggcaagacct ggggcctcag tgaagatgtc     840
ctgcaagact tctggctaca cctttactag gtacacgatg cactgggtaa acagaggcc      900 tggacagggt ctggaatgga ttggatacat taatcctagc cgtggttata ctaattacaa     960
tcagaagttc aaggacaagg ccacattgac tacagacaaa tcctccagca cagcctacat    1020
gcaactgagc agcctgacat ctgaggactc tgcagtctat tactgtgcaa gatattatga    1080
tgatcattac tgccttgact actggggcca aggcaccact ctcacagtct cctcagtcga    1140
aggtggaagt ggaggttctg gtggaagtgg aggttcaggt ggagtcgacg acattcagct    1200
gacccagtct ccagcaatca tgtctgcatc tccaggggag aaggtcacca tgacctgcag    1260
agccagttca agtgtaagtt acatgaactg gtaccagcag aagtcaggca cctcccccaa    1320
aagatggatt tatgacacat ccaaagtggc ttctggagtc ccttatcgct tcagtggcag    1380
tgggtctggg acctcatact ctctcacaat cagcagcatg gaggctgaag atgctgccac    1440
ttattactgc caacagtgga gtagtaaccc gctcacgttc ggtgctggga ccaagctgga    1500
gctgaaacat catcaccatc atcattagtc gac                                 1533

<210> SEQ ID NO 4
<211> LENGTH: 505
<212> TYPE: PRT
<213> ORGANISM: Artificial
<220> FEATURE:
<223> OTHER INFORMATION: CD 19 VH/VL x CD3 VH/VL (mature protein w/o
      Leader)

<400> SEQUENCE: 4

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
        50                  55                  60

Lys Gly Lys Ala Thr Leu Thr Ala Asp Glu Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Gly Gly Gly Gly
        115                 120                 125

Ser Gly Gly Gly Gly Ser Gly Gly Gly Ser Asp Ile Gln Leu Thr
    130                 135                 140

Gln Ser Pro Ala Ser Leu Ala Val Ser Leu Gly Gln Arg Ala Thr Ile
145                 150                 155                 160
```

Ser Cys Lys Ala Ser Gln Ser Val Asp Tyr Asp Gly Asp Ser Tyr Leu
            165                 170                 175

Asn Trp Tyr Gln Gln Ile Pro Gly Gln Pro Lys Leu Leu Ile Tyr
            180                 185                 190

Asp Ala Ser Asn Leu Val Ser Gly Ile Pro Pro Arg Phe Ser Gly Ser
            195                 200                 205

Gly Ser Gly Thr Asp Phe Thr Leu Asn Ile His Pro Val Glu Lys Val
210                 215                 220

Asp Ala Ala Thr Tyr His Cys Gln Gln Ser Thr Glu Asp Pro Trp Thr
225                 230                 235                 240

Phe Gly Gly Gly Thr Lys Leu Glu Ile Lys Ser Gly Gly Gly Gly Ser
            245                 250                 255

Asp Ile Lys Leu Gln Gln Ser Gly Ala Glu Leu Ala Arg Pro Gly Ala
            260                 265                 270

Ser Val Lys Met Ser Cys Lys Thr Ser Gly Tyr Thr Phe Thr Arg Tyr
            275                 280                 285

Thr Met His Trp Val Lys Gln Arg Pro Gly Gln Gly Leu Glu Trp Ile
290                 295                 300

Gly Tyr Ile Asn Pro Ser Arg Gly Tyr Thr Asn Tyr Asn Gln Lys Phe
305                 310                 315                 320

Lys Asp Lys Ala Thr Leu Thr Thr Asp Lys Ser Ser Ser Thr Ala Tyr
            325                 330                 335

Met Gln Leu Ser Ser Leu Thr Ser Glu Asp Ser Ala Val Tyr Tyr Cys
            340                 345                 350

Ala Arg Tyr Tyr Asp Asp His Tyr Cys Leu Asp Tyr Trp Gly Gln Gly
            355                 360                 365

Thr Thr Leu Thr Val Ser Ser Val Glu Gly Gly Ser Gly Gly Ser Gly
            370                 375                 380

Gly Ser Gly Gly Ser Gly Val Asp Asp Ile Gln Leu Thr Gln Ser
385                 390                 395                 400

Pro Ala Ile Met Ser Ala Ser Pro Gly Glu Lys Val Thr Met Thr Cys
            405                 410                 415

Arg Ala Ser Ser Ser Val Ser Tyr Met Asn Trp Tyr Gln Gln Lys Ser
            420                 425                 430

Gly Thr Ser Pro Lys Arg Trp Ile Tyr Asp Thr Ser Lys Val Ala Ser
            435                 440                 445

Gly Val Pro Tyr Arg Phe Ser Gly Ser Gly Ser Gly Thr Ser Tyr Ser
            450                 455                 460

Leu Thr Ile Ser Ser Met Glu Ala Glu Asp Ala Ala Thr Tyr Tyr Cys
465                 470                 475                 480

Gln Gln Trp Ser Ser Asn Pro Leu Thr Phe Gly Ala Gly Thr Lys Leu
            485                 490                 495

Glu Leu Lys His His His His His
            500                 505

<210> SEQ ID NO 5
<211> LENGTH: 1531
<212> TYPE: DNA
<213> ORGANISM: Artificial
<220> FEATURE:
<223> OTHER INFORMATION: CD3 VH/VL x CD19 VH/VL (BsrG I to Sal I)

<400> SEQUENCE: 5
tgtacactcc gatatcaaac tgcagcagtc agggctgaa ctggcaagac ctggggcctc    60

```
agtgaagatg tcctgcaaga cttctggcta cacctttact aggtacacga tgcactgggt    120
aaaacagagg cctggacagg gtctggaatg gattggatac attaatccta gccgtggtta    180
tactaattac aatcagaagt tcaaggacaa ggccacattg actacagaca aatcctccag    240
cacagcctac atgcaactga gcagcctgac atctgaggac tctgcagtct attactgtgc    300
aagatattat gatgatcatt actgccttga ctactggggc caaggcacca ctctcacagt    360
ctcctcaggt ggtggtggtt ctggcggcgg cggctccggt ggtggtggtt ctgacattca    420
gctgacccag tctccagcaa tcatgtctgc atctccaggg gagaaggtca ccatgacctg    480
cagagccagt tcaagtgtaa gttacatgaa ctggtaccag cagaagtcag gcacctcccc    540
caaaagatgg atttatgaca catccaaagt ggcttctgga gtcccttatc gcttcagtgg    600
cagtgggtct gggacctcat actctctcac aatcagcagc atggaggctg aagatgctgc    660
cacttattac tgccaacagt ggagtagtaa cccgctcacg ttcggtgctg ggaccaagct    720
ggagctgaaa tccggaggtg gtggatccca ggtgcagctg cagcagtctg ggctgagctt    780
ggtgaggcct gggtcctcag tgaagatttc ctgcaaggct tctggctatg cattcagtag    840
ctactggatg aactgggtga agcagaggcc tggacagggt cttgagtgga ttggacagat    900
ttggcctgga gatggtgata ctaactacaa tggaaagttc aagggtaaag ccactctgac    960
tgcagacgaa tcctccagca gcctacatgc aactcagcag cctagcatct gaggactc       1020 tgcggtctat ttctgtgcaa gacgggagac tacgacggta ggccgttatt actatgctat    1080
ggactactgg ggccaaggga ccacggtcac cgtctcctcc ggtggtggtg gttctggcgg    1140
cggcggctcc ggtggtggtg gttctgatat ccagctgacc cagtctccag cttctttggc    1200
tgtgtctcta gggcagaggg ccaccatctc ctgcaaggcc agccaaagtg ttgattatga    1260
tggtgatagt tatttgaact ggtaccaaca gattccagga cagccaccca aactcctcat    1320
ctatgatgca tccaatctag tttctgggat cccacccagg tttagtggca gtgggtctgg    1380
gacagacttc accctcaaca tccatcctgt ggagaaggtg gatgctgcaa cctatcactg    1440
tcagcaaagt actgaggatc cgtggacgtt cggtggaggg accaagctcg agatcaaatc    1500
cgggcatcat caccatcatc attgagtcga c                                   1531
```

<210> SEQ ID NO 6  
<211> LENGTH: 504  
<212> TYPE: PRT  
<213> ORGANISM: Artificial  
<220> FEATURE:  
<223> OTHER INFORMATION: CD3 VH/VL x CD19 VH/VL

<400> SEQUENCE: 6

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly

```
                    100                 105                 110
Thr Thr Leu Thr Val Ser Ser Gly Gly Gly Ser Gly Gly Gly
            115                 120                 125
Ser Gly Gly Gly Ser Asp Ile Gln Leu Thr Gln Ser Pro Ala Ile
130                 135                 140
Met Ser Ala Ser Pro Gly Glu Lys Val Thr Met Thr Cys Arg Ala Ser
145                 150                 155                 160
Ser Ser Val Ser Tyr Met Asn Trp Tyr Gln Gln Lys Ser Gly Thr Ser
                165                 170                 175
Pro Lys Arg Trp Ile Tyr Asp Thr Ser Lys Val Ala Ser Gly Val Pro
                180                 185                 190
Tyr Arg Phe Ser Gly Ser Gly Ser Gly Thr Ser Tyr Ser Leu Thr Ile
            195                 200                 205
Ser Ser Met Glu Ala Glu Asp Ala Ala Thr Tyr Tyr Cys Gln Gln Trp
            210                 215                 220
Ser Ser Asn Pro Leu Thr Phe Gly Ala Gly Thr Lys Leu Glu Leu Lys
225                 230                 235                 240
Ser Gly Gly Gly Gly Ser Gln Val Gln Leu Gln Gln Ser Gly Ala Glu
                245                 250                 255
Leu Val Arg Pro Gly Ser Ser Val Lys Ile Ser Cys Lys Ala Ser Gly
                260                 265                 270
Tyr Ala Phe Ser Ser Tyr Trp Met Asn Trp Val Lys Gln Arg Pro Gly
            275                 280                 285
Gln Gly Leu Glu Trp Ile Gly Gln Ile Trp Pro Gly Asp Gly Asp Thr
            290                 295                 300
Asn Tyr Asn Gly Lys Phe Lys Gly Lys Ala Thr Leu Thr Ala Asp Glu
305                 310                 315                 320
Ser Ser Ser Thr Ala Tyr Met Gln Leu Ser Ser Leu Ala Ser Glu Asp
                325                 330                 335
Ser Ala Val Tyr Phe Cys Ala Arg Arg Glu Thr Thr Thr Val Gly Arg
                340                 345                 350
Tyr Tyr Tyr Ala Met Asp Tyr Trp Gly Gln Gly Thr Thr Val Thr Val
            355                 360                 365
Ser Ser Gly Gly Gly Gly Ser Gly Gly Gly Gly Ser Gly Gly Gly Gly
            370                 375                 380
Ser Asp Ile Gln Leu Thr Gln Ser Pro Ala Ser Leu Ala Val Ser Leu
385                 390                 395                 400
Gly Gln Arg Ala Thr Ile Ser Cys Lys Ala Ser Gln Ser Val Asp Tyr
                405                 410                 415
Asp Gly Asp Ser Tyr Leu Asn Trp Tyr Gln Gln Ile Pro Gly Gln Pro
                420                 425                 430
Pro Lys Leu Leu Ile Tyr Asp Ala Ser Asn Leu Val Ser Gly Ile Pro
            435                 440                 445
Pro Arg Phe Ser Gly Ser Gly Ser Gly Thr Asp Phe Thr Leu Asn Ile
            450                 455                 460
His Pro Val Glu Lys Val Asp Ala Ala Thr Tyr His Cys Gln Gln Ser
465                 470                 475                 480
Thr Glu Asp Pro Trp Thr Phe Gly Gly Gly Thr Lys Leu Glu Ile Lys
                485                 490                 495
Ser Gly His His His His His His
            500

<210> SEQ ID NO 7
```

<211> LENGTH: 1528
<212> TYPE: DNA
<213> ORGANISM: Artificial
<220> FEATURE:
<223> OTHER INFORMATION: CD3 VH/VL x CD19 VL/VH (BsrG I to Sal I)

<400> SEQUENCE: 7

```
tgtacactcc gatatcaaac tgcagcagtc aggggctgaa ctggcaagac ctggggcctc     60
agtgaagatg tcctgcaaga cttctggcta cacctttact aggtacacga tgcactgggt    120
aaaacagagg cctggacagg gtctggaatg gattggatac attaatccta gccgtggtta    180
tactaattac aatcagaagt tcaaggacaa ggccacattg actacagaca atcctccag     240
cacagcctac atgcaactga gcagcctgac atctgaggac tctgcagtct attactgtgc    300
aagatattat gatgatcatt actgccttga ctactgggc caaggcacca ctctcacagt    360
ctcctcaggt ggtggtggtt ctggcggcgg cggctccggt ggtggtggtt ctgacattca    420
gctgacccag tctccagcaa tcatgtctgc atctccaggg gagaaggtca ccatgacctg    480
cagagccagt tcaagtgtaa gttacatgaa ctggtaccag cagaagtcag gcacctcccc    540
caaaagatgg atttatgaca catccaaagt ggcttctgga gtcccttatc gcttcagtgg    600
cagtgggtct gggacctcat actctctcac aatcagcagc atggaggctg aagatgctgc    660
cacttattac tgccaacagt ggagtagtaa cccgctcacg ttcggtgctg gaccaagct     720
ggagctgaaa tccggaggtg gtggatccga tatccagctg acccagtctc cagcttcttt    780
ggctgtgtct ctagggcaga gggccaccat ctcctgcaag gccagccaaa gtgttgatta    840
tgatggtgat agttatttga actggtacca acagattcca ggacagccac ccaaactcct    900
catctatgat gcatccaatc tagtttctgg gatcccaccc aggtttagtg gcagtgggtc    960
tgggacagac ttcacccctca acatccatcc tgtggagaag gtggatgctg caacctatca   1020
ctgtcagcaa agtactgagg atccgtggac gttcggtgga gggaccaagc tcgagatcaa   1080
aggtggtggt ggttctggcg gcggcggctc cgtggtggt ggttctcagg tgcagctgca   1140
gcagtctggg gctgagctgg tgaggcctgg gtcctcagtg aagatttcct gcaaggcttc   1200
tggctatgca ttcagtagct actggatgaa ctgggtgaag cagaggcctg gacagggtct   1260
tgagtggatt ggacagattt ggcctggaga tggtgatact aactacaatg gaaagttcaa   1320
gggtaaagcc actctgactg cagacgaatc ctccagcaca gcctacatgc aactcagcag   1380
cctagcatct gaggactctg cggtctattt ctgtgcaaga cgggagacta cgacggtagg   1440
ccgttattac tatgctatgg actactgggg ccaagggacc acggtcaccg tctcctccgg   1500
gcatcatcac catcatcatt gagtcgac                                       1528
```

<210> SEQ ID NO 8
<211> LENGTH: 503
<212> TYPE: PRT
<213> ORGANISM: Artificial
<220> FEATURE:
<223> OTHER INFORMATION: CD3 VH/VL x CD19 VL/VH (mature protein w/o
Leader)

<400> SEQUENCE: 8

```
Asp Ile Lys Leu Gln Gln Ser Gly Ala Glu Leu Ala Arg Pro Gly Ala
  1               5                  10                  15

Ser Val Lys Met Ser Cys Lys Thr Ser Gly Tyr Thr Phe Thr Arg Tyr
             20                  25                  30

Thr Met His Trp Val Lys Gln Arg Pro Gly Gln Gly Leu Glu Trp Ile
         35                  40                  45
```

```
Gly Tyr Ile Asn Pro Ser Arg Gly Tyr Thr Asn Tyr Asn Gln Lys Phe
 50                  55                  60

Lys Asp Lys Ala Thr Leu Thr Thr Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
             100                 105                 110

Thr Thr Leu Thr Val Ser Ser Gly Gly Gly Ser Gly Gly Gly
         115                 120                 125

Ser Gly Gly Gly Ser Asp Ile Gln Leu Thr Gln Ser Pro Ala Ile
130                 135                 140

Met Ser Ala Ser Pro Gly Glu Lys Val Thr Met Thr Cys Arg Ala Ser
145                 150                 155                 160

Ser Ser Val Ser Tyr Met Asn Trp Tyr Gln Gln Lys Ser Gly Thr Ser
                 165                 170                 175

Pro Lys Arg Trp Ile Tyr Asp Thr Ser Lys Val Ala Ser Gly Val Pro
             180                 185                 190

Tyr Arg Phe Ser Gly Ser Gly Ser Gly Thr Ser Tyr Ser Leu Thr Ile
         195                 200                 205

Ser Ser Met Glu Ala Glu Asp Ala Ala Thr Tyr Tyr Cys Gln Gln Trp
210                 215                 220

Ser Ser Asn Pro Leu Thr Phe Gly Ala Gly Thr Lys Leu Glu Leu Lys
225                 230                 235                 240

Ser Gly Gly Gly Gly Ser Asp Ile Gln Leu Thr Gln Ser Pro Ala Ser
                 245                 250                 255

Leu Ala Val Ser Leu Gly Gln Arg Ala Thr Ile Ser Cys Lys Ala Ser
             260                 265                 270

Gln Ser Val Asp Tyr Asp Gly Asp Ser Tyr Leu Asn Trp Tyr Gln Gln
         275                 280                 285

Ile Pro Gly Gln Pro Pro Lys Leu Leu Ile Tyr Asp Ala Ser Asn Leu
290                 295                 300

Val Ser Gly Ile Pro Pro Arg Phe Ser Gly Ser Gly Ser Gly Thr Asp
305                 310                 315                 320

Phe Thr Leu Asn Ile His Pro Val Glu Lys Val Asp Ala Ala Thr Tyr
                 325                 330                 335

His Cys Gln Gln Ser Thr Glu Asp Pro Trp Thr Phe Gly Gly Gly Thr
             340                 345                 350

Lys Leu Glu Ile Lys Gly Gly Gly Gly Ser Gly Gly Gly Gly Ser Gly
         355                 360                 365

Gly Gly Gly Ser Gln Val Gln Leu Gln Gln Ser Gly Ala Glu Leu Val
     370                 375                 380

Arg Pro Gly Ser Ser Val Lys Ile Ser Cys Lys Ala Ser Gly Tyr Ala
385                 390                 395                 400

Phe Ser Ser Tyr Trp Met Asn Trp Val Lys Gln Arg Pro Gly Gln Gly
                 405                 410                 415

Leu Glu Trp Ile Gly Gln Ile Trp Pro Gly Asp Gly Asp Thr Asn Tyr
             420                 425                 430

Asn Gly Lys Phe Lys Gly Lys Ala Thr Leu Thr Ala Asp Glu Ser Ser
         435                 440                 445

Ser Thr Ala Tyr Met Gln Leu Ser Ser Leu Ala Ser Glu Asp Ser Ala
450                 455                 460
```

```
Val Tyr Phe Cys Ala Arg Arg Glu Thr Thr Thr Val Gly Arg Tyr Tyr
465                 470                 475                 480

Tyr Ala Met Asp Tyr Trp Gly Gln Gly Thr Thr Val Thr Val Ser Ser
                485                 490                 495

Gly His His His His His His
            500
```

<210> SEQ ID NO 9
<211> LENGTH: 10
<212> TYPE: PRT
<213> ORGANISM: Artificial
<220> FEATURE:
<223> OTHER INFORMATION: CD3 CDR-H1

<400> SEQUENCE: 9

```
Gly Tyr Thr Phe Thr Arg Tyr Thr Met His
1               5                   10
```

<210> SEQ ID NO 10
<211> LENGTH: 17
<212> TYPE: PRT
<213> ORGANISM: Artificial
<220> FEATURE:
<223> OTHER INFORMATION: CD3 CDR-H2

<400> SEQUENCE: 10

```
Tyr Ile Asn Pro Ser Arg Gly Tyr Thr Asn Tyr Asn Gln Lys Phe Lys
1               5                   10                  15

Asp
```

<210> SEQ ID NO 11
<211> LENGTH: 10
<212> TYPE: PRT
<213> ORGANISM: Artificial
<220> FEATURE:
<223> OTHER INFORMATION: CD3 CDR-H3

<400> SEQUENCE: 11

```
Tyr Tyr Asp Asp His Tyr Cys Leu Asp Tyr
1               5                   10
```

<210> SEQ ID NO 12
<211> LENGTH: 10
<212> TYPE: PRT
<213> ORGANISM: Artificial
<220> FEATURE:
<223> OTHER INFORMATION: CD3 CDR-L1

<400> SEQUENCE: 12

```
Arg Ala Ser Ser Ser Val Ser Tyr Met Asn
1               5                   10
```

<210> SEQ ID NO 13
<211> LENGTH: 7
<212> TYPE: PRT
<213> ORGANISM: Artificial
<220> FEATURE:
<223> OTHER INFORMATION: CD3 CDR-L2

<400> SEQUENCE: 13

```
Asp Thr Ser Lys Val Ala Ser
1               5
```

<210> SEQ ID NO 14
<211> LENGTH: 9

```
<212> TYPE: PRT
<213> ORGANISM: Artificial
<220> FEATURE:
<223> OTHER INFORMATION: CD3 CDR-L3

<400> SEQUENCE: 14

Gln Gln Trp Ser Ser Asn Pro Leu Thr
1               5

<210> SEQ ID NO 15
<211> LENGTH: 124
<212> TYPE: PRT
<213> ORGANISM: Artificial
<220> FEATURE:
<223> OTHER INFORMATION: anti-CD19 VH

<400> SEQUENCE: 15

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120

<210> SEQ ID NO 16
<211> LENGTH: 111
<212> TYPE: PRT
<213> ORGANISM: Artificial
<220> FEATURE:
<223> OTHER INFORMATION: anti-CD19 VL

<400> SEQUENCE: 16

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110

<210> SEQ ID NO 17
<211> LENGTH: 119
<212> TYPE: PRT
```

```
<213> ORGANISM: Artificial
<220> FEATURE:
<223> OTHER INFORMATION: anti-CD3 VH

<400> SEQUENCE: 17

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 18
<211> LENGTH: 106
<212> TYPE: PRT
<213> ORGANISM: Artificial
<220> FEATURE:
<223> OTHER INFORMATION: anti-CD3 VL

<400> SEQUENCE: 18

Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 19
<211> LENGTH: 36
<212> TYPE: DNA
<213> ORGANISM: Artificial
<220> FEATURE:
<223> OTHER INFORMATION: Primer 5'L1

<400> SEQUENCE: 19
gaagcacgcg tagatatckt gmtsacccaa wctcca                            36

<210> SEQ ID NO 20
<211> LENGTH: 30
<212> TYPE: DNA
<213> ORGANISM: Artificial
<220> FEATURE:
```

<223> OTHER INFORMATION: Primer 3'K

<400> SEQUENCE: 20
gaagatggat ccagcggccg cagcatcagc                                    30

<210> SEQ ID NO 21
<211> LENGTH: 33
<212> TYPE: DNA
<213> ORGANISM: Artificial
<220> FEATURE:
<223> OTHER INFORMATION: Primer 5'H1

<400> SEQUENCE: 21
cagccggcca tggcgcaggt scagctgcag sag                                33

<210> SEQ ID NO 22
<211> LENGTH: 39
<212> TYPE: DNA
<213> ORGANISM: Artificial
<220> FEATURE:
<223> OTHER INFORMATION: Primer 3'G

<400> SEQUENCE: 22
accaggggcc agtggataga caagcttggg tgtcgtttt                          39

<210> SEQ ID NO 23
<211> LENGTH: 38
<212> TYPE: DNA
<213> ORGANISM: Artificial
<220> FEATURE:
<223> OTHER INFORMATION: Primer 5'VLB5RRV

<400> SEQUENCE: 23
aggtgtacac tcctgatatc cagctgaccc agtctcca                           38

<210> SEQ ID NO 24
<211> LENGTH: 48
<212> TYPE: DNA
<213> ORGANISM: Artificial
<220> FEATURE:
<223> OTHER INFORMATION: Primer 3'VLGS15

<400> SEQUENCE: 24
ggagccgccg ccgccagaac caccaccttt gatctcgagc ttggtccc                48

<210> SEQ ID NO 25
<211> LENGTH: 53
<212> TYPE: DNA
<213> ORGANISM: Artificial
<220> FEATURE:
<223> OTHER INFORMATION: Primer 5'VHGS15

<400> SEQUENCE: 25
ggcggcggcg gctccggtgg tggtggttct caggtsmarc tgcagsagtc wgg          53

<210> SEQ ID NO 26
<211> LENGTH: 39
<212> TYPE: DNA
<213> ORGANISM: Artificial
<220> FEATURE:
<223> OTHER INFORMATION: Primer 3'VHBspE1

<400> SEQUENCE: 26
aatccggagg agacggtgac cgtggtccct tggccccag                          39

```
<210> SEQ ID NO 27
<211> LENGTH: 38
<212> TYPE: DNA
<213> ORGANISM: Artificial
<220> FEATURE:
<223> OTHER INFORMATION: Primer 5'VLL2KBspEIGS

<400> SEQUENCE: 27
cttccggagg tggtggatcc gacattcagc tgacccag                     38

<210> SEQ ID NO 28
<211> LENGTH: 25
<212> TYPE: DNA
<213> ORGANISM: Artificial
<220> FEATURE:
<223> OTHER INFORMATION: Primer 3'VHL2KBspEI (C-terminal)

<400> SEQUENCE: 28
cctccggagg agactgtgag agtgg                                   25

<210> SEQ ID NO 29
<211> LENGTH: 38
<212> TYPE: DNA
<213> ORGANISM: Artificial
<220> FEATURE:
<223> OTHER INFORMATION: Primer 5'VHCD19BspEIGS

<400> SEQUENCE: 29
cttccggagg tggtggatcc caggtgcagc tgcagcag                     38

<210> SEQ ID NO 30
<211> LENGTH: 25
<212> TYPE: DNA
<213> ORGANISM: Artificial
<220> FEATURE:
<223> OTHER INFORMATION: Primer 3VLCD19BspEI (C-terminal)

<400> SEQUENCE: 30
cctccggatt tgatctcgag cttgg                                   25

<210> SEQ ID NO 31
<211> LENGTH: 35
<212> TYPE: DNA
<213> ORGANISM: Artificial
<220> FEATURE:
<223> OTHER INFORMATION: Primer 5VLCD19BspEIGS

<400> SEQUENCE: 31
cttccggagg tggtggatcc gatatccagc tgacc                        35

<210> SEQ ID NO 32
<211> LENGTH: 31
<212> TYPE: DNA
<213> ORGANISM: Artificial
<220> FEATURE:
<223> OTHER INFORMATION: Primer 5VHL2KBsrGI

<400> SEQUENCE: 32
aggtgtacac tccgatatca aactgcagca g                            31

<210> SEQ ID NO 33
<211> LENGTH: 50
<212> TYPE: DNA
<213> ORGANISM: Artificial
<220> FEATURE:
<223> OTHER INFORMATION: Primer 3VHL2KGS15
```

<400> SEQUENCE: 33
ggagccgccg ccgccagaac caccaccacc tgaggagact gtgagagtgg          50

<210> SEQ ID NO 34
<211> LENGTH: 53
<212> TYPE: DNA
<213> ORGANISM: Artificial
<220> FEATURE:
<223> OTHER INFORMATION: Primer 5VLL2KGS15

<400> SEQUENCE: 34
ggcggcggcg gctccggtgg tgtggttct gacattcagc tgacccagtc tcc       53

<210> SEQ ID NO 35
<211> LENGTH: 25
<212> TYPE: DNA
<213> ORGANISM: Artificial
<220> FEATURE:
<223> OTHER INFORMATION: Primer 3VLL2KBspEI

<400> SEQUENCE: 35
aatccggatt tcagctccag cttgg                                     25

<210> SEQ ID NO 36
<211> LENGTH: 31
<212> TYPE: DNA
<213> ORGANISM: Artificial
<220> FEATURE:
<223> OTHER INFORMATION: Primer 5VHCD19BsrGI

<400> SEQUENCE: 36
aggtgtacac tcccaggtgc agctgcagca g                              31

<210> SEQ ID NO 37
<211> LENGTH: 50
<212> TYPE: DNA
<213> ORGANISM: Artificial
<220> FEATURE:
<223> OTHER INFORMATION: Primer 3VHCD19GS15

<400> SEQUENCE: 37
ggagccgccg ccgccagaac caccaccacc ggaggagacg gtgaccgtgg          50

<210> SEQ ID NO 38
<211> LENGTH: 53
<212> TYPE: DNA
<213> ORGANISM: Artificial
<220> FEATURE:
<223> OTHER INFORMATION: Primer 5VLCD19GS15

<400> SEQUENCE: 38
ggcggcggcg gctccggtgg tgtggttct gatatccagc tgacccagtc tcc       53

<210> SEQ ID NO 39
<211> LENGTH: 25
<212> TYPE: DNA
<213> ORGANISM: Artificial
<220> FEATURE:
<223> OTHER INFORMATION: Primer 3VLCD19BspEI

<400> SEQUENCE: 39
aatccggatt tgatctcgag cttgg                                     25

<210> SEQ ID NO 40
<211> LENGTH: 35

```
<212> TYPE: DNA
<213> ORGANISM: Artificial
<220> FEATURE:
<223> OTHER INFORMATION: Primer 5'VLL2KBsrGI

<400> SEQUENCE: 40
aggtgtacac tccgacattc agctgaccca gtctc                                35

<210> SEQ ID NO 41
<211> LENGTH: 50
<212> TYPE: DNA
<213> ORGANISM: Artificial
<220> FEATURE:
<223> OTHER INFORMATION: Primer 3'VLL2KGS15

<400> SEQUENCE: 41
ggagccgccg ccgccagaac caccaccacc tttcagctcc agcttggtcc                 50

<210> SEQ ID NO 42
<211> LENGTH: 53
<212> TYPE: DNA
<213> ORGANISM: Artificial
<220> FEATURE:
<223> OTHER INFORMATION: Primer 5'VHL2KGS15

<400> SEQUENCE: 42
ggcggcggcg gctccggtgg tggtggttct gatatcaaac tgcagcagtc agg             53

<210> SEQ ID NO 43
<211> LENGTH: 30
<212> TYPE: DNA
<213> ORGANISM: Artificial
<220> FEATURE:
<223> OTHER INFORMATION: Primer 3'VHL2KBspEI

<400> SEQUENCE: 43
aatccggatg aggagactgt gagagtggtg                                       30

<210> SEQ ID NO 44
<211> LENGTH: 25
<212> TYPE: DNA
<213> ORGANISM: Artificial
<220> FEATURE:
<223> OTHER INFORMATION: Primer 3'VHCD19BspEI (C-terminal)

<400> SEQUENCE: 44
cctccggagg agacggtgac cgtgg                                            25

<210> SEQ ID NO 45
<211> LENGTH: 73
<212> TYPE: DNA
<213> ORGANISM: Artificial
<220> FEATURE:
<223> OTHER INFORMATION: Primer CTI Polylinker

<400> SEQUENCE: 45
tctagaattc ttcgaatccg gaggtggtgg atccgatatc cccgggcatc atcaccatca      60
tcattgagtc gac                                                         73

<210> SEQ ID NO 46
<211> LENGTH: 15
<212> TYPE: PRT
<213> ORGANISM: Artificial
<220> FEATURE:
<223> OTHER INFORMATION: Peptide Linker
```

```
<400> SEQUENCE: 46

Gly Gly Gly Gly Ser Gly Gly Gly Gly Ser Gly Gly Gly Gly Ser
1               5                   10                  15

<210> SEQ ID NO 47
<211> LENGTH: 5
<212> TYPE: PRT
<213> ORGANISM: Artificial
<220> FEATURE:
<223> OTHER INFORMATION: Peptide linker

<400> SEQUENCE: 47

Gly Gly Gly Gly Ser
1               5
```